United States Patent [19]

Darnell, Jr. et al.

[11] Patent Number: 5,716,622
[45] Date of Patent: Feb. 10, 1998

[54] FUNCTIONALLY ACTIVE REGIONS OF SIGNAL TRANSDUCER AND ACTIVATORS OF TRANSCRIPTION

[75] Inventors: James E. Darnell, Jr., Larchmont; Zilong Wen, New York; Curt M. Horvath, New York; Zhong Zhong, New York, all of N.Y.

[73] Assignee: The Rockefeller University, New York, N.Y.

[21] Appl. No.: 369,796

[22] Filed: Jan. 6, 1995

[51] Int. Cl.$^6$ .................... A61K 39/385; C07K 14/715; C07K 17/02
[52] U.S. Cl. .................... 424/185.1; 424/193.1; 530/350; 530/403
[58] Field of Search .................... 530/350, 403; 424/185.1, 193.1

[56] References Cited

FOREIGN PATENT DOCUMENTS

WO 93/19179  9/1993  WIPO.

OTHER PUBLICATIONS

Darnell et al., 1994, Science 264:1415–1421.
Improta et al., 1994, Proc. Natl. Acad. Sci. USA 91:4776–80.
Shuai et al., 1994, Cell 76:821–28.
Zhong et al., 1994, Proc. Natl. Acad. Sci. USA 91:4806–4810.
Zhong et al., 1994, Science 264:95–98.
Eck et al., 1993, Nature 362:87–91.
Felder et al., 1993, Mol. Cell. Biol. 13:1449–55.
Khan et al., 1993, Proc. Natl. Acad. Sci. USA 90:6806–10.
Müller et al., 1993, EMBO J. 12:4221–28.
Müller et al., 1993, Nature 366:129–35.
Pearse et al., 1993, Proc. Natl. Acad. Sci. 90:4314–18.
Sadowski et al., 1993, Nature 362:79–83.
Sadowski et al., 1993, Science 261:1739–44.
Shuai et al., 1993, Nature 366:580–83.
Shuai et al., 1993, Science 261:1744–46.
Songyang et al., 1993, Cell 72:767–78.
Watling et al., 1993, Nature 366:166–70.
Wegenka et al., 1993, Mol. Cell. Biol. 13:276–88.
Schindler et al., 1992, Proc. Natl. Acad. Sci. USA 89:7836–39.
Schindler et al., 1992, Science 257:809–13.
Decker et al., 1991, EMBO J. 10:927–32.
Lew et al., 1991, Mol. Cell. Biol. 11:182–91.
Fu et al., 1990, Proc. Natl. Acad. Sci. USA 87:8555–59.
Wagner et al., 1990, EMBO J. 9:4477–84.

*Primary Examiner*—Christina Chan
*Assistant Examiner*—F. Pierre VanderVegt
*Attorney, Agent, or Firm*—Klauber & Jackson

[57] ABSTRACT

The present invention relates generally to intracellular receptor recognition proteins or factors, termed Signal Transducers and Activators of Transcription (STAT), to methods and compositions utilizing such factors, and to the antibodies reactive toward them, in assays and for diagnosing, preventing and/or treating cellular debilitation, derangement or dysfunction. More particularly, the present invention relates to particular functional domains of molecules that exhibit both receptor recognition and message delivery via DNA binding in receptor-ligand specific manner, i.e., that directly participate both in the interaction with the ligand-bound receptor at the cell surface and in the activity of transcription in the nucleus as a DNA binding protein. The invention likewise relates to the antibodies and other entities that are specific to the functional domain of a STAT protein and that would thereby selectively modulate its activity.

16 Claims, 18 Drawing Sheets

FIG. 6A

```
       400
1- SLA AEFRHLQLKE QK..NAGTRTNEGPLIVTEE LHSLSFETQL CQPG..LVID LETT
3- SLS AEFKHLTLRE QRCGNGGRANCDASLIVTEE LHLITFETEV YHQG..LKID LETH
4- SLS VEFRHLQPKE MKC.STGSKGNEGCHMVTEE LHSITFETQI CLYG..LTIN LETS
5- TLS AHFRNMSLKR IK.....RADRRGAESVTEE KFTVLFESQF SVGSNELVFQ VKTL
6- CCS ALFKNLLLKK IK.....RCERKGTESVTEE KCAVLFSASF TLGPGKLPIQ LQAL
2- .LI WDFGYLTLVE QRSGGSGKGSNKGPLGVTEE LHIISFTVKY TYQG..LKQE LKTD

```
                                                                               508
SLPVVV  ISNVSQLPSGWASILWYNM  LVAEPRNLSF  FLTPPCARWA  QLSEVLSWQF  SS
SLPVVV  ISNICQMPNAWASILWYNM  LTNNPKNVNF  FTKPPIGTWD  QVAEVLSWQF  SS
SLPVVM  ISNVSQLPNAWASIIWYNV  STNDSQNLVF  FNNPPSVTLG  QLLEVMSWQF  SS
SLPVVV  IVHGSQDHNATATVLWDNA  FAEPGRVP..  FAVPDKVLWP  QLCEALNMKF  KA
SLPLVV  IVHGNQDNNAKATILWDNA  FSEMDRVP..  FVVAERVPWE  KMCETLNLKF  MA
TLPVVI  ISNMNQLSIAWASVLWFNL  LSPNLQNQQF  FSNPPKAPWS  LLGPALSWQF  SS
```

(secondary structure annotation arrows: B, H, h below alignment)

… # FUNCTIONALLY ACTIVE REGIONS OF SIGNAL TRANSDUCER AND ACTIVATORS OF TRANSCRIPTION

The research leading to the present invention was supported by National Institute of Health Grant Nos. AI34420 and AI32489. Accordingly, the Government may have certain rights in the invention.

FIELD OF THE INVENTION

The present invention relates generally to intracellular receptor recognition proteins or factors, termed Signal Transducers and Activators of Transcription (STAT), to methods and compositions utilizing such factors, and to the antibodies reactive toward them, in assays and for diagnosing, preventing and/or treating cellular debilitation, derangement or dysfunction. More particularly, the present invention relates to particular functional domains of molecules that exhibit both receptor recognition and message delivery via DNA binding in receptor-ligand specific manner, i.e., that directly participate both in the interaction with the ligand-bound receptor at the cell surface and in the activity of transcription in the nucleus as a DNA binding protein. The invention likewise relates to the antibodies and other entities that are specific to the functional domain of a STAT protein and that would thereby selectively modulate its activity.

BACKGROUND OF THE INVENTION

The STAT proteins have the dual purpose of, first, signal transduction from ligand-activated receptor kinase complexes followed by nuclear translocation and DNA binding to activate transcription (Darnell et al., 1994, Science 264:1415–1421). To function as specific transcriptional activators, STAT proteins by themselves or in combination with other proteins must have the ability to recognize specific DNA sequence elements in the promoters of their target genes. The binding of the STATs to DNA occurs only after tyrosine phosphorylation when the proteins form either homodimers (Shuai et al., 1994, Cell 76:821–828) or heterodimers (Schindler et al., 1992, Science 257:809–815; Zhong et al., 1994, Proc. Natl. Acad. Sci. USA 91:4806–4810; Zhong et al., 1994, Science 264:95–98) that bind DNA either alone or in combination with other proteins (Fuet ai., 1990, Proc. Natl. Acad. Sci. USA 87:8555–8559; Schindler et al., 1992, Science 257:809–815). Since a number of mutations in the STAT proteins block phosphorylation and thus dimerization (Shuai et al., Science 261:1744–1746; Improta et al., 1994, Proc. Natl. Acad. Sci. USA 91:4776–4780), and none of the STAT sequences resembles previously well-defined DNA binding domains in other proteins, it has not been possible to quickly and easily define the DNA binding domains of the STATs.

U.S. Ser. No. 07/980,498, filed Nov. 23, 1992, now abandoned, which is a Continuation-In-Part of copending U.S. Ser. No. 07/854,296, filed Mar. 19, 1992, now abandonded and International Patent Publication No. WO 93/19179 (published 30 Sep. 1993, by James E. Darnell, Jr. et al.) (each of which is hereby incorporated by reference in its entirety) disclosed the existence of receptor recognition factors, now termed signal transducers and activators of transcription (STAT). The nucleotide sequences of cDNA encoding receptor recognition factors having molecular weights of 113 kD (i.e., 113 kD protein, Stat113, or Stat2), 91 kD (i.e., 91 kD protein, Stat91, or Stat1α) and 84 kD (i.e., 84 kD protein, Stat84, or Stat1β) are reiterated herein in SEQ ID NOS:1, 3, and 5, respectively; the corresponding deduced amino acid sequences of the STAT proteins are shown in SEQ ID NOS:2, 4, and 6, respectively. Stat84 was found to be a truncated form of Stat91. There is 42% amino acid sequence similarity between Stat113 and Stat91/84 in an overlapping 715 amino acid sequence, including four leucine and one valine heptad repeats in the middle helix region, and several tyrosine residues were conserved near the ends of both proteins. The receptor recognition proteins thus possess multiple properties, among them: 1) recognizing and being activated during such recognition by receptors; 2) being translocated to the nucleus by an inhibitable process (e.g., NaF inhibits translocation); and 3) combining with transcription activating proteins or acting themselves as transcription activation proteins, and that all of these properties are possessed by the proteins described herein. In particular, the proteins are activated by binding of interferons to receptors on cells, in particular interferon-α (all three Stat proteins) and interferon-γ (Stat91).

U.S. application Ser. No. 08/126,595, filed Sep. 24, 1993, now abandoned which is incorporated herein by reference in its entirety, relates to identification of functional sites of Stat1α, particularly identification of tyrosine-701 as the phosphorylation site, and the presence of a functional SH2 domain in the protein. This application further disclosed a murine Stat1 homolog (the nucleotide sequence is shown in SEQ ID NO:7; the amino acid sequence is shown in SEQ ID NO:8). Stat1 was further found to be active as a homodimer (Stat1α-Stat1α, Stat1α-Statβ, and Statβ-Statβ) (U.S. application Ser. No. 08/212,184, filed Mar. 11, 1994, pending which is incorporated herein by reference in its entirety). Additional Stat proteins, Stat3 (nucleotide sequence in SEQ ID NO:9 and amino acid sequence in SEQ ID NO:10) and Stat4 (nucleotide sequence in SEQ ID NO:11 and amino acid sequence in SEQ ID NO:12), were disclosed and characterized in U.S. applications Ser. No. 08/126,588, filed Sep. 24, 1993, now abandoned and Ser. No. 08/212,185, filed Mar. 11, 1994, pending each of which is incorporated herein by reference in its entirety.

SUMMARY OF THE INVENTION

In its broadest aspect, the present invention is related to the identification of a specific region on a STAT protein associated with activation of transcription. In particular, the present invention relates to the DNA-binding domain of a STAT protein, and to a serine phosphorylation site of a STAT protein. Of particular interest are the STAT proteins Stat1α (SEQ ID NOS:4 and 8), Stat1β (SEQ ID NO:6), Stat2 (SEQ ID NO:2), Stat3 (SEQ ID NO:10), and Stat4 (SEQ ID NO:12).

Accordingly, in a first aspect, the invention is directed to a peptide, which peptide consists of no more than about 110 amino acid residues and has an amino acid sequence corresponding to the sequence of the same number of amino acid residues from a DNA-binding domain of a STAT protein. In particular, the DNA-binding domain is in the region from amino acid residue 400 to amino acid residue 510 of the STAT protein. In a specific embodiment, the region from amino acid residue 400 to amino acid residue 510 of the STAT protein has an amino acid sequence selected from the group consisting of:

SLAAEFRHLQLKEQKNAGTRTNEGPLIVTEELHSLSFETQLCQPGLV
IDLETTSLPVVVISNVSQLPSGWASILWYNMLVAEPRNLSFFLTPPC
ARWAQLSEVLSWQFSS (SEQ ID NO: 13)

SLSAEFKHLTLREQRCGNGGRANCDASLIVTEELHLITFETEVYHQG
LKIDLETHSLPVVVISNICQMPNAWASILWYNMLTNNPKNVKFFTK
PPIGTWDQVAEVLSWQFSS (SEQ ID NO: 14)

SLSVEFRHLQPKEMKCSTGSKGNEGCHMVTEELHSITFETQICLYG
LTINLETSSLPVVMISNVSQLPNAWASIIWYNVSTNDSQNLVFFNN
PPSVTLGQLLEVMSWQFSS (SEQ ID NO: 15)

TLSAHFRNMSLKRIKRADRRGAESVTEEKFTVLFESQFSVGSNELV
FQVKTLSLPVVVIVHGSQDHNATATVLWDNAFAEPGRVPFAVPDK
VLWPQLCEALNMKFKA (SEQ ID NO: 16)

CCSALFKNLLLKKIKRCERKGTESVTEEKCAVLFSASFTLGPGKLP
IQLQALSLPLVVIVHGNQDNNAKATILWDNAFSEMDRVPFVVAER
VPWEKMCETLNLKFMA (SEQ ID NO: 17)

LIWDFGYLTLVEQRSGGSGKGSNKGPLGVTEELHIISFTVKYTYQG
LKQELKTDTLPVVIISNMNQLSIAWASVLWFNLLSPNLQNQQFFSN
PPKAPWSLLGPALSWQFSS (SEQ ID NO: 18)

In a further embodiment, the invention relates to a chimeric protein containing a STAT DNA-binding domain. In a specific embodiment, the chimeric protein is a second STAT protein in which the wild-type DNA-binding domain is substituted with the DNA-binding domain from the STAT protein.

The invention further provides antibodies specific for the DNA binding domain of a Stat protein, and methods for generating such antibodies. Accordingly, the invention is further directed to an immunogenic composition comprising the peptide described above in an admixture with an adjuvant. In a specific aspect, the peptide is conjugated to a carrier molecule. A method for generating an antibody to a DNA-binding domain of a STAT protein comprises immunizing an animal with the immunogenic composition.

In a related aspect, the invention is directed to an antagonist of a STAT protein for binding to DNA, which antagonist is a compound capable of binding to a DNA-binding domain on a STAT protein. More particularly, the DNA-binding domain is in the region from amino acid residue 400 to amino acid residue 510 of the STAT protein. In a specific embodiment, the region from amino acid residue 400 to amino acid residue 510 of the STAT protein has an amino acid sequence selected from the group consisting of:

SLAAEFRHLQLKEQKNAGTRTNEGPLIVTEELHSLSFETQLCQPGLV
IDLETTSLPVVVISNVSQLPSGWASILWYNMLVAEPRNLSFFLTPPC
ARWAQLSEVLSWQFSS (SEQ ID NO: 13)

SLSAEFKHLTLREQRCGNGGRANCDASLIVTEELHLITFETEVYHQG
LKIDLETHSLPVVVISNICQMPNAWASILWYNMLTNNPKNVKFFTK
PPIGTWDQVAEVLSWQFSS (SEQ ID NO: 14)

SLSVEFRHLQPKEMKCSTGSKGNEGCHMVTEELHSITFETQICLYG
LTINLETSSLPVVMISNVSQLPNAWASIIWYNVSTNDSQNLVFFNN
PPSVTLGQLLEVMSWQFSS (SEQ ID NO: 15)

TLSAHFRNMSLKRIKRADRRGAESVTEEKFTVLFESQFSVGSNELV
FQVKTLSLPVVVIVHGSQDHNATATVLWDNAFAEPGRVPFAVPDK
VLWPQLCEALNMKFKA (SEQ ID NO: 16)

CCSALFKNLLLKKIKRCERKGTESVTEEKCAVLFSASFTLGPGKLP
IQLQALSLPLVVIVHGNQDNNAKATILWDNAFSEMDRVPFVVAER
VPWEKMCETLNLKFMA (SEQ ID NO: 17)

LIWDFGYLTLVEQRSGGSGKGSNKGPLGVTEELHIISFTVKYTYQG
LKQELKTDTLPVVIISNMNQLSIAWASVLWFNLLSPNLQNQQFFSN
PPKAPWSLLGPALSWQFSS (SEQ ID NO: 18)

In specific aspects, the antagonist is selected from the group consisting of a peptide and an antibody. In particular, the antibody may be selected from the group consisting of a polyclonal antibody, a monoclonal antibody, a single chain antibody, an F(ab')$_2$ fragment of an immunoglobulin, an F(ab') fragment of an immunoglobulin, an Fv fragment of an immunoglobulin, and an Fab fragment of an immunoglobulin.

The invention further provides a method for identifying any chemical compound that is an antagonist of a STAT protein for binding to DNA. The method comprises contacting a biological sample containing the STAT protein and an oligonucleotide probe to which the STAT protein binds with a candidate compound, e.g., by mixing the putative inhibitor with the STAT protein and the oligonucleotide, and detecting whether the level of binding of the STAT protein to the probe is decreased relative to the level of binding of the STAT protein to the probe in a control biological sample. According to the invention, a decrease in the level of binding of the level of binding of the STAT protein to the probe indicates that the candidate is an antagonist of binding of the STAT protein to DNA.

Preferably, the compound under test would be capable of binding to or directly interacting with a DNA-binding domain on the STAT protein. Binding to a DNA-binding domain on the STAT protein can be tested, for example, by detecting binding of the compound to the peptide corresponding to the DNA-binding domain, as described above, or by detecting specific binding to a chimeric protein, such as (and preferably) a STAT protein in which the wild-type DNA-binding domain is substituted with a DNA-binding domain from a different STAT protein. More particularly, the DNA-binding domain is in the region from amino acid residue 400 to amino acid residue 510 of the STAT protein. In a specific embodiment, the region from amino acid residue 400 to amino acid residue 510 of the STAT protein has an amino acid sequence as set forth above.

In a specific embodiment, the candidate antagonist compound is a compound from a combinatorial library. In a further specific embodiment, the candidate compound is selected from the group consisting of a peptide and an antibody.

The invention further extends to a method for inhibiting signal transduction and activation of transcription mediated by a STAT protein comprising introducing a STAT protein having a mutation in the DNA-binding domain into a cell, whereby binding of a ligand to a receptor associated with the STAT protein leads to activation of the mutant form of the STAT protein which binds DNA with reduced affinity compared to the wild-type protein. As noted above, more particularly the DNA-binding domain is in the region from amino acid residue 400 to amino acid residue 510 of the STAT protein. In a specific embodiment, the region from amino acid residue 400 to amino acid residue 510 of the STAT protein has an amino acid sequence set forth above.

The mutation in the STAT protein may be selected from the group consisting of mutation of at least one glutamic acid residue corresponding to glutamic acid-434 or glutamic acid residue-435 of Stat1 or Stat3, and mutation of at least one valine residue corresponding to valine-461, valine-462, or valine-463 of Stat1 or Stat3. In a specific embodiment, exemplified infra, the mutation is of amino acids corresponding to glutamic acid-434 and glutamic acid-435 of Stat1 or Stat3, in particular substitution of alanine for glutamic acid in each residue.

The present invention relates to transgenic treatment for inhibiting signal transduction and activation of transcription mediated by a STAT protein. For example, the mutant STAT protein may be introduced into the cell by introducing a gene encoding the mutant STAT protein operatively associated with an expression control sequence for expression in the cell, whereby the mutant STAT protein is expressed by the cell. The gene may be introduced to cells in vivo or ex vivo.

In another aspect, the invention provides a method for inhibiting signal transduction and activation of transcription mediated by a STAT protein comprising introducing an antagonist of binding of a STAT protein to DNA, whereby binding of a ligand to a receptor associated with the STAT protein leads to activation of the STAT protein, which binds DNA with reduced affinity compared to the wild-type protein. The antagonist may be selected from the group consisting of a peptide and an antibody. For example, the antagonist may be an antibody selected from the group consisting of a polyclonal antibody, a monoclonal antibody, a single chain antibody, an F(ab')$_2$ fragment of an immunoglobulin, an F(ab') fragment of an immunoglobulin, an Fv fragment of an immunoglobulin, and an Fab fragment of an immunoglobulin.

In a further aspect, the invention further relates to the amplification of transcription activation that results from phosphorylation of a C-terminal serine residue of a STAT protein, which serine phosphorylation is not specific for receptor-binding, but relates to the state of cellular activation, i.e., the activity of serine kinases in the cell. Accordingly, the invention provides a method for inhibiting signal transduction and activation of transcription mediated by a STAT protein in response to binding of a ligand to a specific receptor for the ligand comprising introducing a STAT protein having a mutation in the serine phosphorylation site into a cell, whereby binding of the ligand to a receptor associated with the STAT protein leads to partial activation of the mutant form of the STAT protein which has reduced transcriptional activation capacity compared to the wild-type STAT protein. Preferably, the transcription activation capacity is reduced to 20% of the activity of the wild-type STAT protein. In a specific embodiment, relating to transgenic treatment, the mutant STAT protein is introduced into the cell by introducing a gene encoding the mutant STAT protein operatively associated with an expression control sequence for expression in the cell, whereby the mutant STAT protein is expressed by the cell. For example, the gene may be introduced to cells in vivo or ex vivo. In a specific embodiment, the STAT protein is Stat1α and the ligand is interferon-γ. In another specific embodiment, the STAT protein is Stat3 and the ligand is interleukin-6 (IL-6) or epidermal growth factor (EGF).

In a related aspect, the invention provides a method for detecting the level of activation of a STAT protein in a biological sample as a result of binding of ligand to a specific receptor for ligand comprising detecting the presence of a phosphorylated tyrosine residue and the presence of a phosphorylated serine residue on the STAT protein. Phosphorylation of tyrosine only is indicative of low level specific activation of the STAT protein; phosphorylation of serine only is indicative of general activation of the cell, but not of activation of the STAT protein; and phosphorylation of both tyrosine and serine is indicative of maximal activation of the STAT protein. In a specific embodiment, the STAT protein is Stat1α and the ligand is interferon-γ. In another specific embodiment, the STAT protein is Stat3 and the ligand is interleukin-6 (IL-6) or epidermal growth factor (EGF). In a specific aspect, the activation is associated with a disease or disorder selected from the group consisting of oncogenesis, inflammation, autoimmunity, infection, and the presence of a parasite.

Accordingly, it is a principal object of the present invention to provide a novel domain or region associated with activation of transcription activity of the family of STAT proteins.

Is a particular object of the invention to provide compound that inhibit DNA-binding and transcription activation activities of the factors.

It is a further object of the present invention to provide antibodies to the STAT protein domains, particularly the DNA-binding domain and the serine phosphorylation site, and methods for their preparation, including recombinant means.

It is a further object of the present invention to provide a method for detecting the presence of the STAT protein phosphorylated on tyrosine and on serine, in mammals in which invasive, spontaneous, or idiopathic pathological states are suspected to be present.

It is a further object of the present invention to provide a method and associated assay system for screening substances such as drugs, agents and the like, potentially effective in combating the adverse effects of the recognition factor and/or its subunits in mammals.

It is a still further object of the present invention to provide a method for the treatment of mammals to control the amount or activity of the recognition factor or subunits thereof, so as to alter the adverse consequences of such presence or activity, or where beneficial, to enhance such activity, of the STAT protein.

It is a still further object of the present invention to provide a method for the treatment of mammals to control the mount or activity of the recognition factor or its subunits, so as to treat or avert the adverse consequences of invasive, spontaneous or idiopathic pathological states.

It is a still further object of the present invenl ion to provide pharmaceutical compositions for use in therapeutic methods which comprise or are based upon the recognition factor, its subunits, their binding partner(s), or upon agents or drugs that control the production, or that mimic or antagonize the activities of the recognition factors.

Other objects and advantages will become apparent to those skilled in the art from a review of the ensuing description which proceeds with reference to the following illustrative drawings.

BRIEF DESCRIPTION OF THE DRAWINGS

FIG. 1C depicts the Electrophoretic Mobility Shift Assay (EMSA) with Labeled Stat1 and Stat3 Consensus Site Oligonucleotides. A radio labelled probe that corresponds either to the Stat1 (S1) or Stat3 (S3) consensus sites was incubated with HepG2 nuclear extracts of cells that were untreated (−) or treated (+) with IL6. Positions of SIF A SIF B and SIF C complexes are marked. Supershifting of the IL6-induced complexes with Stat1 (1C) or Stat3 (3C) specific antisera is indicated above the lanes. Probes are identified above the lanes. (*) Indicates the position of the constitutive comigrating band described in the text.

FIG. 5A EMSA analysis of DNA:protein complexes. Nuclear extracts from EGF-treated COS cells transfected with Stat3, mutant EE>AA or mutant VVV>AAA (see Methods) were incubated with labeled M67 probe to reveal DNA binding complexes. Position of SIF A is marked. FIG. 5B Phosphotyrosine immunoblotting. Extracts from the cells in panel A were immunoprecipitated with Stat3-specific antiserum, separated by SDS PAGE, transferred to nitrocellulose and probed with monoclonal antibody PY20. FIG. 5C Co-immunoprecipitation of Stat1 and Stat3 mutants. COS cells were transfected with FLAG-tagged Stat3 or routants along with untagged Stat1 and treated (+) or not treated (−) with EGR. FLAG immunoprecipitates were separated by SDA PAGE, transferred to nitrocellulose, and probed with Stat1 specific antiserum (top panel). STAT1 refers to transfection with Stat1 alone. Bottom panel is an immunoblot with FLAG specific monoclonal antibody to demonstrate similar expression levels in the transleered cells.

FIGS. 6A–6B Alignment of STAT Family Members in the Putative DNA Binding Region. Lines below indicate boundaries of putative helices (H,h) and beta sheets (B,b) predicted by the algorithms of Chou and Fasman for each of the family members. Numbering above the alignment refers to the Stat1 sequence. The conserved amino acids mutated in this study are overlined. Sequences were aligned using the GCG pileup program and secondary structure was predicted using the GCG peptide structure program (Genetics Computer Group, 1991).

FIG. 12B shows the comparision of the run-on transcriptional signal from the IRF1 gene in the two U3A cell derivatives.

DETAILED DESCRIPTION

Figure 1A:
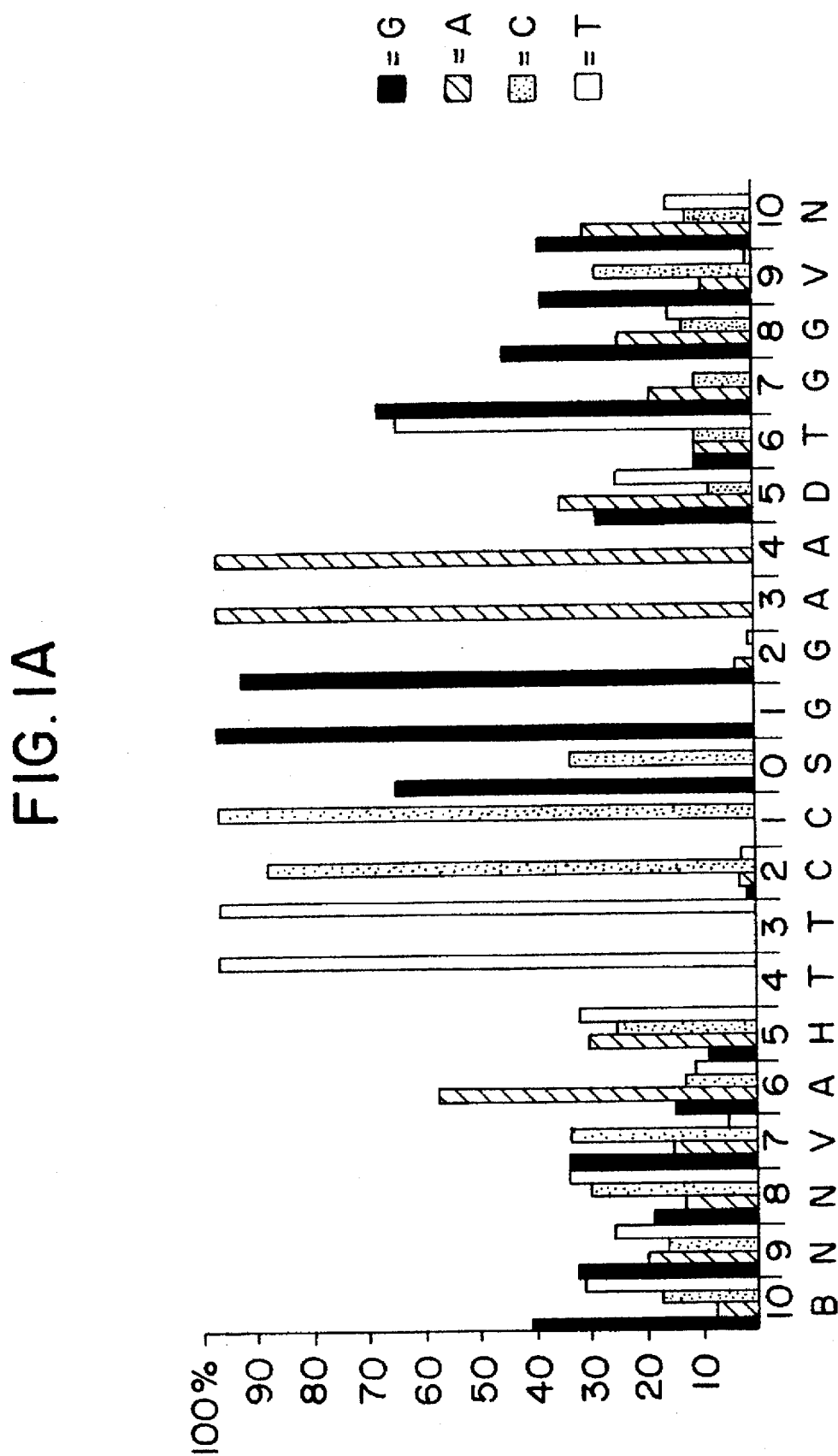
FIGS. 1A–1C FIGS. 1A–1B show the Binding Site Selection for Stat1 and Stat3. Graphical representation of the nucleotide frequency in 55 independent binding sites selected by Stat1 (FIG. 1A) and Stat3 (FIG. 1B) in vitro from a pool of random oligodeoxynucleotides. Sequences were aligned to fit the TYNNNNNAA consensus previously recognized to be present in natural GAS elements (Table 1). The common core consensus is underlined with the central nucleotide assigned position zero. The optimum consensus sequence and base preference in the flanking region is written beneath the graphs in I.U.B. code. N=G,C, AT,T; D=G,A,T; H=A,C,T; S=G,C; K=G,T; B=G,C,T; V=G,A,C; R=G, A.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

The terms "receptor recognition factor", "receptor recognition-tyrosine kinase factor", "receptor recognition factor/tyrosine kinase substrate", "receptor recognition/ transcription factor", "recognition factor", "recognition factor protein(s)", "signal transducers and activators of transcription", "STAT", and any variants not specifically listed, may be used herein interchangeably, and as used throughout the present application and claims refer to proteinaceous material including single or multiple proteins, and extends to those proteins having the amino acid sequence data described herein and presented in SEQ ID NOS:2, 4, 6, 8, 10, and 12. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "receptor recognition factor", "recognition factor", "recognition factor protein(s)", "signal transducers and activators of transcription", and "STAT" are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. NH2 refers to the free amino group present at the amino terminus of a polypeptidt. COOH refers to the free carboxyl group present at the carboxyl terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo, i.e., capable of replication under its own control.

A "vector" is a replicon, such as plasmid, phage or cosmid, to which another DNA segment may be attached so as to bring about the replication of the attached segment.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% forrrtamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or hornology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-0.51). For hybridization with shorter nucleic acids, i.e., oligonucleotides, the position of mismatches becomes more important, and the length of the oligonucleotide determines its specificity (see Sambrook et al., supra, 11.7-11.8). Preferably a minimum length for a hybridizable nucleic acid is at least about 10 nucleotides; more preferably at least about 15 nucleotides; most preferably the length is at least about 20 nucleotides.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of hornology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

The term "oligonucleotide", as used herein in referring to the probe of the present invention, is defined as a molecule comprised of two or more ribonucleotides or deoxyribonucleotides, preferably more than three. Its exact size will depend upon many factors which, in turn, depend upon the ultimate function and use of the oligonucleotide.

A "nucleotide probe" as used herein refers to an oligonucleotide of at least about 9 bases, which has a sequence corresponding to a portion of the DNA to which a STAT protein binds, and thus is capable of binding to a STAT protein. Preferably, a nucleotide probe binds to the STAT protein with high specificity and affinity. Such a nucleotide probe corresponds to a specific STAT binding site. However, nucleotide probes of the invention may correspond to a general STAT binding site on DNA as well.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

Accordingly, the term "sequence similarity" in all its grammatical forms refers to the degree of identity or correspondence between nucleic acid or amino acid sequences of proteins that do not share a common evolutionary origin (see Reeck et al., supra).

Two DNA sequences are "substantially homologous" or "substantially similar" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

Similarly, two amino acid sequences are "substantially homologous" or "substantially similar" when greater than 70% of the amino acids are identical, or functionally identical. Preferably, the similar or homologous sequences are identified by alignment using, for example, the GCG (Genetics Computer Group, Program Manual for the GCG Package, Version 7, Madison, Wis.) pileup program.

The term "corresponding to" is used herein to refer similar or homologous sequences, whether the exact position is identical or different from the molecule to which the similarity or homology is measured. For example, as demonstrated in FIGS. 6A–6B, infra, the sequences of the DNA-binding domains of the STAT proteins can be aligned, and the corresponding amino acid residues determined, despite the deletion of amino acid residues at some positions in one STAT protein compared to another. Thus, the term "corresponding to" refers to the sequence similarity, and not the numbering of the amino acid residues or nucleotide bases.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. An "antibody combining site" or "antigen recognition site" is that structural portion of an antibody molecule comprised of heavy and light chain variable and hypervariable regions that specifically binds antigen. The phrase "antibody molecule" in its various grammatical forms as used herein contemplates both an intact immunoglobulin molecule and an immunologically active portion of an immunoglobulin molecule. Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein. The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

A molecule is "antigenic" when it is capable of specifically interacting with an antigert recognition molecule of the immune system, such as an immunoglobulin (antibody) or T cell antigen receptor. An antigenic polypeptide contains at least about 5, and preferably at least about 10, amino acids. An antigenie portion of a molecule can be that portion that is immunodominant for antibody or T cell receptor recognition, or it can be a portion used to generate an antibody to the molecule by conjugating the antigenie portion to a carrier molecule for immunization. A molecule that is antigenie need not be itself immunogenic, i.e., capable of eliciting an immune response without a carrier.

The term "adjuvant" refers to a compound or mixture that enhances the immune response to an antigen. An adjuvant can serve as a tissue depot that slowly releases the antigen and also as a lymphold system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. Preferably, the adjuvant is pharmaceutically acceptable.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, exeipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternativea thea therapeutically effective amount is sufficient to cause an improvement in a clinically significant condition in the host.

The term "biological sample" is used herein to refer to a sample containing cells that express or may express a STAT protein. Such cells may be obtained from a subject, or from in vitro culture. The term "biological sample" further extends to an extract of cells from either source.

The term "about" is used herein to mean within a 10% variance from the figure given, preferably within a 5% variance, and more preferably within a 1% variance.

As noted above, the present invention relates to the discovery that Stat1 and Stat3, which are two members of the ligand-activated transcription factor family that serve the dual functions of signal transducers and activators of transcription, select similar, but not identical, optimum binding sites from random oligonucleotides. Differences in their binding affinity were readily apparent with natural STAT binding sites. However, unlike other DNA binding proteins, fragments of the STAT proteins could not be shown to bind to DNA.

To take advantage of the different affinities for specific DNA sequences, chimerio Stat1:Stat3 molecules were used to locate the amino acids that could discriminate a general binding site from a specific binding site. The amino acids between residues ~400 and ~500 of these ~750 amino acid long proteins were discovered to determine the DNA binding site specificity. Mutations within this region result in Stat proteins which are activated normally by tyrosine phosphorylation and which dimerize, but have greatly reduced DNA binding affinities.

The invention further relates to the discovery that phosphorylation of a serine residue at position 727, in the carboxyl-terminus, of Stat1α is required for maximal interferon-γ (IFN-γ) dependent transcriptional response. This observation has important implications for the detection of the level of activation of a cell, based on activation of a STAT protein. Moreover, this observation provides the first link between ligand activated STATs and serine kinases in transcriptional control.

The present invention particularly relates to functionally active regions of the STAT proteins, e.g., as exemplified herein with portions of Stat1α, particularly such fragments that contain a DNA binding domain, and a C-terminal serine residue that is phosphorylated non-specifically as a consequence of cellular activation, but which is critical for maximum transcriptional activation.

The invention contemplates antagonists of STAT proteins targeted to the DNA-binding domain. In another aspect, the invention is directed to mutant forms of STAT proteins that can compete as substrates for tyrosine phosphorylation and dimerization, but which are poor DNA-binding proteins, or have reduced transcriptional activation activity.

Subsequent to the filing of the initial patent applications directed to the present invention, the inventors have termed each member of the family of receptor recognition factors as a signal transducer and activator of transcription (STAT) protein. Each STAT protein is designated by the apparent molecular weight (e.g., Stat113, Stat91, Stat84, etc.), or by the order in which it has been identified (e.g., Stat1α [Stat91], Stat1β [Stat84], Stat2 [Stat113], Stat3 [a murine protein also termed 19sf6], and Stat4 [a murine STAT protein also termed 13sf1]). As will be readily appreciated by one of ordinary skill in the art, the choice of name has no effect on the intrinsic characteristics of the factors described herein, which were first disclosed in International Patent Publication No. WO 93/19179, published 30 September 1993. The present inventors have chosen to adopt this newly derived terminology herein as a convenience to the skilled artisan who is familiar with the subsequently published papers relating to the same, and in accordance with the proposal to harmonize file terminology for the novel class of proteins, and nucleic acids encoding the proteins, disclosed by the instant inventors. The terms [molecular weight] kd receptor recognition factor, Stat[molecular weight], and Stat [number] are used herein interchangeably, and have the meanings given above. For example, the terms 91 kd protein, Stat91, and Stat1α refer to the same protein, and in the appropriate context refer to the nucleic acid molecule encoding such protein.

As stated above, the present invention also relates to a recombinant DNA molecule or cloned gene, or a degenerate variant thereof, which encodes a receptor recognition factor, or a fragment thereof, that encodes a DNA binding domain, or a chimeric protein containing a functionally active DNA binding domain of a STAT protein.

Diagnostic and therapeutic applications are raised by the identification of the DNA-binding domain of STAT proteins, and that C-terminal serine phosphorylation of a STAT protein appears to be required for maximum signal transduction activity. As suggested earlier and elaborated further on herein, the present invention contemplates pharmaceutical intervention in the cascade of reactions in which the STAT protein is implicated, to modulate the activity initiated by the stimulus bound to the cellular receptor.

Thus, in instances where it is desired to reduce or inhibit the gene activity resulting from a particular stimulus or factor, an appropriate antagonist of the DNA-binding domain of a STAT protein could be introduced to block the interaction of the STAT protein with its DNA binding site. Similarly, mutation of the C-terminal phosphorylation site, or introduction of a mutant STAT protein lacking such a C-terminal phosphorylation site, would be expected to lead to a decrease in the level of transcriptional activation mediated by a STAT protein containing such a serine phosphorylation site.

As discussed earlier, the antagonists of the STAT binding to DNA, or that are specific for the phosphoserine STAT proteins, may be prepared in pharmaceutical compositions, with a suitable carrier and at a strength effective for administration by various means to a patient experiencing an adverse medical condition associated specific transcriptional stimulation for the treatment thereof. Preferably, the pharmaceutical formulation will provide for transmembrane migration of the antagonists, which will be active in the cytoplasm. A variety of administrative techniques may be utilized, among them parenteral techniques such as subcutaneous, intravenous and intraperitoneal injections, catheterizations and the like. Average quantities of the recognition factors or their subunits may vary and in particular should be based upon the recommendations and prescription of a qualified physician or veterinarian.

Also, antibodies including both polyclonal and monoclonal antibodies, may possess certain diagnostic or therapeutic (inhibitory) applications and may for example, be utilized for the purpose of detecting and/or measuring conditions such as cellular activation as a result of vital infection, inflammation, or the like. For example, the STAT protein DNA-binding domain, or a peptide corresponding to a STAT protein epitope containing the phosphorylated serine residue, may be used to produce both polyclonal and monoclonal antibodies to themselves in a variety of cellular media, by such well known techniques as immunization of rabbit using Complete and Incomplete Freund's Adjuvant and the hybridoma technique utilizing, for example, fused mouse spleen lymphocytes and myeloma cells, respectively. Preferably, such proteins are conjugated to a carrier molecule, as described above. These techniques have been described in numerous publications in great detail, e.g., International Patent Publication WO 93/19179, and do not bear repeating here.

Likewise, small molecules that mimic or antagonize the activity(ies) of the receptor recognition factors of the invention may be discovered or synthesized, and may be used in diagnostic and/or therapeutic protocols.

Identification of important regions of the STAT proteins for function provides a basis for screening for drugs capable of specific interaction with the functionally relevant domains. According, in addition to rational design of compounds that bind to, and preferably competitively inhibit the functional activity of the STAT protein, i.e., antagonism, based on the structure of relevant domain, the present invention contemplates an alternative method for identifying specific binding compounds of the DNA-binding domain or the region containing phosphoserine using various screening assays known in the art.

Any screening technique known in the art can be used to screen for STAT DNA-binding antagonists. The present invention contemplates screens for small molecule ligands or ligand analogs and mimics, as well as screens for natural figands that bind to and antagonize STAT activates in vivo.

Knowledge of the primary sequence of the STAT DNA-binding domain, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" (Scott and Smith, 1990, Science 249:386–390; Cwirla, et al., 1990, Proc. Natl. Acad. Sci., 87:6378–6382; Devlin et al., 1990, Science, 249:404–406), very large libraries can be constructed ($10^6$–$10^8$ chemical entities). A second approach uses primarily chemical methods, of which the Geysen method (Geysen et al., 1986, Molecular Immunology 23:709–715; Geysen et al. 1987, J. immunologic Method 102:259–274) and the recent method of Fodor et al. (1991, Science 251, 767–773) are examples. Furka et al. (1988, 14th International Congress of Biochemistry, Volume 5, Abstract FR:013; Furka, 1991, Int. J. Peptide Protein Res. 37:487–493), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., 1993, "Generation and screening of an oligonucleotide encoded synthetic peptide library," Proc. Natl. Acad. Sci. USA 90:10700–4; Lam et al., International Patent Publication No. WO 92/00252, each of which is incorporated herein by reference in its entirety), and the like can be used to screen for STAT DNA-binding domain or phosphoserine region ligands according to the present invention.

The screening can be performed directly using peptides corresponding to the DNA binding domain or the region containing the phosphoserine residue. Alternatively, chimeric proteins, which contain the DNA binding domain (or the serine residue) may be used, as such proteins will contain the element specifically under investigation. Specific examples of such chimeric proteins are disclosed in the Examples, infra.

The reagents that contain the STAT DNA-binding domain (e.g., the approximately 100 amino acid residue polypeptide, or a chimerio protein), or the serine residue, can be labeled for use in the screening assays. In one embodiment, the compound may be directly labeled. In another embodiment, a labeled secondary reagent may be used to detect binding of tile compound to a solid phase support containing a binding molecule of interest. Binding may be detected by in situ formation of a chromophore by an enzyme label. Suitable enzymes include, but are not limited to, alkaline phosphatase and horseradish peroxidase. Other labels for use in the invention include colored latex beads, magnetic beads, fluorescent labels (e.g., fluore. scene isothiocyanate (FITC), phycoerythrin (PE), Texas red (TR), rhodamine, free or chelated lanthanide series salts, especially $Eu^{3+}$, to name a few fluorophores), chemiluminescent molecules, radio-isotopes, or magnetic resonance imaging labels.

As suggested earlier, the diagnostic method of the present invention comprises examining a cellular sample or medium by means of an assay including an effective amount of a reagent that specifically binds to a serine-phosphorylated STAT protein. Preferably, such a reagent is an antibody, preferably an affinity-purified polyclonal antibody, and more preferably a mAb. In addition, it is preferable for the anti-recognition factor antibody molecules used herein be in the form of Fab, Fab', F(ab')₂ or F(v) portions or whole antibody molecules. As previously discussed, patients capable of benefiting from this method include those suffering from cancer, a pre-cancerous lesion, a viral infection or other like pathological derangement. Methods for determining and optimizing the ability of anti-recognition factor antibodies to assist in the examination of the target cells are all well-known in the art.

In a specific aspect, the present invention relates to detection of both phosphotyrosine and phosphoserine on a STAT protein, which is indicative of maximum activity of the STAT protein, and thus an indicator of the degree of cellular activation. Since cellular activation is associated with certain pathological states, as discussed above, the present invention provides an advantageous method for evaluating cellular activation. Moreover, the present invention is the first instance known to the inventors in which the specific tyrosine phosphorylation activation pathway and the general serine phosphorylation activation pathway cross in the same trascription activation factor. Accordingly, this discovery has important implications for detection of diseases or disorders, i.e., pathological conditions, associated with cellular activation.

Detection of phosphorylation of tyrosine and serine can be accomplished by any techniques known in the art, including measuring the level of phosphorylation per unit mass of protein; using specific phosphatases and an appropriate detection system to detect specific phosphorylation; using antibodies generated against the phosphorylated forms of the proteins; or using well known biochemical techniques, as described in the Examples, infra.

The present invention further contemplates therapeutic compositions useful in practicing the therapeutic methods of this invention. A subject therapeutic composition includes, in admixture, a pharmaceutically acceptable excipient (carrier) and one or more of an antagonist of STAT binding to DNA, e.g., a molecule that specifically interacts with the DNA-binding domain of a STAT protein, as described herein as an active ingredient.

Alternatively, a mutant STAT, which has been mutated in the DNA-binding domain or in the serine phosphorylation site can be introduced into the cells of a subject. According to the present invention, the presence of such mutant forms of the STAT proteins, which are capable of interacting with the receptor, being phosphorylated on tyrosine, and translocating to the nucleus, can be used as "decoys." Such proteins, when dimerized with other STAT proteins (either with a mutant or wild-type form of the protein, or with another STAT protein), are expected to bind to the DNA with dower affinity, and thus be less effective at transcription activation. Similarly, such proteins that are mutated at the serinerresidue which is phosphorylated in the most active state would be expected to be less efficient at transcription activation. Specific mutations that lead to reduction of transcription activation activity, but have no effect on tyrosine phosphorylation or dimerization, are shown in the Example, infra.

In a preferred aspect, such a "decoy" mutant STAT protein is introduced into a cell via transgenic therapy.

The present invention contemplates preparation of a gene encoding a mutant form of a STAT protein, wherein the mutation is found in the DNA binding domain, or is a mutation of the C-terminal serine residues that is phosphorylated in the highly functional forms of the protein. As used herein, the term "gene" refers to an assembly of nucleotides that encode a polypeptide, and includes cDNA and genomic DNA nucleic acids.

A gene encoding a mutant STAT protein, whether genomic DNA or cDNA, can be isolated from any source, particularly from a human cDNA or genomic library, and mutated according to standard methods. Specific cDNA sequences encoding STAT proteins are disclosed in SEQ ID NOS:1, 3, 5, 7, 9, and 11. Methods for obtaining the STAT gene are well known in the art, as described above (see, e.g., Sambrook et al., 1989, supra). Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44: 177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

Accordingly, any animal cell potentially can serve as the nucleic acid source for the molecular cloning of a STAT gene. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

The nucleotide sequence coding for a mutant STAT protein, can be inserted into an appropriate expression vector, i.e., a vector which contains the necessary elements for the transcription and translation of the inserted protein-coding sequence. Such elements are termed herein a "promoter." Thus, the nucleic acid encoding the mutant STAT protein of the invention is operatively associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding a STAT and/or its flanking regions.

In another embodiment, a chimeric STAT protein or mutant STAT protein can be prepared, e.g., a glutathione-S-transferase (GST) fusion protein, a maltose-binding (MBP) protein fusion protein, or a poly-histidine-tagged fusion protein, for expression in bacteria. Expression of a STAT protein as a fusion protein can facilitate stable expression, or allow for purification based on the properties of the fusion partner. For example, GST binds glutathione conjugated to a solid support matrix, MBP binds to a reallose matrix, and poly-histidine chelates to a Ni-chelation support matrix. The fusion protein can be eluted from the specific matrix with appropriate buffers, or by treating with a protease specific for a cleavage site usually engineered between the STAT polypeptide and the fusion partner (e.g., GST, MBP, or poly-His). Furthermore, the present invention contemplates fusions between a domain from one STAT protein in the site of the corresponding domain of a second STAT protein. Such chimeric constructs are specifically exemplified in the Examples, infra.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant mutant or chimeric STAT of the invention, or functional fragment, derivative or analog thereof, may be expressed chromosomally, after integration of the protein coding sequence by recombination. In this regard, any of a number of amplification systems may be used to achieve high levels of stable gene expression (See Sambrook et al., 1989, supra).

The cell into which the recombinant vector comprising the nucleic acid encoding the mutant or chimeric STAT is cultured in an appropriate cell culture medium under conditions that provide for expression of the protein by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DIqA and synthetic techniques and in vivo recombination (genetic recombination).

Expression of a protein may be controlled by any promoter/enhancer element known in the art, but these regulatory elements must be functional in the host selected for expression. Promoters which may be used to control gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thyroidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartrout et al., Canadian Patent Application No. 2,012,311, filed Mar. 15, 1990).

In one embodiment, a gene encoding a mutant STAT protein is introduced in vivo in a vital vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, a particular locus, e.g., the organ implicated in the rejection episode, can be specifically targeted with the vector. Examples of particular vectors include, but are not limited to, a defective herpes virus 1 (HSV1) vector (Kaplitt et al., 1991, Molec. Cell. Neurosci. 2:320-30), an attenuated adenovirus vector, such as the vector described by Stratford-Perricaudet et al. (1992, J. Clin. Invest. 90:626–630), and a defective adeno-associated virus vector (Samulski et al., 1987, J. Virol. 61:3096–3101; Samulski et al., 1989, J. Virol. 63:3822-3828).

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a protein (Felgner, et. al., 1987, Proc. Natl. Acad. Sci. U.S.A. 84:7413–7417; see Mackey, et al., 1988, Proc. Natl. Acad. Sci. U.S.A. 85:8027–8031)). The use of cationic lipids may promote encapsulation of negatively charged nucleic acids, and also promote fusion with negatively charged cell membranes (Felgner and Ringold, 1989, Science 337:387–388). The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancrease, liver, kidney, and the brain. Lipids may be chemically coupled to other molecules for the purpose of targeting (see Mackey, et. at., 1988, supra). Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., Wu et al., 1992, J. Biol. Chem. 267:963–967; Wu and Wu, 1988, J. Biol. Chem. 263: 14621–14624; Hartrout et al., Canadian Patent Application No. 2,012,311, filed Mar. 15, 1990).

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of recognition factor binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The therapeutic compositions may further include an effective amount of the factor/factor synthesis promoter antagonist or analog thereof, and one or more of the following active ingredients: an antibiotic, asteroid. Exemplary formulations are well known in the art, e.g., as disclosed in International Patent Publication WO 93/19179.

An assay useful and contemplated in accordance with the present invention is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agohist for the receptor, the ligand will complex with the receptor, and the resulting complex will bind the response element and inittiate transcription of the luciferase gene. The resulting chemiluminescence is then measured photometrically, and dose response curves are obtained and compared to those of known ligands. The foregoing protocol is described in detail in U.S. Pat. No. 4,981,784 and PCT International Publication No. WO 88/03168, for which purpose the artisan is referred.

In a further embodiment of this ivention, commercial test kits suitable for use by a medical specialist may be prepared to determine the presence or absence of predetermined transcriptional activity or predetermined transcriptional activity capability in suspected target cells, as set forth above. In accordance with the testing techniques discussed above, one class of such kits will contain at least a reagent capable of specifically binding to the receptor STAT protein, and means for detecting binding of the reagent to a STAT protein. Preferably, a specific binding reagent specific for phosphotyrosine, and a second specific binding reagent specific for phosphoserine, are used. In a specific aspect, such a reagent is an antibody. Means for detecting binding may be a label on the antibody (labels have been described above), or a label on a STAT protein or fragment thereof. The kits may also contain peripheral reagents such as buffers, stabilizers, etc.

The present invention may be better understood by reference to the following Examples, which are provided by way of exemplification and not limitation.

EXAMPLE 1

Functionally Active Regions of Signal Transducer and Activator of Transcription (Stat) Proteins Stat1 and Stat3 are two members of the ligand-activated transcription factor family that serve the dual functions of signal transducers and activators of transcription. While the two proteins select similar (but not identical) optimum binding sites from random oligonucleotides, differences in their binding affinity were readily apparent with natural STAT binding sites. To take advantage of these different affinities, chimeric Stat1:Stat3 molecules were used to locate the amino acids that could discriminate a general binding site from a specific binding site. The amino acids between residues ~400 and ~500 of these ~750 amino acid long proteins determine the DNA binding site specificity. Mutations within this region result in Stat proteins which are activated normally by tyrosine phosphorylation and which dimerize, but have greatly reduced DNA binding affinities.

Methods

Cell Culture, Cytokines, and Antisera. Human U3A cells, HepG2 cells, and COS-1 cells were maintained in DMEM supplemented with 10% bovine calf serum. Transfection of cells and selection of stable cell lines were carried out by standard procedures (Shuai et al., 1993, Science 261:1744). Treatment of cells with cytokines was for 15 minutes unless otherwise noted. IFN-γ (a gift from Amgen) was used at a concentration of 5 ng/ml, IFN-α was used at a concentration of 500 I.U./ml. IL-6 (UBI) was used at a concentration of 30 ng/ml. EGF was used at 50 ng/ml. Cytoplasmic and nuclear extracts were prepared as described (Sadowski and Gilman, 1993, Nature 362:79). For immunoprecipitation of cell extracts, Stat1 or Stat3 carboxyl terminal antiserum was used at a 1:200 dilution. Immobilized FLAG-specific monoclonal antibody was used for precipitation according to the manufacturer's instructions (Kodak). Phosphotyrosine-specific monoclonal antibody PY20 was used at 1:2000 dilution according to the manufacturer's instructions (Transduction Laboratories).

Plasmid Construction. Expression plasmid pRcCMV (Invitrogen) carrying Stat1 or Stat3 cDNA (Improta et al., 1994, Proc. Natl. Acad. Sci. USA 91:4776; Zhong et al., 1994, Science 264:95) was used for all cell lines. All of the recombinant STAT proteins were constructed by PCR amplification using Vent Polymerase (NEB) and verified by DNA sequencing. The chimeric Stat1 and Stat3 cDNAs included the FLAG epitope [Kodak IBI; (Hopp et al., 1988, Bio/Technology 6:1204)] to easily identify the recombinant proteins.

Electrophoretic Mobility Shift Assay. Gel mobility shift assays were carried out as described (Levy et al, 1989, Genes & Devel. 3:1362). Double stranded oligonucleotide probes were synthesized for use as the probe with 5'-GATC protruding ends. Probe sequences used in this study are:

| | | |
|---|---|---|
| SIE: | 5'-CAGTTCCCGTCAATCAT-3' | (SEQ ID NO: 19) |
| M67: | 5'-CATTTCCCGTAAATCAT-3' | (SEQ ID NO: 20) |
| Ly6E: | 5'-ATATTCCTGTAAGTGAT-3' | (SEQ ID NO: 21) |
| GRR: | 5'-GTATTTCCCAGAAAAGG-3' | (SEQ ID NO: 22) |
| S1: | 5'-GTTGTTCCGGGAAAATT-3' | (SEQ ID NO: 23) |
| S3: | 5'-TATTTCCGGGAAATCCC-3' | (SEQ ID NO: 24) |

Binding Site Selection. In vitro, binding site selection for Stat1 was carried out essentially according to the method of Pollock and Triesman. IFN-γ treated BUD 8 fibroblast nuclear extracts were mixed with a double stranded random 176 base oligomer and immunoprecipitated with antiserum specific for Stat1 and protein A agarose. The co-purifying DNA was isolated, amplified by polymerase chain reaction, and analyzed for binding by EMSa. Following five rounds of selection, Stat-specific complex was observed, eluted from the gel, and subcloned. To obtain the Stat3 optimum site, nuclear extracts from EGF-treated COS 1 cells transfected with Stat3 expression vector were bound to the random oligomer and applied to an EMSA gel. The region corresponding to the mobility of the Stat3 gel shift on one of the 76 bp Stat1-selected sites was excised and the DNA amplified by PCR. Following 5 rounds of selection from the gel, the resulting complex was supershifted by Stat3 specific antiserum and the DNA isolated from the supershifted complex eluted from the gel, amplified and subcloned.

Results

In vitro binding site selection for Stat1 and Stat3. To determine whether Stat1 and Stat3 homodirects preferred different high affinity oligonucleotide binding sites, we carried out synthesis of a set of deoxyoligonucleotides 76 bases long: a random stretch of 26 bases was sandwiched between two constant 25 oligonucleotide regions that could be used as PCR primers. Stat1 optimum binding sites were determined first. Stat1 activation was carried out by IFN-τ treatment of Bud-8 fibroblast cells and total cell extracts were exposed to the random deoxyoligonucleotide mixture. Stat1 COOH-terminal antiserum (Schindler et al., Science 257:809–815) was used to immunoprecipitate the protein/DNA complexes followed by PCR amplification of the DNA in the precipitate (Pollock and Triesman, 1990, Nucl. Acids Res. 18:6197–6204). Five such cycles were carried out and individual DNA segments were cloned after the final amplification. Sequencing of 55 individual clones demonstrated a clear consensus binding site with strong similarity to the earlier identified GAS elements (Decker et al., 1991, EMBO J. 10:927–932; Lew et al., 1991, Mol. Cell. Biol. 11:182–191; Darnell et al., 1994, Science 264: 1415–1421; FIG. 1A]. The most prominent feature of the selected sequence was a 9 base pair inverted repeat with TTCCC/G as the half site consensus, a feature consistent with the fact that Stat1 binds DNA as a dimer (Shuai et al., 1994, Cell 76:821–828). The symmetry around the central C or G [designated position zero] is also reflected in the flanking sequence by a strong preference for A at position −6 and T at +6. There was also a preference at position +7 for a G but position −7 did not show a preference suggesting that the flanking sequences surrounding the core sequence may contribute to ptimum binding.

Figure 1B:
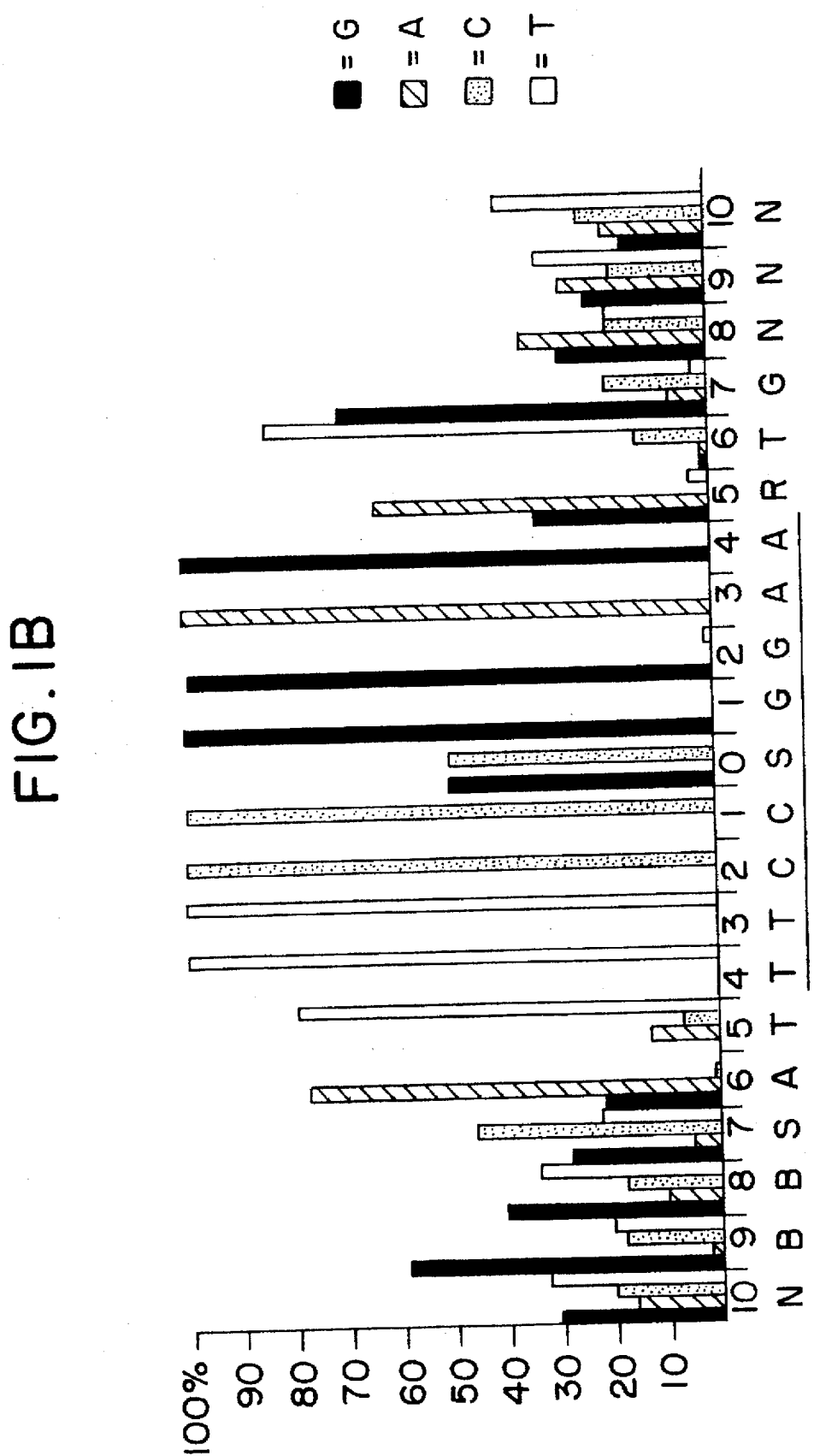
Figure 1C:
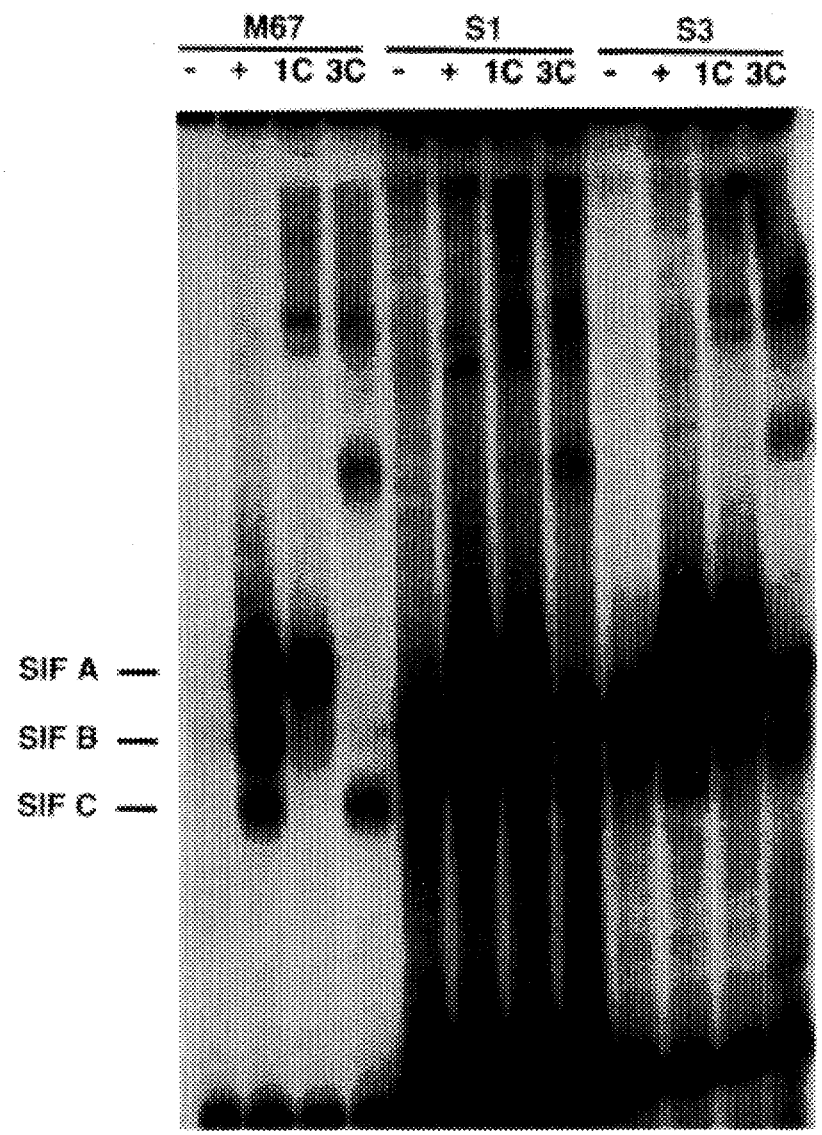

A double-stranded deoxyoligonucleotide of 22 base pairs containing in its center the consensus core sequence (TTCCCGGAA) (SEQ ID NO:25) was synthesized and used as probe in the electrophoretic mobility shift assay (EMSA) (Fried and Crothers, 1981, Nucl. Acids Res. 9:6505–6525); Levy et al., Genes & Devel. 3:1362–1372; FIG. 1B). Extracts were used from both IFN-τ treated HepG2 cells and HepG2 cells treated with a high dose of IL-6 which induces three well recognized bands (Sadowski et al., 1993, Nature 362:79–83) described as SIF A, SIF B, and SIF C because there are three DNA binding complexes inducible by medium from cells expressing the sis oncogene (SIE, sis-inducible element; SIF, sis-inducible factor (Wagner et al., EMBO, 1990, EMBO J. 9:4477–4484). The SIF C complex is identical in mobility and protein content to the IFN-τ induced complex (Sadowski et al., 1993, Science 261:1739–1744) and is therefore a Stat1 homodimer. This complex reacts with Stat1 specific antiserum. The SIF A complex which migrates more slowly (most likely due to a greater number of positively charged amino acids in addition to a slightly longer polypeptide chain) reacts with the Stat3 antiserum (Zhong et al., 1994, Science 264:95–98) and is considered to contain a Stat3 homodimer. The SIF B complex which migrates between complex A and C reacts with both Stat1 and Stat3 antisera is considered a Stat1:3 heterodimer. [These earlier conclusions are supported by results in FIG. 1b, lanes 1–4 with synthetic oligonucleotide M67 (Wagner et al., 1990, EMBO J. 9:4477–4484) as the labeled DNA probe.] The Stat1 selected consensus oligonucleotide bound weakly to some protein in untreated cells (lane 5, FIG. 1b) but also bound strongly to the induced STAT proteins that form SIF A, B and C. Thus, it seemed possible there would be overlap of the Stat1 optimum binding site and any Stat3 response element.

To determine the optimum binding site for Stat3, extracts were used that contained high levels of activated Stat3 with much less Stat1. This was achieved by preparing extracts of EGF-treated, Stat3 transfected COS cells as the source of binding activity (Zhong et al., 1994, Science 264:95–98); the activated Stat3 homodimer bound to the random 76 base pair probe (corresponding to the SIF A band) was identified by electrophoretic separation. The position of SIF A was marked using one of the Stat1-selected 76 nucleotide high affinity sites which binds to Stat3 as shown in FIG. 1B. The gel electrophoretic band was excised, DNA amplified and five cycles of gel shifts and amplification were carried out before cloning of individual examples of DNA, from the SIF A complex. Sequencing of 55 individual clones with Stat3 selected sequences also revealed a clear consensus sequence which was identical in the core sequence TYCC[C or G]GGAA to that selected by the Stat1 (FIG. 1A). Just as did the Stat1 site, the Stat3 selected site contained an A or T at positions +6 or −6, respectively, but in addition the Stat3 site also showed a strong preference of A and T at positions +5 and −5 making a 13 nucleotide palindrome the favored Stat3 site. As with Stat1, a preference for G at position +7 was not matched by a C at position −7. Also, position −9 was G in about 60% of cases. As with Stat1, these flanking sequence preferences may contribute to the optimum site.

An oligonucleotide probe was synthesized to represent the Stat3 optimal site (position −9 to +9) and used in a gel shift experiment (FIG. 1B, lanes 9–13). Since the Stat1 optimum site core is contained within the Stat3 probe, it was not surprising that, like the selected Stat1 probe, the Stat3 probe bound well to all of the SIF complexes. Unfortunately, the Stat3 consensus probe used also bound even more strongly to a constitutively active protein (marked by the asterisk in FIG. 1B) that comigrates closely with SIF B, obscuring the center section of the gel shift pattern. It was noted that the Stat3 consensus probe bound somewhat better in the SIF A complex from which it had been selected than did the Stat1 optimum probe, but this was estimated by competition experiments to be only a 3–5 fold difference. While it is clear that such relatively minor differences might be important at individual sites in genomic DNA, we could not use these "consensus" probes to easily distinguish the binding affinities of Stat1 from Stat3.

Figure 2:
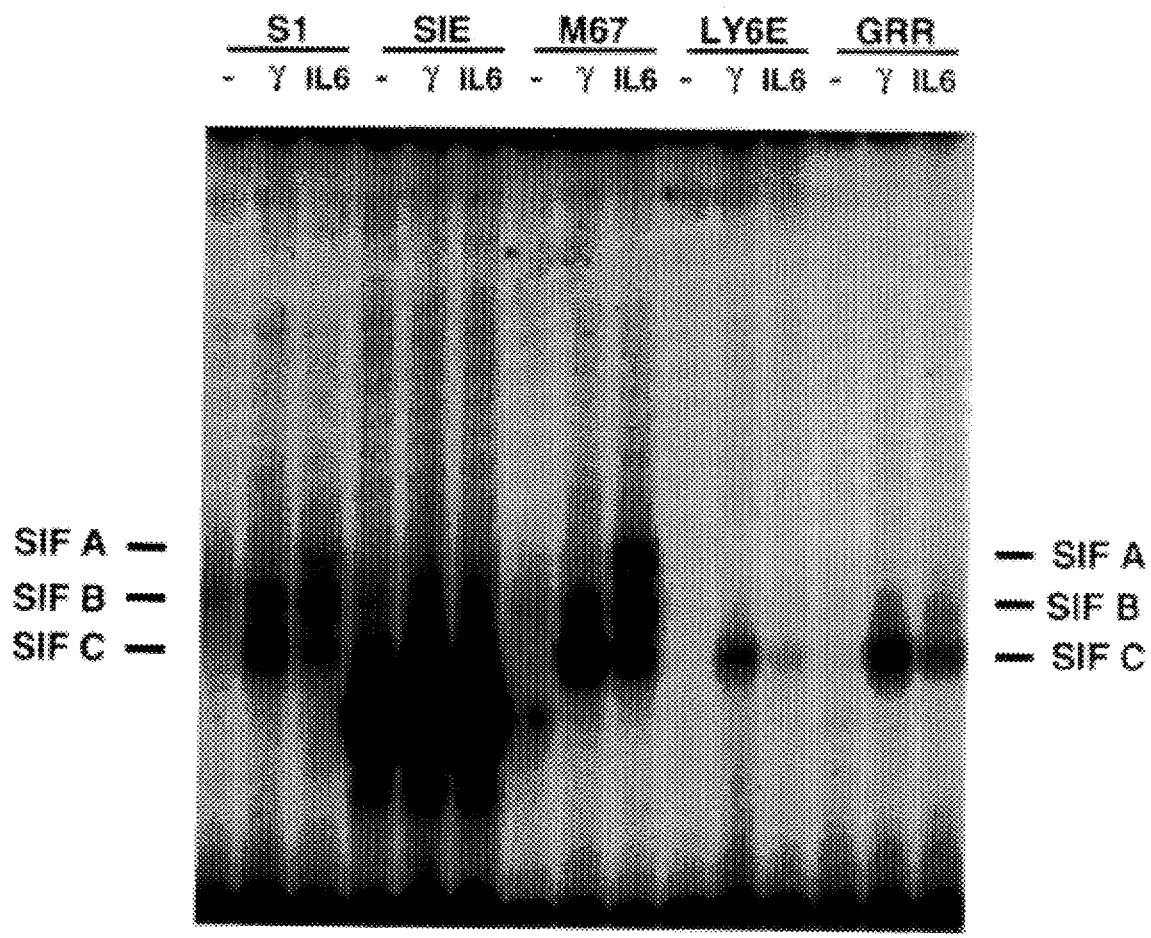
FIG. 2 Binding of Stat1 and Stat3 to known GAS Elements Reveals Differential Binding Patterns. Nuclear extracts from untreated (−), IFN-γ treated (γ), and IL-6 treated HepG2 cells were incubated with the indicated probes and DNA protein complexes detected by EMSA. Positions of SIF A, SIF B, and SIF C are marked. S1=Stat1 selected consensus sequence. SIE=cfos promoter sis-inducible element. M67=hyperactive mutated form of SIE. Ly6E=GAS element from the Ly6E gene promoter. GRR= FcγR1 promoter IFN-γ response element.

Stat protein binding to natural sites. Previously identified Stat protein binding elements were next examined to determine if any sites gave sufficient specificity to distinguish easily Stat1 from Stat3 binding. Oligonucleotide probes representing GAS [IFN-τ activates sites (Decker et al., 1991, EMBO J. 10:927–932; Lew et al., 1991, Mol. Cell. Biol. 11:182–191) from the murine surface antigen Ly6e (Kahn et al., 1993, Proc. Natl. Acad. Sci. USA 90:6806–6810), IFN-τ response region (the GRR) of the FcgR1 gene (Pearse et al., 1993, Proc. Natl. Acad. Sci. USA 90:4314–4318), the c-fos SIE and its high affinity mutated form, M67 (Wagner et al., 1990, EMBO J. 9:4477–4484 1993), and the optimum Stat1 or Stat3 binding sites (FIG. 2). Using extracts from HepG2 cells treated with IL-6 that contain SIF A, SIF B and SIF C binding activity, differences were clearly observed among these probes. The M67 SIE bound probes to form in near equimolar amounts the SIF A, SIF B and SIF C complexes while the natural c-fos site gave a very weak signal with STAT proteins. The Stat1 optimum core sequence was also bound by all of the SIF species, but with overall lower affinity as judged by the intensity of the binding signal. Thus, the M67 probe binds well to both Stat1 or Stat3 but cannot distinguish between them. In contrast, the GRR and Ly6e probes were both bound by the SIF C protein (Stat1 homodimer), with the GRR probe giving 2–3 fold more binding than the Ly6e probe. Both probes were bound poorly by the SIF B complex, the heterodimer of Stat3 and Stat1. Most significantly, the SIF A complex that represents Stat3 homodimer binding was not observed with the GRR or Ly6e probes unless the autoradiograms were overexposed. Thus, the two closely related proteins Stat3 and Stat1 differ in their ability to recognize these two natural GAS elements. Other GAS elements tested (from the IRF1 gene, the alpha-2 macroglobulin gene, the gunnylate binding protein gene, and the B-casein gene) displayed intermediate binding properties with respect to Stat1 and Stat3 binding and were not useful for this analysis (data not shown).

Localization of specific DNA binding region of Stat proteins. We proceeded to use the differential binding affinities of Stat1 and Stat3 to the GRR compared to uniform binding to the M67 SIE probe in determining the STAT protein region that discriminates between the probes. The Stat1-SH2 group lies between amino acids 573 and 700 (resides ~6600–700) (Fu, 1992, Cell 70:323–335; Schindler et al., 1992, Proc. Natl. Acad. Sci. USA 89:7836–7839; Schindler et al., 1992, Science 257:809–815) and the Y that becomes phosphorylated is at residue 701. Mutations at the Y701 and in R602 in the pocket of Stat1-SH2 have proved the necessity of these regions in STAT tyrosine phosphorylation and subsequent activation as a DNA binding protein (Shuai et al., 1993, Science 261:1744–1746; Shuai et al., 1993, Nature 366:580–583; Shuai et al., 1994, Cell 76:821–828). Moreover, the -SH2 region of Stat1 has been shown to confer IFN-τ inducibility on Stat2 (Heim et al., 1994, Science, in press). Thus, a chimeric protein with the Stat1 —COOH terminus can be activated by IFN-τ. Stat3 also contains an SH2 region from ~60–700 and a Y in a position comparable to Stat1 at residue 705 but Stat3 is not activated by IFN-τ (Zhong et al., 1994, Proc. Natl. Acad. Sci. USA 91:4806–4810). Mutations of the Stat3 Y residue at 705 to phenylalanine likewise blocks phosphorylation of Stat3, Z. Wen and J. E. Darnell, unpublished observations).

Figure 3:
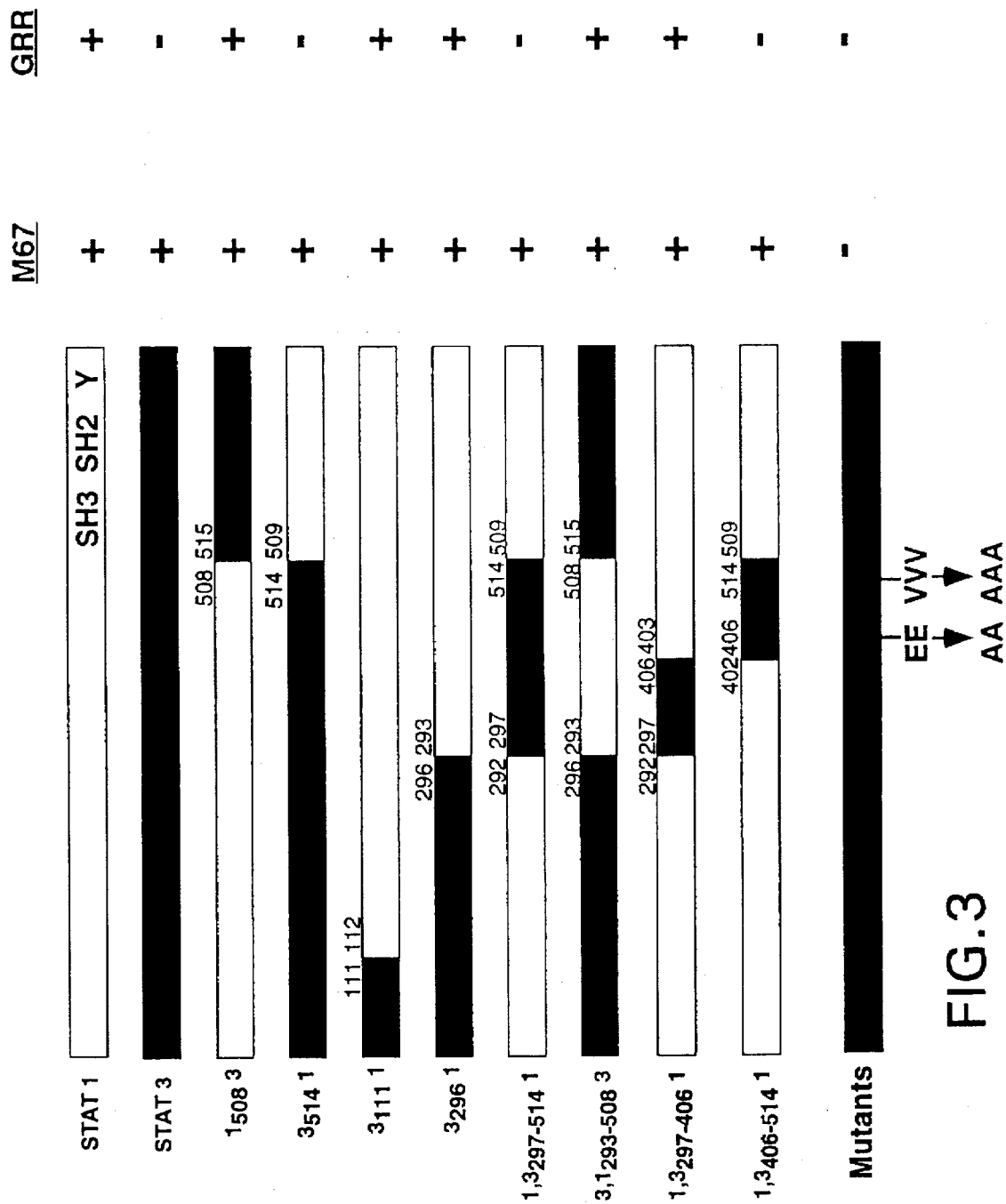
FIG. 3 Diagrammatic Representation of the Stat1/Stat3 Chimeras used in this Study. Open box depicts the Stat1 molecule and the black box depicts Stat3. The numbers above the boxes refer to the amino acid residues of Stat1 or Stat3 before and after the chimerio junction. Positions of the src hornology domains (SH3, SH2) and activating tyrosine (Y) are indicated for Stat 1. Binding properties for the M67 and GRR oligodeoxynucleotides as determined in this study (see FIG. 4) are indicated to the right. The bottom box depicts the positions of the two mutations made in Stat3 (see FIG. 5). Drawn to approximate scale.

As the segment of STAT proteins from ~600 to ~750 appear to function in activation and dimerization, we focused on the $NJ_2$ terminal regions as a possible source of DNA binding specificity. Gene fusions were constructed which code for chimeric Stat proteins containing regions of Stat1 fused to Stat3 or vice versa (FIG. 3). The chimeras are named to specify the source of the fused Stat protein from NH2 to COOH terminus with the amino acid number of the joint in subscript. For example, [1]500[3] means Stat1 amino acids 1–500 joined to Stat3 at amino acid 500. The cDNAs were transfected into U3A cells and permanent cell lines expressing the recombinant proteins were selected. U3A cells lack expression of Stat1 protein, but contain active receptors for IFN-τ or IFN-α (Pellegrini et al., Mol. Cell. Biol. 9:4605–4612; Muller et al., 1993, EMBO J. 12:4221–4228).

Stat1 (and chimeric proteins containing the Stat1 carboxyl terminal activation regions) introduced into this cell line can be activated by IFN-τ or IFN-α (Muller et al., 1993, EMBO J. 12:4221–4228; Improta et al., 1994, Proc. Natl. Acad. Sci.

USA 91:4776–4780; FIG. 4). Stat3 can be activated by IFN-α in the U3A precursor cell line, 2FTGH (I. Kerr, personal comm.; C. M. Horvath, Z. Zhong and J. E. Darnell, Jr., unpublished observations), but we found that the U3A cells derived from 2FTGH by extensive mutagenesis (Pellegrini et al., 1989, Mol. Cell. Biol. 9:4605–4612) did not respond by activating the endogenous Stat3. However, the wild type Stat3 permanently introduced into U3A cells was activated by IFN-α (FIG. 3, last lane) (C. M. Horvath and J. E. Darnell, Jr., unpublished observations). Therefore, we used IFN-α to activate in U3A derived cell lines the chimeric proteins containing the Stat3 carboxyl terminal activation regions.

Figure 4A:
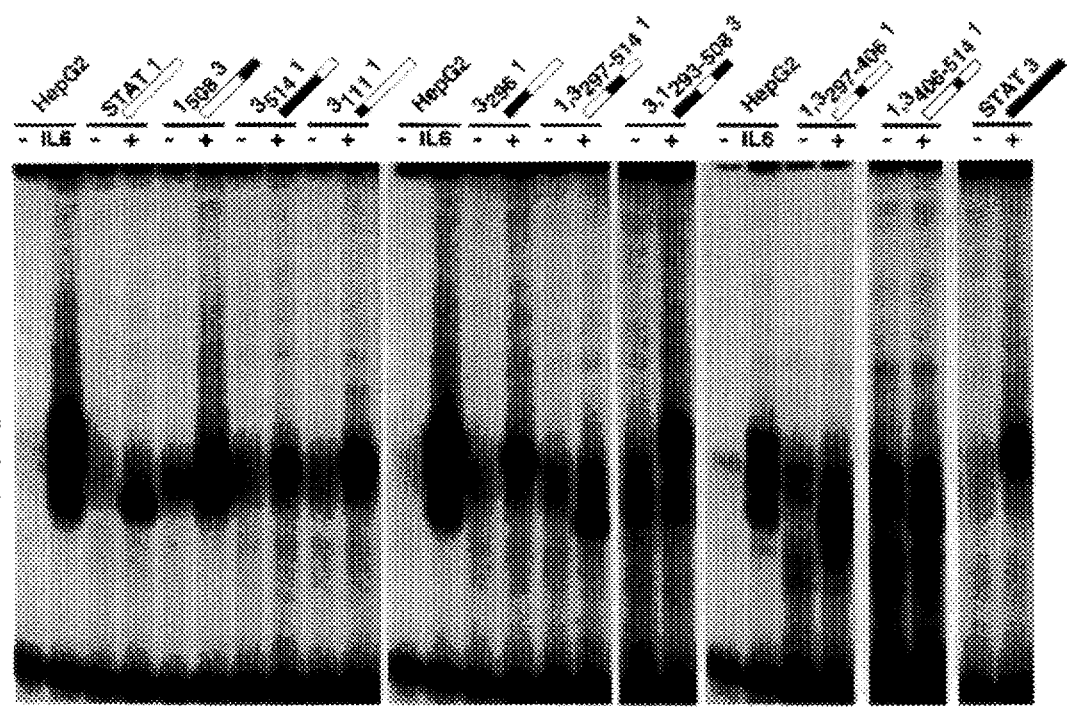
FIGS. 4A–4B Differential Binding of the Chimeric STAT Proteins. Nuclear extracts from untreated (−) and interferon treated (+) U3A cells expressing the chimeric STAT proteins were incubated with M67 probe to reveal all DNA binding complexes (FIG. 4A). Positions of SIF A, SIF B, and SIF C are marked as determined from IL6-treated HepG2 cell nuclear extracts. The same extracts incubated with GRR probe (FIG. 4B). The position of SIF C from IL6-treated HepG2 cell nuclear extracts is marked, and the position where SIF A and SIF B would migrate are marked in parentheses.

Consistent with the results using IL-6 treated HepG2 extracts (FIG. 1B), extracts of U3A cells permanently transfected with either Stat1 and treated with IFN-τ or transfected with Stat3 and treated with IFN-α, displayed the same differential DNA binding properties as did the same proteins activated in HepG2 cells (FIG. 4). Activated Stat1 binds well to both M67 and GRR p robes, while activated Stat3 binds to M67 but not (or very poorly) to the GRR (FIGS. 4A and B, lanes 4 and 26). Chimerio junctions in the first ~500 amino acids were chosen based on regions of amino acid sequence identity between Stat1 and Stat3 so as not to disrupt potentially important domains of the resulting hybrid proteins. As mentioned earlier, a greater number of glutamine and aspartic acid residues plus a slightly greater length in Stat3 compared to Stat1 is the cause for the slower migration of Stat3 homodimers compared to Stat1 homodimers. In chimerio proteins, these differences were reflected in protein:DNA complexes that migrated at intermediate rates. A chimeric Stat protein containing the first 508 amino acids of Stat1 and the carboxyl terminus of Stat3 exhibited the general binding property of Stat1 in that the chimerio protein, designated $^1508^3$, bound well to both test probes and migrated just slightly slower than Stat1 (FIGS. 4A and B, lane 6). The complementary chimera, $^3514^1$ with the amino terminal 514 amino acids of Stat3 fused to the carboxyl terminus of Stat1 had the recognition property of Stat3, that is, it bound well to M67 probe, but not to GRR (FIGS. 4A and B, lane 8). Thus, the STAT DNA recognition capacity was localized to the amino terminal 508 amino acids of Stat1 or 514 amino acids of Stat3, and was not influenced by the putative SH3 domain (~500–600), the SH2 domain (~600–700) or other sequences in the carboxyl terminal third of the molecule which itself can utilize different ligand-receptor complexes for activation (IFN-τ for Stat1 and IFN-α for Stat3).

Figure 4B:
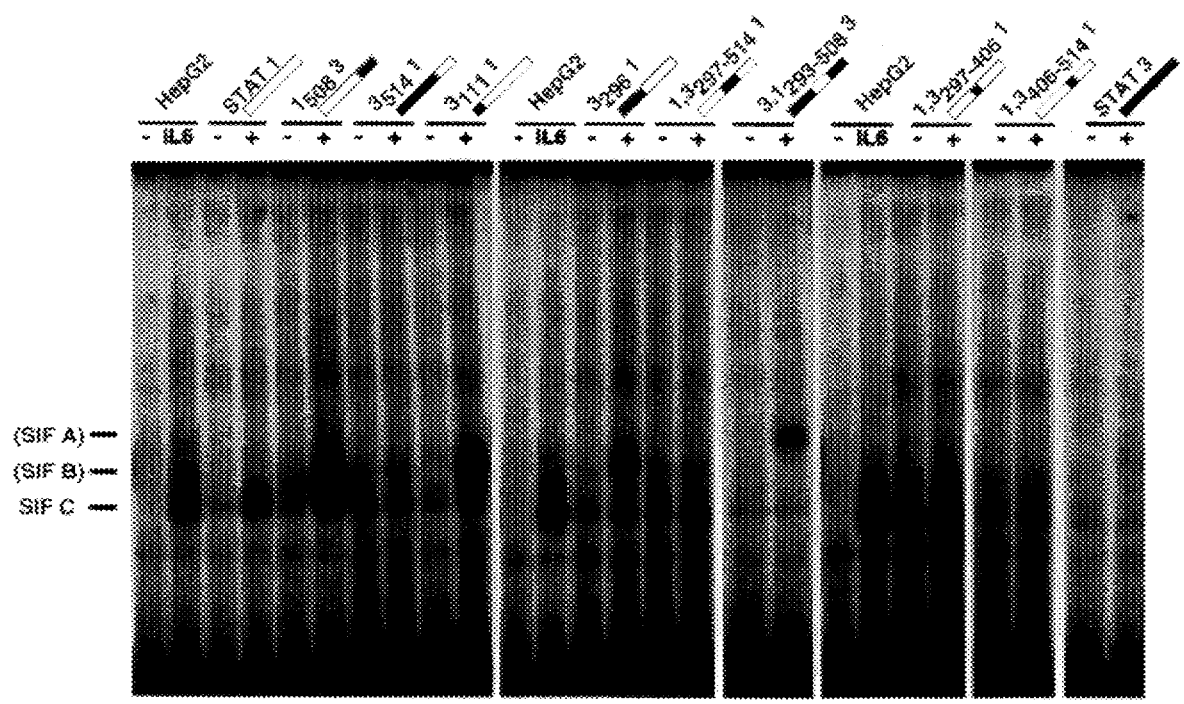

To further dissect the STAT DNA recognition region, additional chimeras were constructed containing the amino terminal 111 or 296 amino acids of Stat3 substituted into Stat 1. Both recombinant molecules, $^3111^1$ or $^3296^1$, retained the binding characteristic of Stat1 (FIGS. 4A and B, lanes 10 and 14). recognizing both M67 and GRR probes. These results suggest that the amino terminal 296 amino acids do not determine the specificity of DNA sequence recognition. It seemed reasonable to infer from this set of chimeras that the region from amino acid 297 to 514 of Stat3 (or 508 of Stat1) imparted the ability to discriminate between DNA elements. To test this suggestion directly, the region of Stat1 between 292 and 509 was replaced with the Stat3 amino acids 297 to 514 (chimera $^{1,3}297,514,^1$) and a corresponding Stat3 with a Stat1 insertion, chimera $^{1,3}297-514,^1$ molecule showed that while the amino acid sequence was primarily Stat1, the recombinant molecule now bound M67 but failed to bind the GRR showing that recognition capacity of Stat3 was transferred to Stat1. Reciprocally, when chimera $^{3,1}293-508,^3$ was tested, the recombinant, largely Stat3 sequence could now bind well to both the M67 and GRR probes, transferring the DNA binding property of Stat1 (FIGS. 4A and B, lanes 16 and 18). We concluded that the portion of the STAT protein which recognizes the DNA response element lies between amino acids 297 and 514 of Stat3 and between amino acids 293 and 508 of Stat1. A final set of chimeric molecules that more accurately positioned the Stat3 recognition capacity was then constructed. The 200 amino acid region was divided into two approximately 100 amino acid insertions of Stat3 into Stat1. These chimeras showed that amino acids 297 to 406 left Stat1 recognition intact while insertions of amino acids 406 to 514 resulted in the transfer of Stat3 recognition (FIGS. 4A and 4B, lanes 22 and 24). We conclude that the amino acids that determine DNA binding specificity lie in this approximately 108 amino acid segment between residues 406 and 514.

Figure 5A:
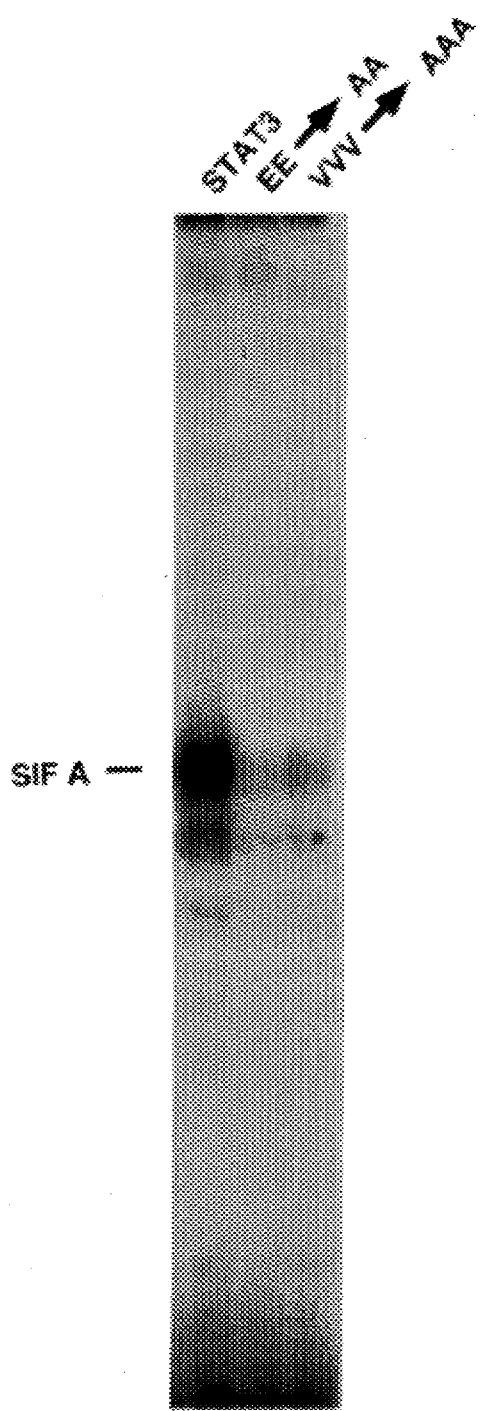
FIGS. 5A–5C Mutations in Stat3 influence DNA Binding Affinity.
Figure 5B:
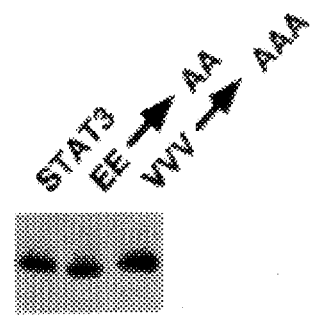
Figure 5C:
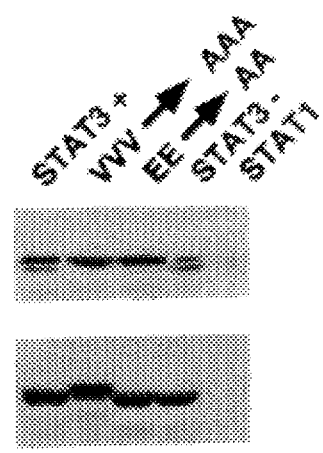

Point mutations alter DNA binding affinity. The proposed DNA recognition domain (~400–500) encompasses one of the most highly conserved regions of the STAT protein family, although no function had been previously assigned to this region either from experiment or from sequence comparison with other proteins in the data banks. To ascertain if specific amino acids within the conserved amino acid stretches were important for binding to DNA, mutations with highly conserved the highly conserved regions of Stat3 in the ~400–500 region. The sequence VTEEL (residues 432 to 436) was changed to VTAAL (mutant EE>AA) or the conserved sequence SLPVVVISN (residues 458 to 466) was changed to SLPAAAISN (mutant VVV>AAA). Each mutant protein was expressed transiently in COS-1 cells [which have low endogenous Stat3 protein level (Zhong et al., 1994, Science 264:95–98) and nuclear extracts prepared following activation with EGF. Neither of the two mutants produced STAT proteins capable of binding the M67 element to the same extent as wild type STAT 3, suggesting that both mutations influenced DNA recognition. Mutant EE>AA had a more severe effect on DNA binding (nearly undetectable) than mutant VV>AA, which exhibited a distinctly reduced but still detectable binding (FIG. 5A). To determine whether these mutations blocked activation of the protein, Stat3 antiserum was used to precipitate proteins from the same COS cell extracts and the precipitates were tested by immunoblotting with antiphosphotyrosine antibody. Both mutant proteins were phosphorylated as well as the wild type protein (FIG. 5B). To determine if the mutant STAT proteins were capable of dimerization, the mutant EE>AA or mutant VVV>AAA were tagged with a FLAG epitope (Hopp et al., 1988, Bio/Technology 6:1204–1210) so that they could be distinguished from endogenous STAT 3 and transfected into COS cells along with non-tagged Stat1 cDNA. Extracts of the COS cells treated with EGF were then precipitated with monoclonal antibody to the FLAG epitope (M2). If dimerization occurred the FLAG tagged protein should carry along both endogenous and transfected activated Stat1 protein in heterodimers into the precipitate. FIG. 5C shows clearly that this was the case; Stat1 was detected in all FLAG-containing extracts, but not in control cells transferred with Stat1 alone. A small amount of Stat1 coprecipitated with FLAG-Stat3 from untreated COS cells, reflecting a low basal level of Stat3 activation. The amount of Stat1 from the treated cells was from about 5-fold greater than from the untreated cells, indicating a ligand-induced heterodimerization. These data support the conclusion that the mutant EE>AA and VVV>AAA proteins become phosphorylated in response to ligand and dimerize but cannot bind DNA as well as wild type Stat3. These results greatly strengthen the conclusion that this highly conserved region of the STAT proteins between 406 and 514 participate in recognition of and binding to GAS-like DNA response elements.

Discussion

In the past two years a large number of reports have indicated that sequences of the general motif TTNCNNNAA, the originally defined GAS consensus, can be used to detect activated STAT DNA binding (Lew et al., 1989, Mol. Cell. Biol. 9, 5404–5411; Kahn et al., 1993, Proc. Natl. Acad. Sci. USA 90:6806–6810; Pearse et al., Proc. Natl. Acad. Sci. USA 90:4314–4318; Wegenka et al., 1993, Mol. Cell. Biol. 13:276–288). We sought to determine first whether two specific STAT members that are activated by different ligands would select individual binding sites. However, optimum site selection experiments showed that both Stat1 and Stat3 preferred very similar nine base pair core elements and only minor differences in flanking sequences. The selection of highly similar optimum sites is characteristic of other DNA binding protein families such as homeobox protein (Wilson et al., 1993, Genes & Devel. 7:2120–2134), yet it is clear that specific biologic events are controlled by different family members. It is generally believed therefore that optimum binding sites may be used less commonly in evolution but that chromosomal binding sites evolved that are differentially distinguished by particular members of protein families. In line with this conjecture we found that two sites from genes known to be activated by IFN-τ, the GRR of the FcτR1 gene and the GAS site in the promoter of the Ly6e gene are in fact bound by Stat1 homodimers but not by Stat3 homodimers. The high affinity synthetic derivative of the cfos promoter, M67, in contrast is bound by both proteins and served to monitor the binding of either protein. It is interesting to note that the GRR sequence differs from the selected core sequence only at position +1 where A replaces G. Similarly, the Ly6e sequence differs from the M67 probe at only one position within the core (T replaces C at the zero position). Thus, these central nucleotides within the nine base pair are important for Stat3 binding while Stat1 binding is less demanding at these sites.

In fact, most of the genomic DNA sites (Table 1) that presumably function to bind STAT proteins do not contain the perfect nine base palindrome selected by the optimum site selection techniques. Considerable additional work will be required to determine the in vivo binding specificity of chromosomal GAS sites for particular STAT proteins especially since few experiments have yet been reported on the influence of adjacent binding sites for additional transcription factors that may bind coordinately with STAT proteins.

TABLE 1

Comparison of GAS-like Promoter Elements

| Source | Core Element | SEQ ID NO: |
|---|---|---|
| S3 | TTCCGGGAA | 26 |
| S1 | TTCCGGGAA | 27 |
| M67 SIE | TTCCCGTAA | 28 |
| cFOS-SIE | TTCCCGTCA | 29 |
| Ly6E/A | TTCCTGTAA | 30 |
| FcγR1 | TTCCCAGAA | 31 |
| GBP | TTACTCTAA | 32 |
| MIG | TTACTATAA | 33 |
| IFP53 | TTCTCAGAA | 34 |
| ICAM-1 | TTCCCGGAA | 25 |
| IRF1 | TTCCCCGAA | 35 |

TABLE 1-continued

Comparison of GAS-like Promoter Elements

| Source | Core Element | SEQ ID NO: |
|---|---|---|
| ICSBP | TTCTCGGAA | 36 |
| α2 Macroglobulin | TTCCCGTAA | 37 |
| Acid Glycoprotein | TTCCCAGAA | 38 |

The high amino acid sequence identity between Stat1 and Stat3, coupled with the inherent ability of Stat3 to distinguish between M67 and GRR elements, made it possible to define the DNA binding domain of the STAT proteins by exchanging regions between two proteins and assaying the substituted proteins for DNA site binding preference. This technique resulted in identifying residues 406 to 514 as capable of the transfer of binding specificity, since an activated Stat1 molecule containing residues 406 to 514 of Stat3 could bind only to the M67 probe and not the GRR probe while activated Stat1 itself birds to both probes. Within these 108 amino acids, Stat1 and Stat3 have only 43 amino acid differences. Counting conservative amino acid changes the sequences are even more similar. Mutations targeted to the most conserved sequences in this domain have no effect on phosphorylation or dimerization of the STAT proteins, but reduce DNA binding. We conclude that this region of the Stat1 and Stat3 proteins between 406 and 514 controls DNA binding specificity and is likely to be the DNA binding domain. Since the region between 400 and 500 is highly conserved in all the other reported STATs, it seems likely that this region will function for all family members.

In order to suggest any possible folding motifs in the putative DNA binding regions, amino acids in the 293–467 region of all the presently cloned STATs (1–6) were analyzed by computer comparison that predict secondary structure motifs by the algorithm of Chou and Fasman (FIG. 6A–6B; Genetics Computer Group, 1991). The consensus prediction suggests a helical domain surrounding the VTEEL sequence which extends until the SLPVVV sequence which is at the beginning of a predicted beta sheet. Comparison of the possible DNA binding region we define here to known DNA binding domains does not reveal any similarity. Perhaps the STAT protein DNA binding domain will represent an unusual class of DNA binding domain. It is interesting also that this domain lies between the SH3 homology which binds proline rich sequences (Cicchetti et al., 1992, Science 257: 803–806) and the conserved STAT sequence PCMPXXPXXP. If these two sequences interacted within a STAT molecule prior to phosphorylation of the protein, the DNA binding domain might be shielded in the non-phosphorylated protein or conversely such an interaction after phosphorylation might present the putative helical domain.

The exchange of this 108 amino acid domain can substitute the DNA recognition properties of these two STAT proteins. A more direct demonstration that this region is the DNA contact domain would be to transfer this domain to another class of dimeric transcription factors. We have attempted to reconstitute specific DNA recognition by grafting these sequences onto an unrelated dimerization domain from the heterologous bZIP or HLH families. STAT amino acids ~300 to ~500 were joined to the c/EBP leucine zipper and the E47 HLH domains, but demonstration of specific DNA binding by these fusion proteins has been unsuccessful so far. One reason might be that specific structural properties inherent in the STAT family of transcription factors are not provided simply by the dimerization motifs of these other factors. For example, the primary dimerization of the STAT proteins is mediated by intermolecular SH2/phosphotyrosyl interactions (~600–710) which predicts an antiparallel interaction of the two chains in this dimeric region (Shuai et al., 1994, Cell 76:821–828). Perhaps this orientation requires compensation as the chains emerge from the dimer in order to present the residues of the 400–500 region to DNA. ZIP and HLH dimerization domains are parallel with a short hinge region that allows the short DNA contact helices of those proteins to rotate correctly to form "induced sites" on the DNA (Burley, 1994, Current Opin. in Structural Biol. 4:3–11) since the potential STAT DNA contact region has only a limited helical content, it could be that the domain must make a protein fold that has not yet been described in other DNA binding proteins.

EXAMPLE 2

Maximum Stat1α Activation of Genes Requires Phosphorylation on Both Tyrosine-701 and Serine-727

The STAT proteins are latent transcription factors that becomes activated by phosphorylation on tyrosine in response to polypeptide receptor interaction at the cell surface. The activated STATs dimerize, translocate to the cell nucleus and bind DNA. The STAT proteins were originally recognized in studies of interferon alpha (INF-α) and interferon gamma (INF-γ transcriptional activation: Stat1 and Stat2 are phosphorylated in response to INF-α, heterodimerize and together with a 48 kD protein that is not phosphorylated bind to the INF-α-specific DNA element, the ISRE. Stat1, but not Stat2, is activated by INF-γ, homodimerizes, translocates to the nucleus and binds to a different DNA element, the GAS site (INF-γ-activated site). Cell lines (U3 cell) that lack Stat1α and Stat1β, which lacks of the COOH-terminal 38 amino acids of Statα, were defective in response to either INF-α or INF-γ. Cell lines that lack Stat2 were deficient for the INF-α response only. In U3 cells, Stat1α or Stat1β suffice to restore the INF-α pathway. Stat1α can restore the INF-γ pathway but Stat1β cannot despite the fact that Stat1 β is phosphorylated on tyrosine, dimerizes, enters the nucleus and can bind DNA. Since the only difference in Stat1α and 1β is the lack of the COOH terminal 38 amino acids in Stat1β compared to Stat1α, this focused our attention on these residues in IFN-γ-dependent transcriptional activation.

We had earlier encountered some parallels anti some differences in drug sensitivity in the INF-α and INF-γ transcriptional pathways. Both pathways are inhibited by genistein or staurosporine which are primarily inhibitors of tyrosine phosphorylation in line with the obligatory requirement for tyrosine phosphorylation for STAT dimer formation and DNA binding. However, both 6-aminopurine and H7 which are serine/threonine kinase inhibitors blocked INF-γ-induced transcription but had very much less effect on INF-α induced transcription. In addition $^{32}$P is incorporated into phosphoserine in Stat1α to a greater extent than in Stat1β. Based on all of these results, we reasoned that perhaps Stat1α contained a critical serine in the 38 terminal amino acids that served in gene activation.

The present Example demonstrates that serine 727, which is lacking in Stat1β, is in fact phosphorylated, probably constitutively in serum-grown cells. Furthermore, Stat1 protein that is mutant in serine $727^{Ser}727 \rightarrow ^{Ala}727$) is phosphorylated normally on tyrosine, dimerizes and binds DNA, but in cells bearing the mutant protein only about 20 percent as much INF-γ-dependent transcription occurs. Thus, the Stat1 protein requires both phosphorylation on tyrosine and serine to be fully competent in inducing transcription.

Figure 7:
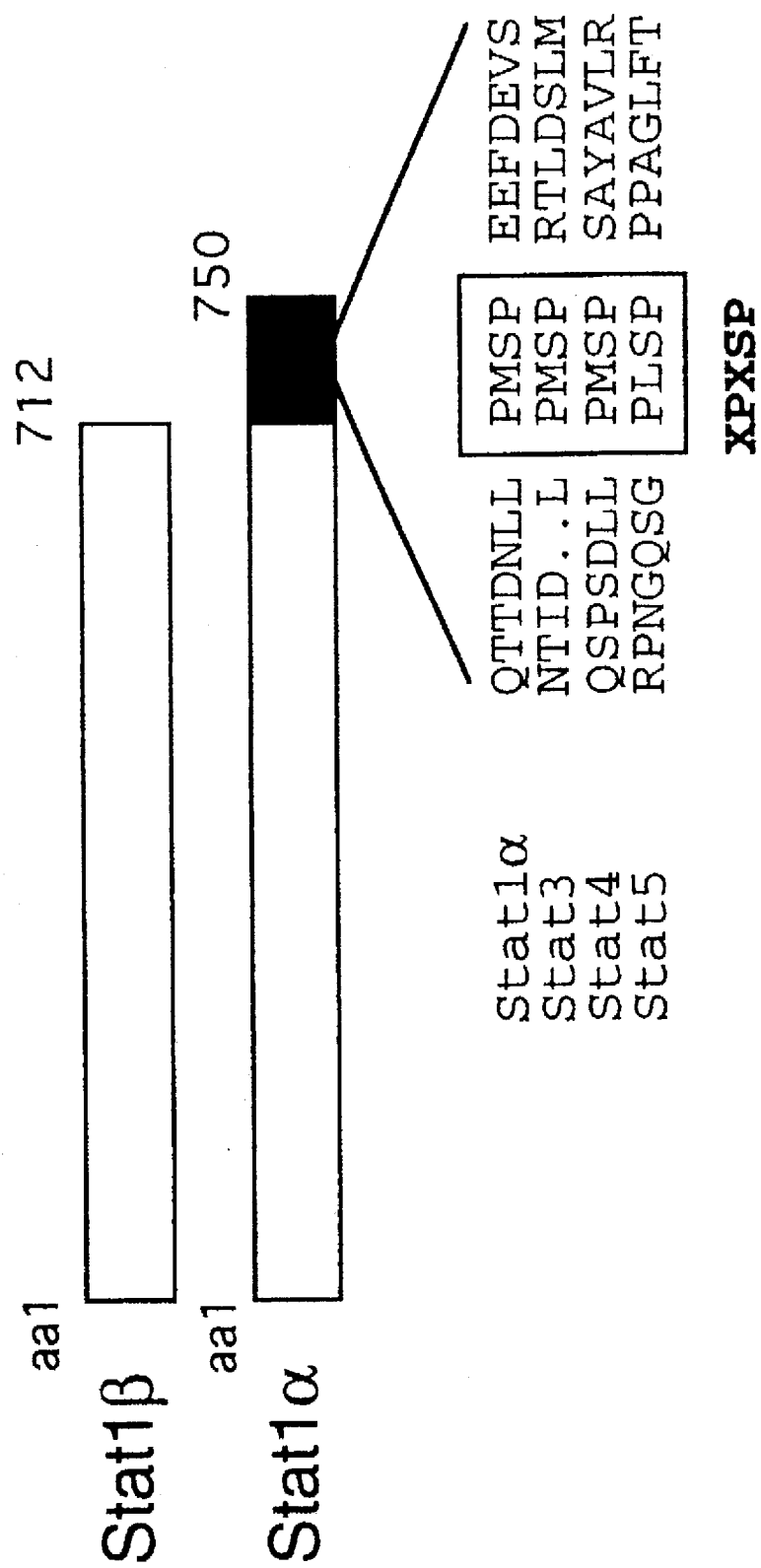
FIG. 7 Comparison of the partial carboxyl terminal sequence in a series of STAT proteins.

Sequence alignment of STATs reveals conserved PMSP box. Amino acids sequence comparison of Stats have revealed that the conserved regions are scattered throughout nearly the entire length of the proteins. However, the COOH-terminal (from about 710 to the end) of the Stats is quite diverse. FIG. 7 compares the partial carboxyl terminal sequence in a series of STAT proteins. Despite the overall diversity within this region, there is a highly conserved sequence PMSP in Stats1α, 3, 4, and 5(PLSP). The conserved sequence is lacking in the Stat1β spliced variant from the Stat1 gene, Stat 2 and 6. This PMSP sequence is known to be at least part of MAP kinase recognition consensus sites.

Figure 8A:
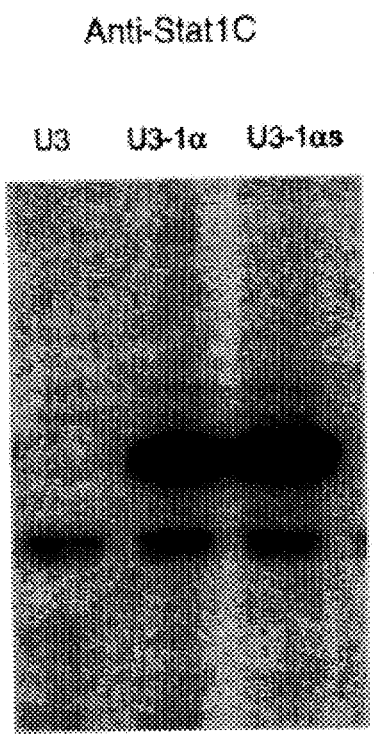
FIGS. 8A–8B Phosphorylation of wild type and mutant proteins on tyrosine as tested by anti-phosphotyrosine antibody reaction with Stat1 immunoprecipitates separated on polyacrylamide gel (FIG. 8A). Electrophoretic gel shift assay (EMSA) with nuclear extracts of cells treated for 20 minutes with INF-γ$^{32}$P-labeled IRF-1 GAS as probe (FIG. 8B).
Figure 8B:
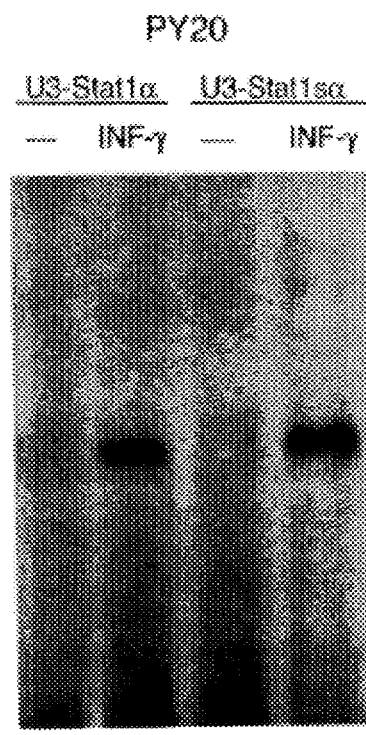
Figure 9:
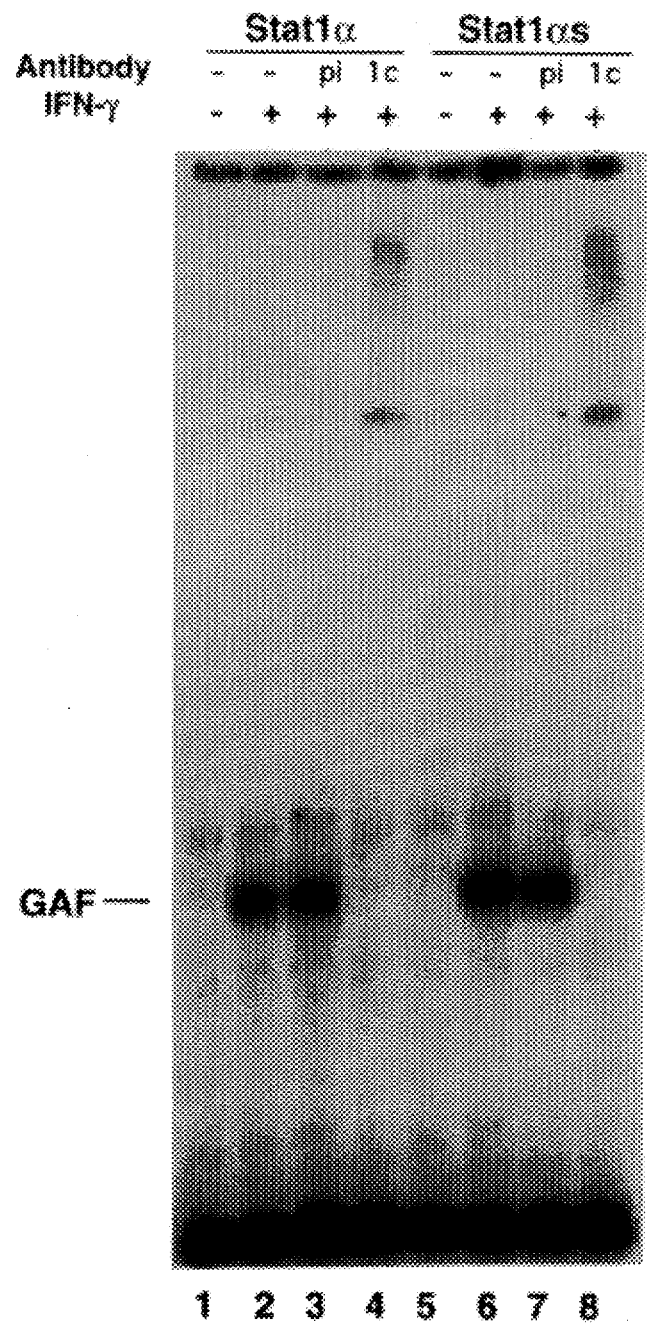
FIG. 9 Wild type and mutant Stat1α binding to IRF-1 GAS. The gel shift bands were specific because anti-Stat1C serum produced a supershift while the pre-immune serum had no affect.

Tyrosine phosphorylation and DNA binding of Stat1αs. To test the possible functional importance of serine 727 a recombinant mutant construct was prepared in which alanine was substituted for serine at residue 727. We first tested whether the serine$^{727}$ to alanine mutant (Stat1αs) had any affect on IFN-γ-induced phosphorylation on tyrosine and the subsequent development of DNA binding capacity. U3A cells that lack Stat1 protein were permanently transfected with expression vectors for wild type Stat1β or mutant Statices. Individual clones of cells expressing Stat1α or Stat1αs to comparable levels (also comparable to Stat1α expression of parental 2fTGH cells) were chosen for the remainder of this work (except that described in FIG. 11). After treatment with INF-γ for 20 minutes, both wild type and mutant proteins were phosphorylated on tyrosine as tested by anti-phosphotyrosine antibody reaction with Stat1 immunoprecipitates separated on polyacrylamide gel (FIG. 8A). Electrophoretic gel shift assay (EMSA) with nuclear extracts of cells treated for 20 minutes with INF-γ showed induced DNA binding activity using the $^{32}$P-labeled IRF-1 GAS as probe (FIG. 8B). In fact both wild type and mutant bound IRF-1 GAS (FIG. 9), Ly6E GAS and M67 deoxynucleotide probes equally (data not shown). The gel shift bands were specific because anti-Stat1C serum produced a supershift while the pre-immune serum had no affect (FIG. 9).

Figure 10A:
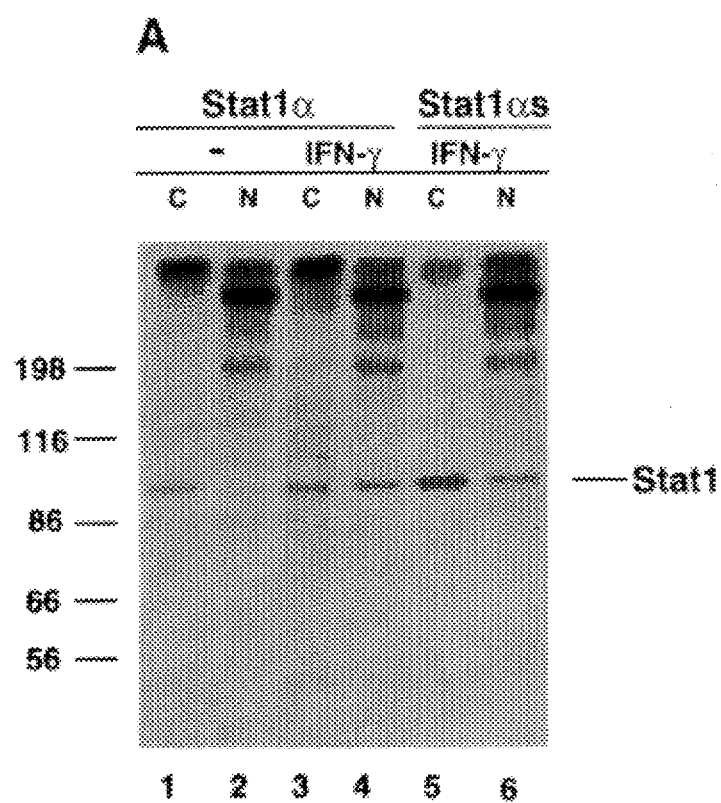
FIGS. 10A–10L Protein extracts were prepared, exposed to anti-Stat1C serum and the 91 kDa $^{32}$P-labeled band was detected by PAGE analysis (FIG. 10A). Autoradiongraphs of two dimensional thin layer chromatograms of trypsin digested wild type and mutant Stat1α from U3-cellular extracts treated or not treated with IFN-γ (FIGS. 10B–10L).
Figure 10B:
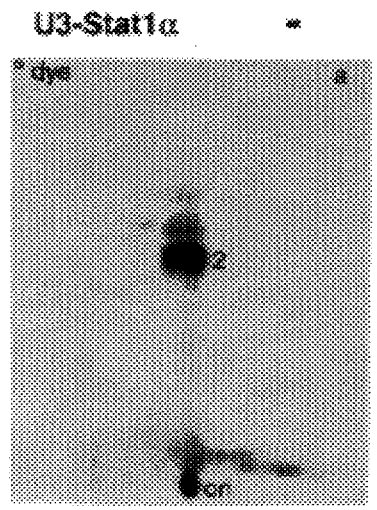
Figure 10C:
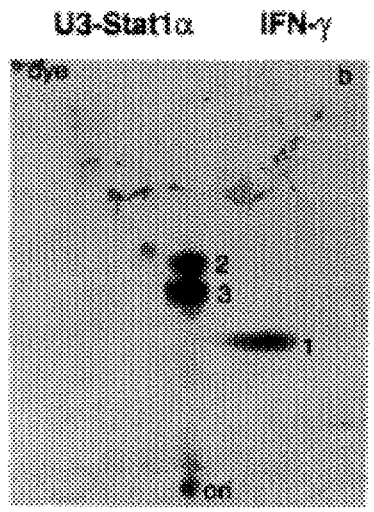
Figure 10D:
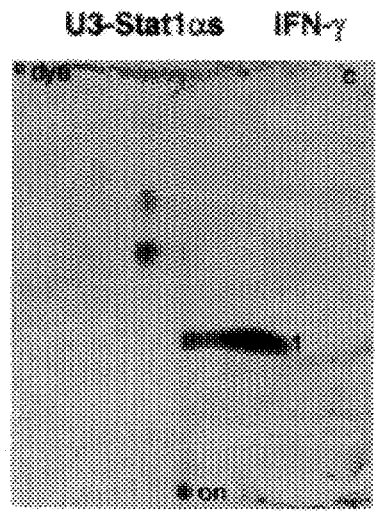
Figure 10E:
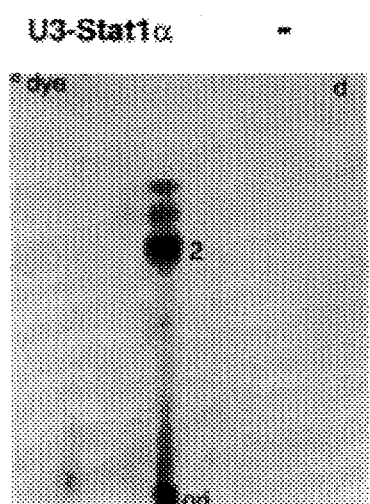
Figure 10F:
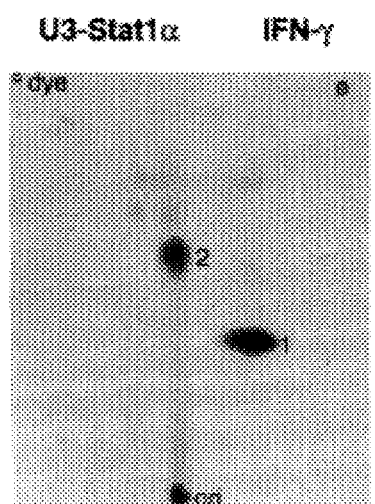
Figure 10G:
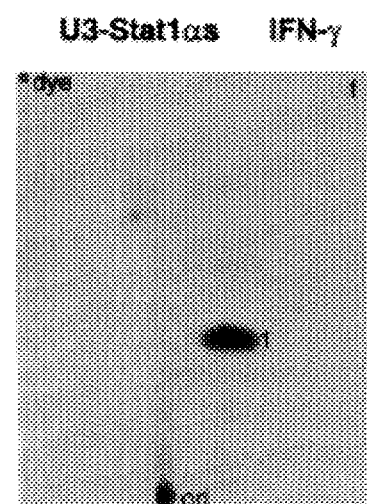

Serine727 is phosphorylated in vivo. We next determined directly whether the serine 727 residue participated in phosphorylation. Cells expressing either wild type Stat1α of Stat1αs were exposed to $^{32}$-orthophosphate for 2.5 hours and treated with INF-γ for 20 minutes. (As a control, the wild type cells were also labeled without INF-γ treatment.) Protein extracts were prepared, exposed to anti-Stat1C serum and the 91 kDa $^{32}$P-labeled band (FIG. 10A) was selected after SDS polyacrylamide gel electrophoresis. The labeled Stat1 samples were digested with trypsin, applied to thin-layer cellulose plates and separated by a two-dimensional procedure involving first electrophoresis at pH 3.5, rotating the plate 90°, followed by chromatography in 1-butanol/acidic acid/pyridine solution. Autoradiograms of the samples revealed an INF-γ-induced peptide in both wild type and mutant samples that migrated similarly to the earlier described phosphotyrosine containing peptide, GIYTEK (FIGS. 10B–G) (SEQ ID NO:39). This phosphopeptide was not present in the sample from cells expressing wild type protein that were not treated with INF-γ. A second peptide (actually a double spot possibly due to incomplete trypsin digestion) contained phosphoserine. This phosphoserine containing peptide was present in either INF-γ-treated or untreated cells containing the wild type protein but was completely absent from cells containing the mutant protein Stat1αs. Thus, a single serine to alanine mutation at residue 727 apparently removed the major target site in these cells for serine phosphorylation in Stat1.

Figures 10H, 10I, 10J, 10K, 10L:
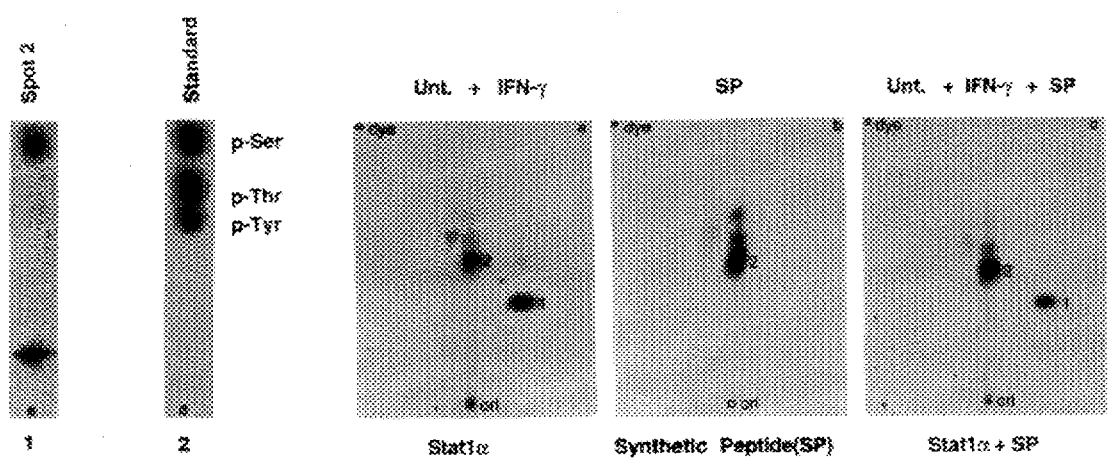

Note that the serine phosphorylation occurred whether or not the cells were treated with INF-γ in the presence of serum and that there was more phosphoserine than phosphotyrosine (FIG. 10H–I). This indicated that more Stat1α molecules were phosphorylated on serine than on phosphotyrosine since there is apparently a single serine of each residue that was phosphorylated, at least in U3-Stat1α complemented cells.

The site of serine phosphorylation was confirmed as residue 727 by synthesizing a 29 residue long peptide matching the human Stat1α sequence from residue 712 to 740. This peptide was treated with MAP kinase in the presence of $^{32}$P-γATP. The resulting labeled peptide was subjected to two-dimensional separation and eluted from the TLC plate. The purified $^{32}$P-labeled peptide was then digested with trypsin and the synthetic and authentic 32P phosphoserine labeled tryptic peptides compared by two-dimensional analysis (FIG. 10J–K). The two labeled peptides migrated very similarly (each sample was analyzed in a different chromatography tank leading to the slight differences in migration) and when mixed yield a single spot, the conventional method of demonstrating phosphopeptide identity. The experiment also established that the Stat1 peptide was a substrate for the MAP kinase which was suspected to be possible because the sequence of the potential phosphorylation site PMSP matches the known MAP kinase recognition site. Of course, this does not prove the nature of the responsible kinase inside cells.

Figure 11:
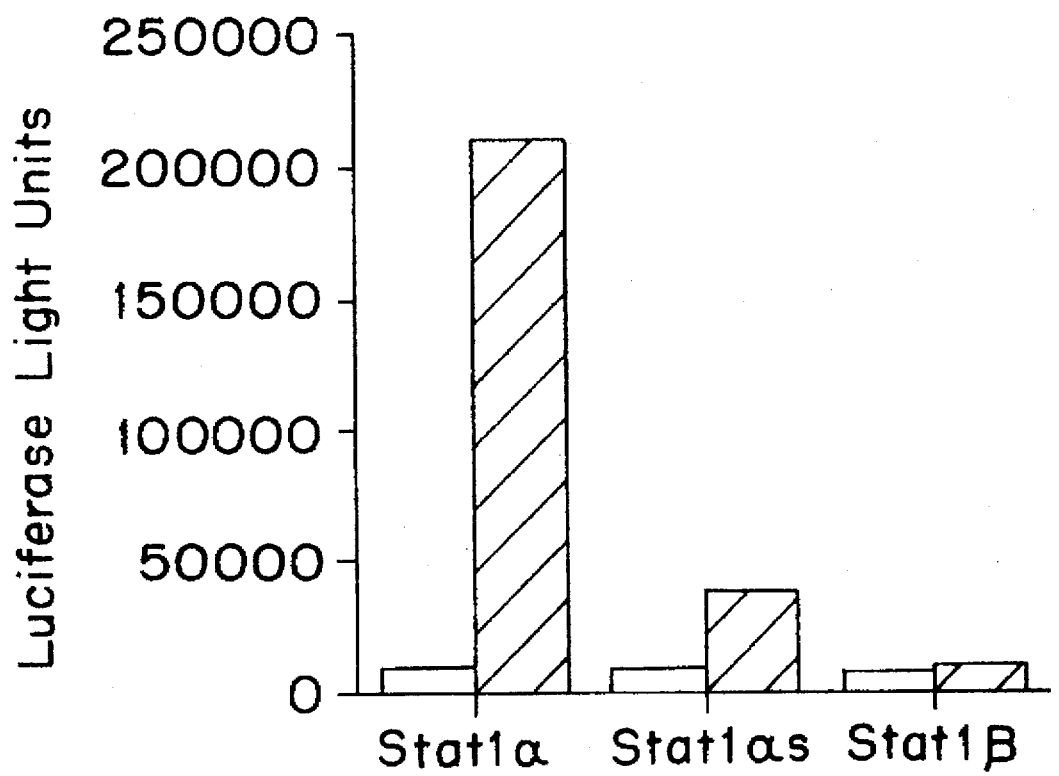
FIG. 11 Level of expression of a luciferase protein under control of three GAS sites from the promoter of the Ly6E gene in cells transfected with wild type Stat1α, mutant Stat1α, and Stat1β.

Requirement for serine 727 in Stat1α transcriptional induction. Having demonstrated that serine phosphorylation of residue 727 in Stat1 occurs in vivo, we tested for any effects on INF-γ dependent transcription. Three experiments indicated that the serine at position 727 was required for maximal IFN-γ-dependent transcriptional stimulation. First, U3 cells were transfected either with wild type Stat1α or the mutant Stat1αs plus a reporter gene construct with three GAS sites from the promoter of the Ly6E gene. After 16 hours, the cells were either treated with INF-γ or left untreated and extracts were assayed for luciferase activity six hours later. As a control Stat1β was also used. Stat1β lacks the terminal 38 amino acids of Stat1α including the serine 727 residue and is known not to drive INF-γ-induced transcription. The results of this experiment are shown in FIG. 11. The wild type Stat1α produced a 30-fold higher luciferase signal after IFN-γ induction whereas the Stat1β gave almost no increased signal. Stat1αs gave about a 5-fold increase consistent with the conclusion that a large fraction but not all of the INF-γ transcriptional response requires not only the phosphotyrosine as demonstrated earlier but requires phosphoserine on residue 727.

Figure 12A:
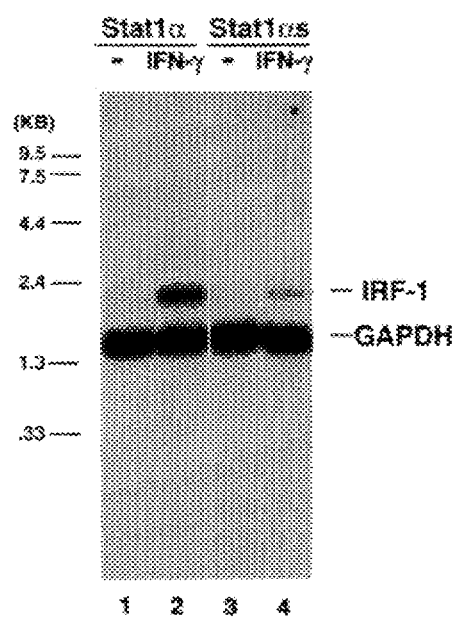
FIGS. 12A–12B FIG. 12A depicts the Northern blot analysis for IRF1 mRNA, an INF-γ-induced gene, in U3A-derived cell lines containing wild type Stat1α or mutant Stat1αs treated with INF-γ.

A second experiment tested that response of endogenous genes that are transcriptionally induced by INF-γ treatment. Permanent U3A-derived cell lines containing wild type Stat1α or mutant Stat1αs were treated with INF-γ for 3 hours, poly(A)+RNA extracted, and subjected to Northern blot analysis for IRF1 mRNA, an INF-γ-induced gene (FIG. 12A). There was an about 12-fold increase in IRF1 mRNA in cells containing wild type Stat1α whereas the cells with Stat1αs were induced about 3-fold, consistent with the transfectional analysis in FIG. 11.

Figure 12B:
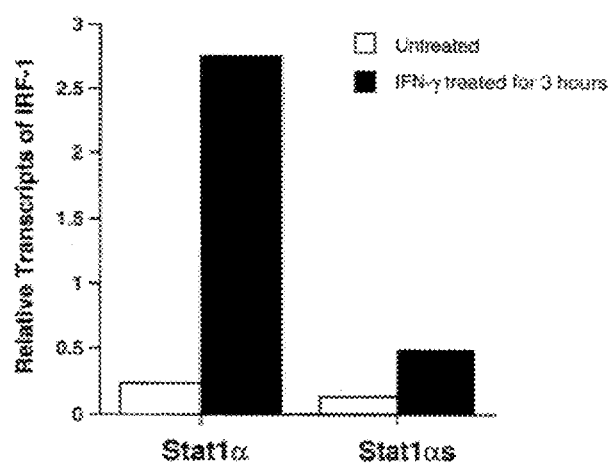

A final experiment compared the run-on transcriptional signal from the IRF1 gene in the two U3A cell derivatives. Again the INF-γ-induced transcriptional signal from the endogenous gene was significantly stronger with wild type than with mutant protein incorporated into the cells (FIG. 12B).

Discussion

This example demonstrates that a number of the STAT proteins contain a highly conserved potential serine kinase site in the carboxyl terminal residues. At least in Stat1 this residue must be phosphorylated for maximal IFN-induced transcription. Other data suggests that this serine is likely phosphorylated in the Stat3 molecule after IL-6 or EGF treatment as well. Stat1 protein containing an alanine residue 727 can be phosphorylated on tyrosine, dimerize and bind DNA but has only about 20% the transcriptional activation capacity of the wild type protein.

While this serine phosphorylation is required for maximal INF-γ transcriptional induction, it may not function at least for most genes in the INF-α pathway. Here Stat1β which lacks the serine site is equally active in forming functional ISGF-3, the transcription factor that activates INF-α sensitive genes and in IFN-α-induced mRNA accumulation.

These results in the IFN-γ pathway connect specific gene activation through the JAK-STAT pathway with one or more of the possible pathways that can result in the activation of serine kinases. In the present experiments serum grown cells that may, of course, be responding to polypeptides in the serum, apparently carry out a phosphorylation-dephosphorylation cycle of the latent Stat1α cytoplasmic proteins. This is detected as $^{32}$P labeling of Stat1α in serum grown cells in the absence of INF-γ. Only after INF-γ stimulation however is Stat1α tyrosine phosphorylated and activated to participate in transcription. A possible conclusion from these experiments is that transcriptional activation of a STAT-protein by a polypeptide ligand depends specifically on tyrosine phosphorylation to initiate the formation of transcriptively active complexes but the level of stimulation achieved depends in addition on serine phosphorylation which might come from any different serine kinases. Analysis of the importance of serine phosphorylation of the STAT proteins in general and of Stat1 in different cell types under different conditions is surely in order.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

It is further to be understood that all base-pair sizes given for nucleotides, and molecular weight or amino acid number given for protein, polypeptides, and peptides, are approximate, and are provided by way of comparison.

Various references are cited throughout this specification, each of which is incorporated herein by reference in its entirety.

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 3268 base pairs
        ( B ) TYPE: nucleic acid
        ( C ) STRANDEDNESS: both
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( v i i ) IMMEDIATE SOURCE:
        ( B ) CLONE: HeLa ( i x ) FEATURE:
        ( A ) NAME/KEY: CDS
        ( B ) LOCATION: 25..2577

( x i ) SEQUENCE DESCRIPTION: SEQ ID NO:1:

```
ACTGCAACCC TAATCAGAGC CCAA ATG GCG CAG TGG GAA ATG CTG CAG AAT        51
                            Met Ala Gln Trp Glu Met Leu Gln Asn
                             1               5

CTT GAC AGC CCC TTT CAG GAT CAG CTG CAC CAG CTT TAC TCG CAC AGC        99
Leu Asp Ser Pro Phe Gln Asp Gln Leu His Gln Leu Tyr Ser His Ser
 10              15                  20                  25

CTC CTG CCT GTG GAC ATT CGA CAG TAC TTG GCT GTC TGG ATT GAA GAC       147
Leu Leu Pro Val Asp Ile Arg Gln Tyr Leu Ala Val Trp Ile Glu Asp
                 30                  35                  40

CAG AAC TGG CAG GAA GCT GCA CTT GGG AGT GAT GAT TCC AAG GCT ACC       195
Gln Asn Trp Gln Glu Ala Ala Leu Gly Ser Asp Asp Ser Lys Ala Thr
             45                  50                  55

ATG CTA TTC TTC CAC TTC TTG GAT CAG CTG AAC TAT GAG TGT GGC CGT       243
Met Leu Phe Phe His Phe Leu Asp Gln Leu Asn Tyr Glu Cys Gly Arg
         60                  65                  70

TGC AGC CAG GAC CCA GAG TCC TTG TTG CTG CAG CAC AAT TTG CGG AAA       291
Cys Ser Gln Asp Pro Glu Ser Leu Leu Leu Gln His Asn Leu Arg Lys
     75                  80                  85

TTC TGC CGG GAC ATT CAG CCC TTT TCC CAG GAT CCT ACC CAG TTG GCT       339
Phe Cys Arg Asp Ile Gln Pro Phe Ser Gln Asp Pro Thr Gln Leu Ala
 90                  95                 100                 105

GAG ATG ATC TTT AAC CTC CTT CTG GAA GAA AAA AGA ATT TTG ATC CAG       387
Glu Met Ile Phe Asn Leu Leu Leu Glu Glu Lys Arg Ile Leu Ile Gln
                 110                 115                 120

GCT CAG AGG GCC CAA TTG GAA CAA GGA GAG CCA GTT CTC GAA ACA CCT       435
Ala Gln Arg Ala Gln Leu Glu Gln Gly Glu Pro Val Leu Glu Thr Pro
             125                 130                 135

GTG GAG AGC CAG CAA CAT GAG ATT GAA TCC CGG ATC CTG GAT TTA AGG       483
Val Glu Ser Gln Gln His Glu Ile Glu Ser Arg Ile Leu Asp Leu Arg
         140                 145                 150

GCT ATG ATG GAG AAG CTG GTA AAA TCC ATC AGC CAA CTG AAA GAC CAG       531
Ala Met Met Glu Lys Leu Val Lys Ser Ile Ser Gln Leu Lys Asp Gln
     155                 160                 165

CAG GAT GTC TTC TGC TTC CGA TAT AAG ATC CAG GCC AAA GGG AAG ACA       579
Gln Asp Val Phe Cys Phe Arg Tyr Lys Ile Gln Ala Lys Gly Lys Thr
```

| | | | | | | | | | | | | | | | | |
|---|---|---|---|---|---|---|---|---|---|---|---|---|---|---|---|---|
| 170 | | | | | 175 | | | | | 180 | | | | | 185 | |
| CCC | TCT | CTG | GAC | CCC | CAT | CAG | ACC | AAA | GAG | CAG | AAG | ATT | CTG | CAG | GAA | 627 |
| Pro | Ser | Leu | Asp | Pro | His | Gln | Thr | Lys | Glu | Gln | Lys | Ile | Leu | Gln | Glu | |
| | | | | 190 | | | | | 195 | | | | | 200 | | |
| ACT | CTC | AAT | GAA | CTG | GAC | AAA | AGG | AGA | AAG | GAG | GTG | CTG | GAT | GCC | TCC | 675 |
| Thr | Leu | Asn | Glu | Leu | Asp | Lys | Arg | Arg | Lys | Glu | Val | Leu | Asp | Ala | Ser | |
| | | | | 205 | | | | | 210 | | | | | 215 | | |
| AAA | GCA | CTG | CTA | GGC | CGA | TTA | ACT | ACC | CTA | ATC | GAG | CTA | CTG | CTG | CCA | 723 |
| Lys | Ala | Leu | Leu | Gly | Arg | Leu | Thr | Thr | Leu | Ile | Glu | Leu | Leu | Leu | Pro | |
| | | | 220 | | | | | 225 | | | | | 230 | | | |
| AAG | TTG | GAG | GAG | TGG | AAG | GCC | CAG | CAG | CAA | AAA | GCC | TGC | ATC | AGA | GCT | 771 |
| Lys | Leu | Glu | Glu | Trp | Lys | Ala | Gln | Gln | Gln | Lys | Ala | Cys | Ile | Arg | Ala | |
| | | 235 | | | | | 240 | | | | | 245 | | | | |
| CCC | ATT | GAC | CAC | GGG | TTG | GAA | CAG | CTG | GAG | ACA | TGG | TTC | ACA | GCT | GGA | 819 |
| Pro | Ile | Asp | His | Gly | Leu | Glu | Gln | Leu | Glu | Thr | Trp | Phe | Thr | Ala | Gly | |
| 250 | | | | | 255 | | | | | 260 | | | | | 265 | |
| GCA | AAG | CTG | TTG | TTT | CAC | CTG | AGG | CAG | CTG | CTG | AAG | GAG | CTG | AAG | GGA | 867 |
| Ala | Lys | Leu | Leu | Phe | His | Leu | Arg | Gln | Leu | Leu | Lys | Glu | Leu | Lys | Gly | |
| | | | | 270 | | | | | 275 | | | | | 280 | | |
| CTG | AGT | TGC | CTG | GTT | AGC | TAT | CAG | GAT | GAC | CCT | CTG | ACC | AAA | GGG | GTG | 915 |
| Leu | Ser | Cys | Leu | Val | Ser | Tyr | Gln | Asp | Asp | Pro | Leu | Thr | Lys | Gly | Val | |
| | | | 285 | | | | | 290 | | | | | 295 | | | |
| GAC | CTA | CGC | AAC | GCC | CAG | GTC | ACA | GAG | TTG | CTA | CAG | CGT | CTG | CTC | CAC | 963 |
| Asp | Leu | Arg | Asn | Ala | Gln | Val | Thr | Glu | Leu | Leu | Gln | Arg | Leu | Leu | His | |
| | | 300 | | | | | 305 | | | | | 310 | | | | |
| AGA | GCC | TTT | GTG | GTA | GAA | ACC | CAG | CCC | TGC | ATG | CCC | CAA | ACT | CCC | CAT | 1011 |
| Arg | Ala | Phe | Val | Val | Glu | Thr | Gln | Pro | Cys | Met | Pro | Gln | Thr | Pro | His | |
| | 315 | | | | | 320 | | | | | 325 | | | | | |
| CGA | CCC | CTC | ATC | CTC | AAG | ACT | GGC | AGC | AAG | TTC | ACC | GTC | CGA | ACA | AGG | 1059 |
| Arg | Pro | Leu | Ile | Leu | Lys | Thr | Gly | Ser | Lys | Phe | Thr | Val | Arg | Thr | Arg | |
| 330 | | | | | 335 | | | | | 340 | | | | | 345 | |
| CTG | CTG | GTG | AGA | CTC | CAG | GAA | GGC | AAT | GAG | TCA | CTG | ACT | GTG | GAA | GTC | 1107 |
| Leu | Leu | Val | Arg | Leu | Gln | Glu | Gly | Asn | Glu | Ser | Leu | Thr | Val | Glu | Val | |
| | | | | 350 | | | | | 355 | | | | | 360 | | |
| TCC | ATT | GAC | AGG | AAT | CCT | CCT | CAA | TTA | CAA | GGC | TTC | CGG | AAG | TTC | AAC | 1155 |
| Ser | Ile | Asp | Arg | Asn | Pro | Pro | Gln | Leu | Gln | Gly | Phe | Arg | Lys | Phe | Asn | |
| | | | 365 | | | | | 370 | | | | | 375 | | | |
| ATT | CTG | ACT | TCA | AAC | CAG | AAA | ACT | TTG | ACC | CCC | GAG | AAG | GGG | CAG | AGT | 1203 |
| Ile | Leu | Thr | Ser | Asn | Gln | Lys | Thr | Leu | Thr | Pro | Glu | Lys | Gly | Gln | Ser | |
| | | 380 | | | | | 385 | | | | | 390 | | | | |
| CAG | GGT | TTG | ATT | TGG | GAC | TTT | GGT | TAC | CTG | ACT | CTG | GTG | GAG | CAA | CGT | 1251 |
| Gln | Gly | Leu | Ile | Trp | Asp | Phe | Gly | Tyr | Leu | Thr | Leu | Val | Glu | Gln | Arg | |
| | 395 | | | | | 400 | | | | | 405 | | | | | |
| TCA | GGT | GGT | TCA | GGA | AAG | GGC | AGC | AAT | AAG | GGG | CCA | CTA | GGT | GTG | ACA | 1299 |
| Ser | Gly | Gly | Ser | Gly | Lys | Gly | Ser | Asn | Lys | Gly | Pro | Leu | Gly | Val | Thr | |
| 410 | | | | | 415 | | | | | 420 | | | | | 425 | |
| GAG | GAA | CTG | CAC | ATC | ATC | AGC | TTC | ACG | GTC | AAA | TAT | ACC | TAC | CAG | GGT | 1347 |
| Glu | Glu | Leu | His | Ile | Ile | Ser | Phe | Thr | Val | Lys | Tyr | Thr | Tyr | Gln | Gly | |
| | | | | 430 | | | | | 435 | | | | | 440 | | |
| CTG | AAG | CAG | GAG | CTG | AAA | ACG | GAC | ACC | CTC | CCT | GTG | GTG | ATT | ATT | TCC | 1395 |
| Leu | Lys | Gln | Glu | Leu | Lys | Thr | Asp | Thr | Leu | Pro | Val | Val | Ile | Ile | Ser | |
| | | | 445 | | | | | 450 | | | | | 455 | | | |
| AAC | ATG | AAC | CAG | CTC | TCA | ATT | GCC | TGG | GCT | TCA | GTT | CTC | TGG | TTC | AAT | 1443 |
| Asn | Met | Asn | Gln | Leu | Ser | Ile | Ala | Trp | Ala | Ser | Val | Leu | Trp | Phe | Asn | |
| | | 460 | | | | | 465 | | | | | 470 | | | | |
| TTG | CTC | AGC | CCA | AAC | CTT | CAG | AAC | CAG | CAG | TTC | TTC | TCC | AAC | CCC | CCC | 1491 |
| Leu | Leu | Ser | Pro | Asn | Leu | Gln | Asn | Gln | Gln | Phe | Phe | Ser | Asn | Pro | Pro | |
| | 475 | | | | | 480 | | | | | 485 | | | | | |
| AAG | GCC | CCC | TGG | AGC | TTG | CTG | GGC | CCT | GCT | CTC | AGT | TGG | CAG | TTC | TCC | 1539 |
| Lys | Ala | Pro | Trp | Ser | Leu | Leu | Gly | Pro | Ala | Leu | Ser | Trp | Gln | Phe | Ser | |

```
                490                              495                              500                              505
TCC TAT GTT GGC CGA GGC CTC AAC TCA GAC CAG CTG AGC ATG CTG AGA                                                         1587
Ser Tyr Val Gly Arg Gly Leu Asn Ser Asp Gln Leu Ser Met Leu Arg
                510                     515                     520

AAC AAG CTG TTC GGG CAG AAC TGT AGG ACT GAG GAT CCA TTA TTG TCC                                                         1635
Asn Lys Leu Phe Gly Gln Asn Cys Arg Thr Glu Asp Pro Leu Leu Ser
            525                     530                     535

TGG GCT GAC TTC ACT AAG CGA GAG AGC CCT CCT GGC AAG TTA CCA TTC                                                         1683
Trp Ala Asp Phe Thr Lys Arg Glu Ser Pro Pro Gly Lys Leu Pro Phe
        540                     545                     550

TGG ACA TGG CTG GAC AAA ATT CTG GAG TTG GTA CAT GAC CAC CTG AAG                                                         1731
Trp Thr Trp Leu Asp Lys Ile Leu Glu Leu Val His Asp His Leu Lys
        555                     560                     565

GAT CTC TGG AAT GAT GGA CGC ATC ATG GGC TTT GTG AGT CGG AGC CAG                                                         1779
Asp Leu Trp Asn Asp Gly Arg Ile Met Gly Phe Val Ser Arg Ser Gln
570                     575                     580                     585

GAG CGC CGG CTG CTG AAG AAG ACC ATG TCT GGC ACC TTT CTA CTG CGC                                                         1827
Glu Arg Arg Leu Leu Lys Lys Thr Met Ser Gly Thr Phe Leu Leu Arg
                590                     595                     600

TTC AGT GAA TCG TCA GAA GGG GGC ATT ACC TGC TCC TGG GTG GAG CAC                                                         1875
Phe Ser Glu Ser Ser Glu Gly Gly Ile Thr Cys Ser Trp Val Glu His
                605                     610                     615

CAG GAT GAT GAC AAG GTG CTC ATC TAC TCT GTG CAA CCG TAC ACG AAG                                                         1923
Gln Asp Asp Asp Lys Val Leu Ile Tyr Ser Val Gln Pro Tyr Thr Lys
        620                     625                     630

GAG GTG CTG CAG TCA CTC CCG CTG ACT GAA ATC ATC CGC CAT TAC CAG                                                         1971
Glu Val Leu Gln Ser Leu Pro Leu Thr Glu Ile Ile Arg His Tyr Gln
635                     640                     645

TTG CTC ACT GAG GAG AAT ATA CCT GAA AAC CCA CTG CGC TTC CTC TAT                                                         2019
Leu Leu Thr Glu Glu Asn Ile Pro Glu Asn Pro Leu Arg Phe Leu Tyr
650                     655                     660                     665

CCC CGA ATC CCC CGG GAT GAA GCT TTT GGG TGC TAC TAC CAG GAG AAA                                                         2067
Pro Arg Ile Pro Arg Asp Glu Ala Phe Gly Cys Tyr Tyr Gln Glu Lys
                670                     675                     680

GTT AAT CTC CAG GAA CGG AGG AAA TAC CTG AAA CAC AGG CTC ATT GTG                                                         2115
Val Asn Leu Gln Glu Arg Arg Lys Tyr Leu Lys His Arg Leu Ile Val
            685                     690                     695

GTC TCT AAT AGA CAG GTG GAT GAA CTG CAA CAA CCG CTG GAG CTT AAG                                                         2163
Val Ser Asn Arg Gln Val Asp Glu Leu Gln Gln Pro Leu Glu Leu Lys
        700                     705                     710

CCA GAG CCA GAG CTG GAG TCA TTA GAG CTG GAA CTA GGG CTG GTG CCA                                                         2211
Pro Glu Pro Glu Leu Glu Ser Leu Glu Leu Glu Leu Gly Leu Val Pro
        715                     720                     725

GAG CCA GAG CTC AGC CTG GAC TTA GAG CCA CTG CTG AAG GCA GGG CTG                                                         2259
Glu Pro Glu Leu Ser Leu Asp Leu Glu Pro Leu Leu Lys Ala Gly Leu
730                     735                     740                     745

GAT CTG GGG CCA GAG CTA GAG TCT GTG CTG GAG TCC ACT CTG GAG CCT                                                         2307
Asp Leu Gly Pro Glu Leu Glu Ser Val Leu Glu Ser Thr Leu Glu Pro
                750                     755                     760

GTG ATA GAG CCC ACA CTA TGC ATG GTA TCA CAA ACA GTG CCA GAG CCA                                                         2355
Val Ile Glu Pro Thr Leu Cys Met Val Ser Gln Thr Val Pro Glu Pro
                765                     770                     775

GAC CAA GGA CCT GTA TCA CAG CCA GTG CCA GAG CCA GAT TTG CCC TGT                                                         2403
Asp Gln Gly Pro Val Ser Gln Pro Val Pro Glu Pro Asp Leu Pro Cys
        780                     785                     790

GAT CTG AGA CAT TTG AAC ACT GAG CCA ATG GAA ATC TTC AGA AAC TGT                                                         2451
Asp Leu Arg His Leu Asn Thr Glu Pro Met Glu Ile Phe Arg Asn Cys
        795                     800                     805

GTA AAG ATT GAA GAA ATC ATG CCG AAT GGT GAC CCA CTG TTG GCT GGC                                                         2499
Val Lys Ile Glu Glu Ile Met Pro Asn Gly Asp Pro Leu Leu Ala Gly
```

-continued

```
            810                     815                     820                     825
CAG AAC ACC GTG GAT GAG GTT TAC GTC TCC CGC CCC AGC CAC TTC TAC       2547
Gln Asn Thr Val Asp Glu Val Tyr Val Ser Arg Pro Ser His Phe Tyr
                    830                     835                     840

ACT GAT GGA CCC TTG ATG CCT TCT GAC TTC TAGGAACCAC ATTTCCTCTG         2597
Thr Asp Gly Pro Leu Met Pro Ser Asp Phe
                845                     850

TTCTTTTCAT ATCTCTTTGC CCTTCCTACT CCTCATAGCA TGATATTGTT CTCCAAGG       2657
GGGAATCAGG CATGTGTCCC TTCCAAGCTG TGTTAACTGT TCAAACTCAG GCCTGTGT       2717
CTCCATTGGG GTGAGAGGTG AAAGCATAAC ATGGGTACAG AGGGGACAAC AATGAATC       2777
AACAGATGCT GAGCCATAGG TCTAAATAGG ATCCTGGAGG CTGCCTGCTG TGCTGGGA       2837
TATAGGGGTC CTGGGGGCAG GCCAGGGCAG TTGACAGGTA CTTGGAGGGC TCAGGGCA       2897
GGCTTCTTTC CAGTATGGAA GGATTTCAAC ATTTTAATAG TTGGTTAGGC TAAACTGG       2957
CATACTGGCA TTGGCCTTGG TGGGGAGCAC AGACACAGGA TAGGACTCCA TTTCTTTC       3017
CCATTCCTTC ATGTCTAGGA TAACTTGCTT TCTTCTTTCC TTTACTCCTG GCTCAAGC       3077
TGAATTTCTT CTTTTCCTGC AGGGGTTGAG AGCTTCTGCC CTTAGCCTAC CATGTGAA       3137
TCTACCCTGA AGAAAGGGAT GGATAGGAAG TAGACCTCTT TTTCTTACCA GTCTCCTC       3197
CTACTCTGCC CCCTAAGCTG GCTGTACCTG TTCCTCCCCC ATAAAATGAT CCTGCCAA       3257
TAAAAAAAA A                                                          3268
```

( 2 ) INFORMATION FOR SEQ ID NO:2:

( i ) SEQUENCE CHARACTERISTICS:
( A ) LENGTH: 851 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Ala Gln Trp Glu Met Leu Gln Asn Leu Asp Ser Pro Phe Gln Asp
 1               5                  10                  15

Gln Leu His Gln Leu Tyr Ser His Ser Leu Leu Pro Val Asp Ile Arg
            20                  25                  30

Gln Tyr Leu Ala Val Trp Ile Glu Asp Gln Asn Trp Gln Glu Ala Ala
        35                  40                  45

Leu Gly Ser Asp Asp Ser Lys Ala Thr Met Leu Phe Phe His Phe Leu
    50                  55                  60

Asp Gln Leu Asn Tyr Glu Cys Gly Arg Cys Ser Gln Asp Pro Glu Ser
65                  70                  75                  80

Leu Leu Leu Gln His Asn Leu Arg Lys Phe Cys Arg Asp Ile Gln Pro
                85                  90                  95

Phe Ser Gln Asp Pro Thr Gln Leu Ala Glu Met Ile Phe Asn Leu Leu
            100                 105                 110

Leu Glu Glu Lys Arg Ile Leu Ile Gln Ala Gln Arg Ala Gln Leu Glu
        115                 120                 125

Gln Gly Glu Pro Val Leu Glu Thr Pro Val Glu Ser Gln Gln His Glu
    130                 135                 140

Ile Glu Ser Arg Ile Leu Asp Leu Arg Ala Met Met Glu Lys Leu Val
145                 150                 155                 160

Lys Ser Ile Ser Gln Leu Lys Asp Gln Gln Asp Val Phe Cys Phe Arg
                165                 170                 175

Tyr Lys Ile Gln Ala Lys Gly Lys Thr Pro Ser Leu Asp Pro His Gln
```

-continued

|     |     |     |     |     | 180 |     |     |     |     | 185 |     |     |     |     | 190 |     |     |
| --- | --- | --- | --- | --- | --- | --- | --- | --- | --- | --- | --- | --- | --- | --- | --- | --- | --- |
| Thr | Lys | Glu | Gln | Lys | Ile | Leu | Gln | Glu | Thr | Leu | Asn | Glu | Leu | Asp | Lys |
|     |     | 195 |     |     |     |     | 200 |     |     |     |     | 205 |     |     |     |
| Arg | Arg | Lys | Glu | Val | Leu | Asp | Ala | Ser | Lys | Ala | Leu | Leu | Gly | Arg | Leu |
|     | 210 |     |     |     |     | 215 |     |     |     |     | 220 |     |     |     |     |
| Thr | Thr | Leu | Ile | Glu | Leu | Leu | Leu | Pro | Lys | Leu | Glu | Glu | Trp | Lys | Ala |
| 225 |     |     |     |     | 230 |     |     |     |     | 235 |     |     |     |     | 240 |
| Gln | Gln | Gln | Lys | Ala | Cys | Ile | Arg | Ala | Pro | Ile | Asp | His | Gly | Leu | Glu |
|     |     |     |     | 245 |     |     |     |     | 250 |     |     |     |     | 255 |     |
| Gln | Leu | Glu | Thr | Trp | Phe | Thr | Ala | Gly | Ala | Lys | Leu | Leu | Phe | His | Leu |
|     |     |     | 260 |     |     |     |     | 265 |     |     |     |     | 270 |     |     |
| Arg | Gln | Leu | Leu | Lys | Glu | Leu | Lys | Gly | Leu | Ser | Cys | Leu | Val | Ser | Tyr |
|     |     | 275 |     |     |     |     | 280 |     |     |     |     | 285 |     |     |     |
| Gln | Asp | Asp | Pro | Leu | Thr | Lys | Gly | Val | Asp | Leu | Arg | Asn | Ala | Gln | Val |
|     | 290 |     |     |     |     | 295 |     |     |     |     | 300 |     |     |     |     |
| Thr | Glu | Leu | Leu | Gln | Arg | Leu | Leu | His | Arg | Ala | Phe | Val | Val | Glu | Thr |
| 305 |     |     |     |     | 310 |     |     |     |     | 315 |     |     |     |     | 320 |
| Gln | Pro | Cys | Met | Pro | Gln | Thr | Pro | His | Arg | Pro | Leu | Ile | Leu | Lys | Thr |
|     |     |     |     | 325 |     |     |     |     | 330 |     |     |     |     | 335 |     |
| Gly | Ser | Lys | Phe | Thr | Val | Arg | Thr | Arg | Leu | Leu | Val | Arg | Leu | Gln | Glu |
|     |     |     | 340 |     |     |     |     | 345 |     |     |     |     | 350 |     |     |
| Gly | Asn | Glu | Ser | Leu | Thr | Val | Glu | Val | Ser | Ile | Asp | Arg | Asn | Pro | Pro |
|     |     | 355 |     |     |     |     | 360 |     |     |     |     | 365 |     |     |     |
| Gln | Leu | Gln | Gly | Phe | Arg | Lys | Phe | Asn | Ile | Leu | Thr | Ser | Asn | Gln | Lys |
|     | 370 |     |     |     |     | 375 |     |     |     |     | 380 |     |     |     |     |
| Thr | Leu | Thr | Pro | Glu | Lys | Gly | Gln | Ser | Gln | Gly | Leu | Ile | Trp | Asp | Phe |
| 385 |     |     |     |     | 390 |     |     |     |     | 395 |     |     |     |     | 400 |
| Gly | Tyr | Leu | Thr | Leu | Val | Glu | Gln | Arg | Ser | Gly | Gly | Ser | Gly | Lys | Gly |
|     |     |     |     | 405 |     |     |     |     | 410 |     |     |     |     | 415 |     |
| Ser | Asn | Lys | Gly | Pro | Leu | Gly | Val | Thr | Glu | Glu | Leu | His | Ile | Ile | Ser |
|     |     |     | 420 |     |     |     |     | 425 |     |     |     |     | 430 |     |     |
| Phe | Thr | Val | Lys | Tyr | Thr | Tyr | Gln | Gly | Leu | Lys | Gln | Glu | Leu | Lys | Thr |
|     |     | 435 |     |     |     |     | 440 |     |     |     |     | 445 |     |     |     |
| Asp | Thr | Leu | Pro | Val | Val | Ile | Ile | Ser | Asn | Met | Asn | Gln | Leu | Ser | Ile |
|     | 450 |     |     |     |     | 455 |     |     |     |     | 460 |     |     |     |     |
| Ala | Trp | Ala | Ser | Val | Leu | Trp | Phe | Asn | Leu | Leu | Ser | Pro | Asn | Leu | Gln |
| 465 |     |     |     |     | 470 |     |     |     |     | 475 |     |     |     |     | 480 |
| Asn | Gln | Gln | Phe | Phe | Ser | Asn | Pro | Pro | Lys | Ala | Pro | Trp | Ser | Leu | Leu |
|     |     |     |     | 485 |     |     |     |     | 490 |     |     |     |     | 495 |     |
| Gly | Pro | Ala | Leu | Ser | Trp | Gln | Phe | Ser | Ser | Tyr | Val | Gly | Arg | Gly | Leu |
|     |     |     | 500 |     |     |     |     | 505 |     |     |     |     | 510 |     |     |
| Asn | Ser | Asp | Gln | Leu | Ser | Met | Leu | Arg | Asn | Lys | Leu | Phe | Gly | Gln | Asn |
|     |     | 515 |     |     |     |     | 520 |     |     |     |     | 525 |     |     |     |
| Cys | Arg | Thr | Glu | Asp | Pro | Leu | Leu | Ser | Trp | Ala | Asp | Phe | Thr | Lys | Arg |
|     | 530 |     |     |     |     | 535 |     |     |     |     | 540 |     |     |     |     |
| Glu | Ser | Pro | Pro | Gly | Lys | Leu | Pro | Phe | Trp | Thr | Trp | Leu | Asp | Lys | Ile |
| 545 |     |     |     |     | 550 |     |     |     |     | 555 |     |     |     |     | 560 |
| Leu | Glu | Leu | Val | His | Asp | His | Leu | Lys | Asp | Leu | Trp | Asn | Asp | Gly | Arg |
|     |     |     |     | 565 |     |     |     |     | 570 |     |     |     |     | 575 |     |
| Ile | Met | Gly | Phe | Val | Ser | Arg | Ser | Gln | Glu | Arg | Arg | Leu | Leu | Lys | Lys |
|     |     |     | 580 |     |     |     |     | 585 |     |     |     |     | 590 |     |     |
| Thr | Met | Ser | Gly | Thr | Phe | Leu | Leu | Arg | Phe | Ser | Glu | Ser | Ser | Glu | Gly |
|     |     |     |     | 595 |     |     |     |     | 600 |     |     |     |     | 605 |     |

```
Gly Ile Thr Cys Ser Trp Val Glu His Gln Asp Asp Lys Val Leu
    610                 615                 620
Ile Tyr Ser Val Gln Pro Tyr Thr Lys Glu Val Leu Gln Ser Leu Pro
625                 630                 635                 640
Leu Thr Glu Ile Ile Arg His Tyr Gln Leu Leu Thr Glu Glu Asn Ile
                645                 650                 655
Pro Glu Asn Pro Leu Arg Phe Leu Tyr Pro Arg Ile Pro Arg Asp Glu
            660                 665                 670
Ala Phe Gly Cys Tyr Tyr Gln Glu Lys Val Asn Leu Gln Glu Arg Arg
            675                 680                 685
Lys Tyr Leu Lys His Arg Leu Ile Val Val Ser Asn Arg Gln Val Asp
    690                 695                 700
Glu Leu Gln Gln Pro Leu Glu Leu Lys Pro Glu Pro Glu Leu Glu Ser
705                 710                 715                 720
Leu Glu Leu Glu Leu Gly Leu Val Pro Glu Pro Glu Leu Ser Leu Asp
                725                 730                 735
Leu Glu Pro Leu Leu Lys Ala Gly Leu Asp Leu Gly Pro Glu Leu Glu
            740                 745                 750
Ser Val Leu Glu Ser Thr Leu Glu Pro Val Ile Glu Pro Thr Leu Cys
            755                 760                 765
Met Val Ser Gln Thr Val Pro Glu Pro Asp Gln Gly Pro Val Ser Gln
    770                 775                 780
Pro Val Pro Glu Pro Asp Leu Pro Cys Asp Leu Arg His Leu Asn Thr
785                 790                 795                 800
Glu Pro Met Glu Ile Phe Arg Asn Cys Val Lys Ile Glu Glu Ile Met
                805                 810                 815
Pro Asn Gly Asp Pro Leu Leu Ala Gly Gln Asn Thr Val Asp Glu Val
            820                 825                 830
Tyr Val Ser Arg Pro Ser His Phe Tyr Thr Asp Gly Pro Leu Met Pro
            835                 840                 845
Ser Asp Phe
    850
```

(2) INFORMATION FOR SEQ ID NO:3:

(i) SEQUENCE CHARACTERISTICS:
        (A) LENGTH: 3943 base pairs
        (B) TYPE: nucleic acid
        (C) STRANDEDNESS: both
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Homo sapiens (vii) IMMEDIATE SOURCE:
        (B) CLONE: Human Stat91

(ix) FEATURE:
        (A) NAME/KEY: CDS
        (B) LOCATION: 197..2449

(xi) SEQUENCE DESCRIPTION: SEQ ID NO:3:

```
ATTAAACCTC TCGCCGAGCC CCTCCGCAGA CTCTGCGCCG GAAAGTTTCA TTTGCTGTAT      60
GCCATCCTCG AGAGCTGTCT AGGTTAACGT TCGCACTCTG TGTATATAAC CTCGACAGTC     120
TTGGCACCTA ACGTGCTGTG CGTAGCTGCT CCTTTGGTTG AATCCCCAGG CCCTTGTTGG     180
```

| | | | | | | | | | | | | | | | | |
|---|---|---|---|---|---|---|---|---|---|---|---|---|---|---|---|---|
| GGCACAAGGT | GGCAGG | ATG | TCT | CAG | TGG | TAC | GAA | CTT | CAG | CAG | CTT | GAC | | | | 229 |
| | | Met | Ser | Gln | Trp | Tyr | Glu | Leu | Gln | Gln | Leu | Asp | | | | |
| | | 1 | | 5 | | | | | | 10 | | | | | | |
| TCA | AAA | TTC | CTG | GAG | CAG | GTT | CAC | CAG | CTT | TAT | GAT | GAC | AGT | TTT | CCC | 277 |
| Ser | Lys | Phe | Leu | Glu | Gln | Val | His | Gln | Leu | Tyr | Asp | Asp | Ser | Phe | Pro | |
| | 15 | | | | 20 | | | | | 25 | | | | | | |
| ATG | GAA | ATC | AGA | CAG | TAC | CTG | GCA | CAG | TGG | TTA | GAA | AAG | CAA | GAC | TGG | 325 |
| Met | Glu | Ile | Arg | Gln | Tyr | Leu | Ala | Gln | Trp | Leu | Glu | Lys | Gln | Asp | Trp | |
| | 30 | | | | 35 | | | | 40 | | | | | | | |
| GAG | CAC | GCT | GCC | AAT | GAT | GTT | TCA | TTT | GCC | ACC | ATC | CGT | TTT | CAT | GAC | 373 |
| Glu | His | Ala | Ala | Asn | Asp | Val | Ser | Phe | Ala | Thr | Ile | Arg | Phe | His | Asp | |
| | 45 | | | | 50 | | | | | 55 | | | | | | |
| CTC | CTG | TCA | CAG | CTG | GAT | GAT | CAA | TAT | AGT | CGC | TTT | TCT | TTG | GAG | AAT | 421 |
| Leu | Leu | Ser | Gln | Leu | Asp | Asp | Gln | Tyr | Ser | Arg | Phe | Ser | Leu | Glu | Asn | |
| 60 | | | | 65 | | | | | 70 | | | | | | 75 | |
| AAC | TTC | TTG | CTA | CAG | CAT | AAC | ATA | AGG | AAA | AGC | AAG | CGT | AAT | CTT | CAG | 469 |
| Asn | Phe | Leu | Leu | Gln | His | Asn | Ile | Arg | Lys | Ser | Lys | Arg | Asn | Leu | Gln | |
| | | | | 80 | | | | | 85 | | | | | 90 | | |
| GAT | AAT | TTT | CAG | GAA | GAC | CCA | ATC | CAG | ATG | TCT | ATG | ATC | ATT | TAC | AGC | 517 |
| Asp | Asn | Phe | Gln | Glu | Asp | Pro | Ile | Gln | Met | Ser | Met | Ile | Ile | Tyr | Ser | |
| | | 95 | | | | | 100 | | | | | 105 | | | | |
| TGT | CTG | AAG | GAA | GAA | AGG | AAA | ATT | CTG | GAA | AAC | GCC | CAG | AGA | TTT | AAT | 565 |
| Cys | Leu | Lys | Glu | Glu | Arg | Lys | Ile | Leu | Glu | Asn | Ala | Gln | Arg | Phe | Asn | |
| | | 110 | | | | | 115 | | | | | 120 | | | | |
| CAG | GCT | CAG | TCG | GGG | AAT | ATT | CAG | AGC | ACA | GTG | ATG | TTA | GAC | AAA | CAG | 613 |
| Gln | Ala | Gln | Ser | Gly | Asn | Ile | Gln | Ser | Thr | Val | Met | Leu | Asp | Lys | Gln | |
| | 125 | | | | | 130 | | | | | 135 | | | | | |
| AAA | GAG | CTT | GAC | AGT | AAA | GTC | AGA | AAT | GTG | AAG | GAC | AAG | GTT | ATG | TGT | 661 |
| Lys | Glu | Leu | Asp | Ser | Lys | Val | Arg | Asn | Val | Lys | Asp | Lys | Val | Met | Cys | |
| 140 | | | | | 145 | | | | | 150 | | | | | 155 | |
| ATA | GAG | CAT | GAA | ATC | AAG | AGC | CTG | GAA | GAT | TTA | CAA | GAT | GAA | TAT | GAC | 709 |
| Ile | Glu | His | Glu | Ile | Lys | Ser | Leu | Glu | Asp | Leu | Gln | Asp | Glu | Tyr | Asp | |
| | | | | 160 | | | | | 165 | | | | | 170 | | |
| TTC | AAA | TGC | AAA | ACC | TTG | CAG | AAC | AGA | GAA | CAC | GAG | ACC | AAT | GGT | GTG | 757 |
| Phe | Lys | Cys | Lys | Thr | Leu | Gln | Asn | Arg | Glu | His | Glu | Thr | Asn | Gly | Val | |
| | | | 175 | | | | | 180 | | | | | 185 | | | |
| GCA | AAG | AGT | GAT | CAG | AAA | CAA | GAA | CAG | CTG | TTA | CTC | AAG | AAG | ATG | TAT | 805 |
| Ala | Lys | Ser | Asp | Gln | Lys | Gln | Glu | Gln | Leu | Leu | Leu | Lys | Lys | Met | Tyr | |
| | | | 190 | | | | | 195 | | | | | | 200 | | |
| TTA | ATG | CTT | GAC | AAT | AAG | AGA | AAG | GAA | GTA | GTT | CAC | AAA | ATA | ATA | GAG | 853 |
| Leu | Met | Leu | Asp | Asn | Lys | Arg | Lys | Glu | Val | Val | His | Lys | Ile | Ile | Glu | |
| | 205 | | | | | 210 | | | | | 215 | | | | | |
| TTG | CTG | AAT | GTC | ACT | GAA | CTT | ACC | CAG | AAT | GCC | CTG | ATT | AAT | GAT | GAA | 901 |
| Leu | Leu | Asn | Val | Thr | Glu | Leu | Thr | Gln | Asn | Ala | Leu | Ile | Asn | Asp | Glu | |
| 220 | | | | | 225 | | | | | 230 | | | | | 235 | |
| CTA | GTG | GAG | TGG | AAG | CGG | AGA | CAG | CAG | AGC | GCC | TGT | ATT | GGG | GGG | CCG | 949 |
| Leu | Val | Glu | Trp | Lys | Arg | Arg | Gln | Gln | Ser | Ala | Cys | Ile | Gly | Gly | Pro | |
| | | | 240 | | | | | 245 | | | | | 250 | | | |
| CCC | AAT | GCT | TGC | TTG | GAT | CAG | CTG | CAG | AAC | TGG | TTC | ACT | ATA | GTT | GCG | 997 |
| Pro | Asn | Ala | Cys | Leu | Asp | Gln | Leu | Gln | Asn | Trp | Phe | Thr | Ile | Val | Ala | |
| | | | 255 | | | | | 260 | | | | | 265 | | | |
| GAG | AGT | CTG | CAG | CAA | GTT | CGG | CAG | CAG | CTT | AAA | AAG | TTG | GAG | GAA | TTG | 1045 |
| Glu | Ser | Leu | Gln | Gln | Val | Arg | Gln | Gln | Leu | Lys | Lys | Leu | Glu | Glu | Leu | |
| | | 270 | | | | | 275 | | | | | 280 | | | | |
| GAA | CAG | AAA | TAC | ACC | TAC | GAA | CAT | GAC | CCT | ATC | ACA | AAA | AAC | AAA | CAA | 1093 |
| Glu | Gln | Lys | Tyr | Thr | Tyr | Glu | His | Asp | Pro | Ile | Thr | Lys | Asn | Lys | Gln | |
| | 285 | | | | | 290 | | | | | 295 | | | | | |
| GTG | TTA | TGG | GAC | CGC | ACC | TTC | AGT | CTT | TTC | CAG | CAG | CTC | ATT | CAG | AGC | 1141 |
| Val | Leu | Trp | Asp | Arg | Thr | Phe | Ser | Leu | Phe | Gln | Gln | Leu | Ile | Gln | Ser | |
| 300 | | | | | 305 | | | | | 310 | | | | | 315 | |

```
TCG TTT GTG GTG GAA AGA CAG CCC TGC ATG CCA ACG CAC CCT CAG AGG     1189
Ser Phe Val Val Glu Arg Gln Pro Cys Met Pro Thr His Pro Gln Arg
        320                 325                 330

CCG CTG GTC TTG AAG ACA GGG GTC CAG TTC ACT GTG AAG TTG AGA CTG     1237
Pro Leu Val Leu Lys Thr Gly Val Gln Phe Thr Val Lys Leu Arg Leu
            335                 340                 345

TTG GTG AAA TTG CAA GAG CTG AAT TAT AAT TTG AAA GTC AAA GTC TTA     1285
Leu Val Lys Leu Gln Glu Leu Asn Tyr Asn Leu Lys Val Lys Val Leu
        350                 355                 360

TTT GAT AAA GAT GTG AAT GAG AGA AAT ACA GTA AAA GGA TTT AGG AAG     1333
Phe Asp Lys Asp Val Asn Glu Arg Asn Thr Val Lys Gly Phe Arg Lys
    365                 370                 375

TTC AAC ATT TTG GGC ACG CAC ACA AAA GTG ATG AAC ATG GAG GAG TCC     1381
Phe Asn Ile Leu Gly Thr His Thr Lys Val Met Asn Met Glu Glu Ser
380                 385                 390                 395

ACC AAT GGC AGT CTG GCG GCT GAA TTT CGG CAC CTG CAA TTG AAA GAA     1429
Thr Asn Gly Ser Leu Ala Ala Glu Phe Arg His Leu Gln Leu Lys Glu
                400                 405                 410

CAG AAA AAT GCT GGC ACC AGA ACG AAT GAG GGT CCT CTC ATC GTT ACT     1477
Gln Lys Asn Ala Gly Thr Arg Thr Asn Glu Gly Pro Leu Ile Val Thr
            415                 420                 425

GAA GAG CTT CAC TCC CTT AGT TTT GAA ACC CAA TTG TGC CAG CCT GGT     1525
Glu Glu Leu His Ser Leu Ser Phe Glu Thr Gln Leu Cys Gln Pro Gly
        430                 435                 440

TTG GTA ATT GAC CTC GAG ACG ACC TCT CTG CCC GTT GTG GTG ATC TCC     1573
Leu Val Ile Asp Leu Glu Thr Thr Ser Leu Pro Val Val Val Ile Ser
    445                 450                 455

AAC GTC AGC CAG CTC CCG AGC GGT TGG GCC TCC ATC CTT TGG TAC AAC     1621
Asn Val Ser Gln Leu Pro Ser Gly Trp Ala Ser Ile Leu Trp Tyr Asn
460                 465                 470                 475

ATG CTG GTG GCG GAA CCC AGG AAT CTG TCC TTC TTC CTG ACT CCA CCA     1669
Met Leu Val Ala Glu Pro Arg Asn Leu Ser Phe Phe Leu Thr Pro Pro
                480                 485                 490

TGT GCA CGA TGG GCT CAG CTT TCA GAA GTG CTG AGT TGG CAG TTT TCT     1717
Cys Ala Arg Trp Ala Gln Leu Ser Glu Val Leu Ser Trp Gln Phe Ser
            495                 500                 505

TCT GTC ACC AAA AGA GGT CTC AAT GTG GAC CAG CTG AAC ATG TTG GGA     1765
Ser Val Thr Lys Arg Gly Leu Asn Val Asp Gln Leu Asn Met Leu Gly
        510                 515                 520

GAG AAG CTT CTT GGT CCT AAC GCC AGC CCC GAT GGT CTC ATT CCG TGG     1813
Glu Lys Leu Leu Gly Pro Asn Ala Ser Pro Asp Gly Leu Ile Pro Trp
    525                 530                 535

ACG AGG TTT TGT AAG GAA AAT ATA AAT GAT AAA AAT TTT CCC TTC TGG     1861
Thr Arg Phe Cys Lys Glu Asn Ile Asn Asp Lys Asn Phe Pro Phe Trp
540                 545                 550                 555

CTT TGG ATT GAA AGC ATC CTA GAA CTC ATT AAA AAA CAC CTG CTC CCT     1909
Leu Trp Ile Glu Ser Ile Leu Glu Leu Ile Lys Lys His Leu Leu Pro
                560                 565                 570

CTC TGG AAT GAT GGG TGC ATC ATG GGC TTC ATC AGC AAG GAG CGA GAG     1957
Leu Trp Asn Asp Gly Cys Ile Met Gly Phe Ile Ser Lys Glu Arg Glu
            575                 580                 585

CGT GCC CTG TTG AAG GAC CAG CAG CCG GGG ACC TTC CTG CTG CGG TTC     2005
Arg Ala Leu Leu Lys Asp Gln Gln Pro Gly Thr Phe Leu Leu Arg Phe
        590                 595                 600

AGT GAG AGC TCC CGG GAA GGG GCC ATC ACA TTC ACA TGG GTG GAG CGG     2053
Ser Glu Ser Ser Arg Glu Gly Ala Ile Thr Phe Thr Trp Val Glu Arg
    605                 610                 615

TCC CAG AAC GGA GGC GAA CCT GAC TTC CAT GCG GTT GAA CCC TAC ACG     2101
Ser Gln Asn Gly Gly Glu Pro Asp Phe His Ala Val Glu Pro Tyr Thr
620                 625                 630                 635
```

| | | | | | | | | | | | | | | | | |
|---|---|---|---|---|---|---|---|---|---|---|---|---|---|---|---|---|
| AAG | AAA | GAA | CTT | TCT | GCT | GTT | ACT | TTC | CCT | GAC | ATC | ATT | CGC | AAT | TAC | 2149 |
| Lys | Lys | Glu | Leu | Ser | Ala | Val | Thr | Phe | Pro | Asp | Ile | Ile | Arg | Asn | Tyr | |
| | | | 640 | | | | | 645 | | | | | | 650 | | |
| AAA | GTC | ATG | GCT | GCT | GAG | AAT | ATT | CCT | GAG | AAT | CCC | CTG | AAG | TAT | CTG | 2197 |
| Lys | Val | Met | Ala | Ala | Glu | Asn | Ile | Pro | Glu | Asn | Pro | Leu | Lys | Tyr | Leu | |
| | | 655 | | | | | | 660 | | | | | 665 | | | |
| TAT | CCA | AAT | ATT | GAC | AAA | GAC | CAT | GCC | TTT | GGA | AAG | TAT | TAC | TCC | AGG | 2245 |
| Tyr | Pro | Asn | Ile | Asp | Lys | Asp | His | Ala | Phe | Gly | Lys | Tyr | Tyr | Ser | Arg | |
| | | 670 | | | | | 675 | | | | | 680 | | | | |
| CCA | AAG | GAA | GCA | CCA | GAG | CCA | ATG | GAA | CTT | GAT | GGC | CCT | AAA | GGA | ACT | 2293 |
| Pro | Lys | Glu | Ala | Pro | Glu | Pro | Met | Glu | Leu | Asp | Gly | Pro | Lys | Gly | Thr | |
| | 685 | | | | 690 | | | | | 695 | | | | | | |
| GGA | TAT | ATC | AAG | ACT | GAG | TTG | ATT | TCT | GTG | TCT | GAA | GTT | CAC | CCT | TCT | 2341 |
| Gly | Tyr | Ile | Lys | Thr | Glu | Leu | Ile | Ser | Val | Ser | Glu | Val | His | Pro | Ser | |
| 700 | | | | | 705 | | | | 710 | | | | | | 715 | |
| AGA | CTT | CAG | ACC | ACA | GAC | AAC | CTG | CTC | CCC | ATG | TCT | CCT | GAG | GAG | TTT | 2389 |
| Arg | Leu | Gln | Thr | Thr | Asp | Asn | Leu | Leu | Pro | Met | Ser | Pro | Glu | Glu | Phe | |
| | | | 720 | | | | | | 725 | | | | | 730 | | |
| GAC | GAG | GTG | TCT | CGG | ATA | GTG | GGC | TCT | GTA | GAA | TTC | GAC | AGT | ATG | ATG | 2437 |
| Asp | Glu | Val | Ser | Arg | Ile | Val | Gly | Ser | Val | Glu | Phe | Asp | Ser | Met | Met | |
| | | | 735 | | | | | 740 | | | | | 745 | | | |
| AAC | ACA | GTA | TAGAGCATGA | AATTTTTTCA | TCTTCTCTGG | CGACAGTTTT | | | | | | | | | | 2486 |
| Asn | Thr | Val | | | | | | | | | | | | | | |
| | | 750 | | | | | | | | | | | | | | |

```
CCTTCTCATC  TGTGATTCCC  TCCTGCTACT  CTGTTCCTTC  ACATCCTGTG  TTTCTAGG    2546
AATGAAAGAA  AGGCCAGCAA  ATTCGCTGCA  ACCTGTTGAT  AGCAAGTGAA  TTTTTCTC    2606
ACTCAGAAAC  ATCAGTTACT  CTGAAGGGCA  TCATGCATCT  TACTGAAGGT  AAAATTGA    2666
GGCATTCTCT  GAAGAGTGGG  TTTCACAAGT  GAAAAACATC  CAGATACACC  CAAAGTAT    2726
GGACGAGAAT  GAGGGTCCTT  TGGGAAGGA   GAAGTTAAGC  AACATCAGC   AAATGTTA    2786
CATAAAGTCA  GTGCCCAACT  GTTATAGGTT  GTTGGATAAA  TCAGTGGTTA  TTTAGGA     2846
TGCTTGACGT  AGGAACGGTA  AATTTCTGTG  GGAGAATTCT  TACATGTTTT  CTTTGCTT    2906
AGTGTAACTG  GCAGTTTTCC  ATTGGTTTAC  CTGTGAAATA  GTTCAAAGCC  AAGTTTAT    2966
ACAATTATAT  CAGTCCTCTT  TCAAGGTAG   CCATCATGGA  TCTGGTAGGG  GGAAAATG    3026
TATTTTATTA  CATCTTTCAC  ATTGGCTATT  TAAAGACAAA  GACAAATTCT  GTTCTTG     3086
AAGAGAACAT  TTCCAAATTC  ACAAGTTGTG  TTTGATATCC  AAAGCTGAAT  ACATTCTG    3146
TTCATCTTGG  TCACATACAA  TTATTTTTAC  AGTTCTCCCA  AGGGAGTTAG  GCTATTCA    3206
ACCACTCATT  CAAAAGTTGA  AATTAACCAT  AGATGTAGAT  AAACTCAGAA  ATTTAATT    3266
TGTTTCTTAA  ATGGGCTACT  TTGTCCTTTT  TGTTATTAGG  GTGGTATTTA  GTCTATTA    3326
CACAAAATTG  GGAAAGGAGT  AGAAAAAGCA  GTAACTGACA  ACTTGAATAA  TACACCAG    3386
ATAATATGAG  AATCAGATCA  TTTCAAAACT  CATTTCCTAT  GTAACTGCAT  TGAGAACT    3446
ATATGTTTCG  CTGATATATG  TGTTTTTCAC  ATTTGCGAAT  GGTTCCATTC  TCTCTCCT    3506
ACTTTTTCCA  GACACTTTTT  TGAGTGGATG  ATGTTTCGTG  AAGTATACTG  TATTTTTA    3566
TTTTTCCTTC  CTTATCACTG  ACACAAAAAG  TAGATTAAGA  GATGGGTTTG  ACAAGGTT    3626
TCCCTTTTAC  ATACTGCTGT  CTATGTGGCT  GTATCTTGTT  TTTCCACTAC  TGCTACCA    3686
ACTATATTAT  CATGCAAATG  CTGTATTCTT  CTTTGGTGGA  GATAAAGATT  TCTTGAGT    3746
TGTTTAAAA   TTAAAGCTAA  AGTATCTGTA  TTGCATTAAA  TATAATATCG  ACACAGTG    3806
TTCCGTGGCA  CTGCATACAA  TCTGAGGCCT  CCTCTCTCAG  TTTTTATATA  GATGGCGA    3866
ACCTAAGTTT  CAGTTGATTT  TACAATTGAA  ATGACTAAAA  AACAAAGAAG  ACAACATT    3926
```

AAACAATATT GTTTCTA 3943

(2) INFORMATION FOR SEQ ID NO:4:

(i) SEQUENCE CHARACTERISTICS:
        (A) LENGTH: 750 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ser Gln Trp Tyr Glu Leu Gln Gln Leu Asp Ser Lys Phe Leu Glu
 1               5                  10                  15
Gln Val His Gln Leu Tyr Asp Asp Ser Phe Pro Met Glu Ile Arg Gln
            20                  25                  30
Tyr Leu Ala Gln Trp Leu Glu Lys Gln Asp Trp Glu His Ala Ala Asn
        35                  40                  45
Asp Val Ser Phe Ala Thr Ile Arg Phe His Asp Leu Leu Ser Gln Leu
    50                  55                  60
Asp Asp Gln Tyr Ser Arg Phe Ser Leu Glu Asn Asn Phe Leu Leu Gln
 65                  70                  75                  80
His Asn Ile Arg Lys Ser Lys Arg Asn Leu Gln Asp Asn Phe Gln Glu
                85                  90                  95
Asp Pro Ile Gln Met Ser Met Ile Ile Tyr Ser Cys Leu Lys Glu Glu
            100                 105                 110
Arg Lys Ile Leu Glu Asn Ala Gln Arg Phe Asn Gln Ala Gln Ser Gly
        115                 120                 125
Asn Ile Gln Ser Thr Val Met Leu Asp Lys Gln Lys Glu Leu Asp Ser
    130                 135                 140
Lys Val Arg Asn Val Lys Asp Lys Val Met Cys Ile Glu His Glu Ile
145                 150                 155                 160
Lys Ser Leu Glu Asp Leu Gln Asp Glu Tyr Asp Phe Lys Cys Lys Thr
                165                 170                 175
Leu Gln Asn Arg Glu His Glu Thr Asn Gly Val Ala Lys Ser Asp Gln
            180                 185                 190
Lys Gln Glu Gln Leu Leu Leu Lys Lys Met Tyr Leu Met Leu Asp Asn
        195                 200                 205
Lys Arg Lys Glu Val Val His Lys Ile Ile Glu Leu Leu Asn Val Thr
    210                 215                 220
Glu Leu Thr Gln Asn Ala Leu Ile Asn Asp Glu Leu Val Glu Trp Lys
225                 230                 235                 240
Arg Arg Gln Gln Ser Ala Cys Ile Gly Gly Pro Pro Asn Ala Cys Leu
                245                 250                 255
Asp Gln Leu Gln Asn Trp Phe Thr Ile Val Ala Glu Ser Leu Gln Gln
            260                 265                 270
Val Arg Gln Gln Leu Lys Lys Leu Glu Glu Leu Glu Gln Lys Tyr Thr
        275                 280                 285
Tyr Glu His Asp Pro Ile Thr Lys Asn Lys Gln Val Leu Trp Asp Arg
    290                 295                 300
Thr Phe Ser Leu Phe Gln Gln Leu Ile Gln Ser Ser Phe Val Val Glu
305                 310                 315                 320
Arg Gln Pro Cys Met Pro Thr His Pro Gln Arg Pro Leu Val Leu Lys
                325                 330                 335
Thr Gly Val Gln Phe Thr Val Lys Leu Arg Leu Leu Val Lys Leu Gln
            340                 345                 350
```

```
Glu  Leu  Asn  Tyr  Asn  Leu  Lys  Val  Lys  Val  Leu  Phe  Asp  Lys  Asp  Val
          355                 360                      365

Asn  Glu  Arg  Asn  Thr  Val  Lys  Gly  Phe  Arg  Lys  Phe  Asn  Ile  Leu  Gly
     370                      375                      380

Thr  His  Thr  Lys  Val  Met  Asn  Met  Glu  Glu  Ser  Thr  Asn  Gly  Ser  Leu
385                      390                      395                      400

Ala  Ala  Glu  Phe  Arg  His  Leu  Gln  Leu  Lys  Glu  Gln  Lys  Asn  Ala  Gly
                    405                      410                      415

Thr  Arg  Thr  Asn  Glu  Gly  Pro  Leu  Ile  Val  Thr  Glu  Glu  Leu  His  Ser
               420                      425                      430

Leu  Ser  Phe  Glu  Thr  Gln  Leu  Cys  Gln  Pro  Gly  Leu  Val  Ile  Asp  Leu
          435                      440                      445

Glu  Thr  Thr  Ser  Leu  Pro  Val  Val  Ile  Ser  Asn  Val  Ser  Gln  Leu
     450                      455                      460

Pro  Ser  Gly  Trp  Ala  Ser  Ile  Leu  Trp  Tyr  Asn  Met  Leu  Val  Ala  Glu
465                      470                      475                      480

Pro  Arg  Asn  Leu  Ser  Phe  Phe  Leu  Thr  Pro  Pro  Cys  Ala  Arg  Trp  Ala
                    485                      490                      495

Gln  Leu  Ser  Glu  Val  Leu  Ser  Trp  Gln  Phe  Ser  Ser  Val  Thr  Lys  Arg
               500                      505                      510

Gly  Leu  Asn  Val  Asp  Gln  Leu  Asn  Met  Leu  Gly  Glu  Lys  Leu  Leu  Gly
               515                      520                      525

Pro  Asn  Ala  Ser  Pro  Asp  Gly  Leu  Ile  Pro  Trp  Thr  Arg  Phe  Cys  Lys
     530                      535                      540

Glu  Asn  Ile  Asn  Asp  Lys  Asn  Phe  Pro  Phe  Trp  Leu  Trp  Ile  Glu  Ser
545                      550                      555                      560

Ile  Leu  Glu  Leu  Ile  Lys  Lys  His  Leu  Leu  Pro  Leu  Trp  Asn  Asp  Gly
                    565                      570                      575

Cys  Ile  Met  Gly  Phe  Ile  Ser  Lys  Glu  Arg  Glu  Arg  Ala  Leu  Leu  Lys
               580                      585                      590

Asp  Gln  Gln  Pro  Gly  Thr  Phe  Leu  Leu  Arg  Phe  Ser  Glu  Ser  Ser  Arg
          595                      600                      605

Glu  Gly  Ala  Ile  Thr  Phe  Thr  Trp  Val  Glu  Arg  Ser  Gln  Asn  Gly  Gly
     610                      615                      620

Glu  Pro  Asp  Phe  His  Ala  Val  Glu  Pro  Tyr  Thr  Lys  Lys  Glu  Leu  Ser
625                      630                      635                      640

Ala  Val  Thr  Phe  Pro  Asp  Ile  Ile  Arg  Asn  Tyr  Lys  Val  Met  Ala  Ala
                    645                      650                      655

Glu  Asn  Ile  Pro  Glu  Asn  Pro  Leu  Lys  Tyr  Leu  Tyr  Pro  Asn  Ile  Asp
               660                      665                      670

Lys  Asp  His  Ala  Phe  Gly  Lys  Tyr  Tyr  Ser  Arg  Pro  Lys  Glu  Ala  Pro
          675                      680                      685

Glu  Pro  Met  Glu  Leu  Asp  Gly  Pro  Lys  Gly  Thr  Gly  Tyr  Ile  Lys  Thr
     690                      695                      700

Glu  Leu  Ile  Ser  Val  Ser  Glu  Val  His  Pro  Ser  Arg  Leu  Gln  Thr  Thr
705                      710                      715                      720

Asp  Asn  Leu  Leu  Pro  Met  Ser  Pro  Glu  Glu  Phe  Asp  Glu  Val  Ser  Arg
                    725                      730                      735

Ile  Val  Gly  Ser  Val  Glu  Phe  Asp  Ser  Met  Met  Asn  Thr  Val
               740                      745                      750
```

( 2 ) INFORMATION FOR SEQ ID NO:5:

( i ) SEQUENCE CHARACTERISTICS:

(A) LENGTH: 2607 base pairs
(B) TYPE: nucleic acid
(C) STRANDEDNESS: both
(D) TOPOLOGY: unknown (ii) MOLECULE TYPE: cDNA (iii) HYPOTHETICAL: NO (iv) ANTI-SENSE: NO (vi) ORIGINAL SOURCE:
(A) ORGANISM: Homo sapiens (ix) FEATURE:
(A) NAME/KEY: CDS
(B) LOCATION: 197..2335

(xi) SEQUENCE DESCRIPTION: SEQ ID NO:5:

```
ATTAAACCTC TCGCCGAGCC CCTCCGCAGA CTCTGCGCCG GAAAGTTTCA TTTGCTGTAT    60

GCCATCCTCG AGAGCTGTCT AGGTTAACGT TCGCACTCTG TGTATATAAC CTCGACAGTC   120

TTGGCACCTA ACGTGCTGTG CGTAGCTGCT CCTTTGGTTG AATCCCCAGG CCCTTGTTGG   180

GGCACAAGGT GGCAGG ATG TCT CAG TGG TAC GAA CTT CAG CAG CTT GAC       229
               Met Ser Gln Trp Tyr Glu Leu Gln Gln Leu Asp
                 1               5                  10

TCA AAA TTC CTG GAG CAG GTT CAC CAG CTT TAT GAT GAC AGT TTT CCC    277
Ser Lys Phe Leu Glu Gln Val His Gln Leu Tyr Asp Asp Ser Phe Pro
         15                  20                  25

ATG GAA ATC AGA CAG TAC CTG GCA CAG TGG TTA GAA AAG CAA GAC TGG    325
Met Glu Ile Arg Gln Tyr Leu Ala Gln Trp Leu Glu Lys Gln Asp Trp
         30                  35                  40

GAG CAC GCT GCC AAT GAT GTT TCA TTT GCC ACC ATC CGT TTT CAT GAC    373
Glu His Ala Ala Asn Asp Val Ser Phe Ala Thr Ile Arg Phe His Asp
     45                  50                  55

CTC CTG TCA CAG CTG GAT GAT CAA TAT AGT CGC TTT TCT TTG GAG AAT    421
Leu Leu Ser Gln Leu Asp Asp Gln Tyr Ser Arg Phe Ser Leu Glu Asn
60                  65                  70                  75

AAC TTC TTG CTA CAG CAT AAC ATA AGG AAA AGC AAG CGT AAT CTT CAG    469
Asn Phe Leu Leu Gln His Asn Ile Arg Lys Ser Lys Arg Asn Leu Gln
         80                  85                  90

GAT AAT TTT CAG GAA GAC CCA ATC CAG ATG TCT ATG ATC ATT TAC AGC    517
Asp Asn Phe Gln Glu Asp Pro Ile Gln Met Ser Met Ile Ile Tyr Ser
         95                 100                 105

TGT CTG AAG GAA GAA AGG AAA ATT CTG GAA AAC GCC CAG AGA TTT AAT    565
Cys Leu Lys Glu Glu Arg Lys Ile Leu Glu Asn Ala Gln Arg Phe Asn
        110                 115                 120

CAG GCT CAG TCG GGG AAT ATT CAG AGC ACA GTG ATG TTA GAC AAA CAG    613
Gln Ala Gln Ser Gly Asn Ile Gln Ser Thr Val Met Leu Asp Lys Gln
        125                 130                 135

AAA GAG CTT GAC AGT AAA GTC AGA AAT GTG AAG GAC AAG GTT ATG TGT    661
Lys Glu Leu Asp Ser Lys Val Arg Asn Val Lys Asp Lys Val Met Cys
140                 145                 150                 155

ATA GAG CAT GAA ATC AAG AGC CTG GAA GAT TTA CAA GAT GAA TAT GAC    709
Ile Glu His Glu Ile Lys Ser Leu Glu Asp Leu Gln Asp Glu Tyr Asp
            160                 165                 170

TTC AAA TGC AAA ACC TTG CAG AAC AGA GAA CAC GAG ACC AAT GGT GTG    757
Phe Lys Cys Lys Thr Leu Gln Asn Arg Glu His Glu Thr Asn Gly Val
            175                 180                 185

GCA AAG AGT GAT CAG AAA CAA GAA CAG CTG TTA CTC AAG AAG ATG TAT    805
Ala Lys Ser Asp Gln Lys Gln Glu Gln Leu Leu Leu Lys Lys Met Tyr
        190                 195                 200

TTA ATG CTT GAC AAT AAG AGA AAG GAA GTA GTT CAC AAA ATA ATA GAG    853
Leu Met Leu Asp Asn Lys Arg Lys Glu Val Val His Lys Ile Ile Glu
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 205 |     |     |     |     | 210 |     |     |     |     | 215 |     |     |      |
| TTG | CTG | AAT | GTC | ACT | GAA | CTT | ACC | CAG | AAT | GCC | CTG | ATT | AAT | GAT | GAA | 901  |
| Leu | Leu | Asn | Val | Thr | Glu | Leu | Thr | Gln | Asn | Ala | Leu | Ile | Asn | Asp | Glu |      |
| 220 |     |     |     |     | 225 |     |     |     |     | 230 |     |     |     |     | 235 |      |
| CTA | GTG | GAG | TGG | AAG | CGG | AGA | CAG | CAG | AGC | GCC | TGT | ATT | GGG | GGG | CCG | 949  |
| Leu | Val | Glu | Trp | Lys | Arg | Arg | Gln | Gln | Ser | Ala | Cys | Ile | Gly | Gly | Pro |      |
|     |     |     |     | 240 |     |     |     |     | 245 |     |     |     |     | 250 |     |      |
| CCC | AAT | GCT | TGC | TTG | GAT | CAG | CTG | CAG | AAC | TGG | TTC | ACT | ATA | GTT | GCG | 997  |
| Pro | Asn | Ala | Cys | Leu | Asp | Gln | Leu | Gln | Asn | Trp | Phe | Thr | Ile | Val | Ala |      |
|     |     |     | 255 |     |     |     |     | 260 |     |     |     |     | 265 |     |     |      |
| GAG | AGT | CTG | CAG | CAA | GTT | CGG | CAG | CAG | CTT | AAA | AAG | TTG | GAG | GAA | TTG | 1045 |
| Glu | Ser | Leu | Gln | Gln | Val | Arg | Gln | Gln | Leu | Lys | Lys | Leu | Glu | Glu | Leu |      |
|     |     | 270 |     |     |     |     | 275 |     |     |     |     | 280 |     |     |     |      |
| GAA | CAG | AAA | TAC | ACC | TAC | GAA | CAT | GAC | CCT | ATC | ACA | AAA | AAC | AAA | CAA | 1093 |
| Glu | Gln | Lys | Tyr | Thr | Tyr | Glu | His | Asp | Pro | Ile | Thr | Lys | Asn | Lys | Gln |      |
|     | 285 |     |     |     |     | 290 |     |     |     |     | 295 |     |     |     |     |      |
| GTG | TTA | TGG | GAC | CGC | ACC | TTC | AGT | CTT | TTC | CAG | CAG | CTC | ATT | CAG | AGC | 1141 |
| Val | Leu | Trp | Asp | Arg | Thr | Phe | Ser | Leu | Phe | Gln | Gln | Leu | Ile | Gln | Ser |      |
| 300 |     |     |     |     | 305 |     |     |     |     | 310 |     |     |     |     | 315 |      |
| TCG | TTT | GTG | GTG | GAA | AGA | CAG | CCC | TGC | ATG | CCA | ACG | CAC | CCT | CAG | AGG | 1189 |
| Ser | Phe | Val | Val | Glu | Arg | Gln | Pro | Cys | Met | Pro | Thr | His | Pro | Gln | Arg |      |
|     |     |     |     | 320 |     |     |     |     | 325 |     |     |     |     | 330 |     |      |
| CCG | CTG | GTC | TTG | AAG | ACA | GGG | GTC | CAG | TTC | ACT | GTG | AAG | TTG | AGA | CTG | 1237 |
| Pro | Leu | Val | Leu | Lys | Thr | Gly | Val | Gln | Phe | Thr | Val | Lys | Leu | Arg | Leu |      |
|     |     |     | 335 |     |     |     |     | 340 |     |     |     |     | 345 |     |     |      |
| TTG | GTG | AAA | TTG | CAA | GAG | CTG | AAT | TAT | AAT | TTG | AAA | GTC | AAA | GTC | TTA | 1285 |
| Leu | Val | Lys | Leu | Gln | Glu | Leu | Asn | Tyr | Asn | Leu | Lys | Val | Lys | Val | Leu |      |
|     |     | 350 |     |     |     |     | 355 |     |     |     |     | 360 |     |     |     |      |
| TTT | GAT | AAA | GAT | GTG | AAT | GAG | AGA | AAT | ACA | GTA | AAA | GGA | TTT | AGG | AAG | 1333 |
| Phe | Asp | Lys | Asp | Val | Asn | Glu | Arg | Asn | Thr | Val | Lys | Gly | Phe | Arg | Lys |      |
|     | 365 |     |     |     |     | 370 |     |     |     |     | 375 |     |     |     |     |      |
| TTC | AAC | ATT | TTG | GGC | ACG | CAC | ACA | AAA | GTG | ATG | AAC | ATG | GAG | GAG | TCC | 1381 |
| Phe | Asn | Ile | Leu | Gly | Thr | His | Thr | Lys | Val | Met | Asn | Met | Glu | Glu | Ser |      |
| 380 |     |     |     |     | 385 |     |     |     |     | 390 |     |     |     |     | 395 |      |
| ACC | AAT | GGC | AGT | CTG | GCG | GCT | GAA | TTT | CGG | CAC | CTG | CAA | TTG | AAA | GAA | 1429 |
| Thr | Asn | Gly | Ser | Leu | Ala | Ala | Glu | Phe | Arg | His | Leu | Gln | Leu | Lys | Glu |      |
|     |     |     |     | 400 |     |     |     |     | 405 |     |     |     |     | 410 |     |      |
| CAG | AAA | AAT | GCT | GGC | ACC | AGA | ACG | AAT | GAG | GGT | CCT | CTC | ATC | GTT | ACT | 1477 |
| Gln | Lys | Asn | Ala | Gly | Thr | Arg | Thr | Asn | Glu | Gly | Pro | Leu | Ile | Val | Thr |      |
|     |     |     | 415 |     |     |     |     | 420 |     |     |     |     | 425 |     |     |      |
| GAA | GAG | CTT | CAC | TCC | CTT | AGT | TTT | GAA | ACC | CAA | TTG | TGC | CAG | CCT | GGT | 1525 |
| Glu | Glu | Leu | His | Ser | Leu | Ser | Phe | Glu | Thr | Gln | Leu | Cys | Gln | Pro | Gly |      |
|     |     | 430 |     |     |     |     | 435 |     |     |     |     | 440 |     |     |     |      |
| TTG | GTA | ATT | GAC | CTC | GAG | ACG | ACC | TCT | CTG | CCC | GTT | GTG | GTG | ATC | TCC | 1573 |
| Leu | Val | Ile | Asp | Leu | Glu | Thr | Thr | Ser | Leu | Pro | Val | Val | Val | Ile | Ser |      |
|     | 445 |     |     |     |     | 450 |     |     |     |     | 455 |     |     |     |     |      |
| AAC | GTC | AGC | CAG | CTC | CCG | AGC | GGT | TGG | GCC | TCC | ATC | CTT | TGG | TAC | AAC | 1621 |
| Asn | Val | Ser | Gln | Leu | Pro | Ser | Gly | Trp | Ala | Ser | Ile | Leu | Trp | Tyr | Asn |      |
| 460 |     |     |     |     | 465 |     |     |     |     | 470 |     |     |     |     | 475 |      |
| ATG | CTG | GTG | GCG | GAA | CCC | AGG | AAT | CTG | TCC | TTC | TTC | CTG | ACT | CCA | CCA | 1669 |
| Met | Leu | Val | Ala | Glu | Pro | Arg | Asn | Leu | Ser | Phe | Phe | Leu | Thr | Pro | Pro |      |
|     |     |     |     | 480 |     |     |     |     | 485 |     |     |     |     | 490 |     |      |
| TGT | GCA | CGA | TGG | GCT | CAG | CTT | TCA | GAA | GTG | CTG | AGT | TGG | CAG | TTT | TCT | 1717 |
| Cys | Ala | Arg | Trp | Ala | Gln | Leu | Ser | Glu | Val | Leu | Ser | Trp | Gln | Phe | Ser |      |
|     |     |     | 495 |     |     |     |     | 500 |     |     |     |     | 505 |     |     |      |
| TCT | GTC | ACC | AAA | AGA | GGT | CTC | AAT | GTG | GAC | CAG | CTG | AAC | ATG | TTG | GGA | 1765 |
| Ser | Val | Thr | Lys | Arg | Gly | Leu | Asn | Val | Asp | Gln | Leu | Asn | Met | Leu | Gly |      |
|     |     | 510 |     |     |     |     | 515 |     |     |     |     | 520 |     |     |     |      |
| GAG | AAG | CTT | CTT | GGT | CCT | AAC | GCC | AGC | CCC | GAT | GGT | CTC | ATT | CCG | TGG | 1813 |
| Glu | Lys | Leu | Leu | Gly | Pro | Asn | Ala | Ser | Pro | Asp | Gly | Leu | Ile | Pro | Trp |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 525 |     |     |     |     | 530 |     |     |     |     | 535 |     |     |     |      |
| ACG | AGG | TTT | TGT | AAG | GAA | AAT | ATA | AAT | GAT | AAA | AAT | TTT | CCC | TTC | TGG | 1861 |
| Thr | Arg | Phe | Cys | Lys | Glu | Asn | Ile | Asn | Asp | Lys | Asn | Phe | Pro | Phe | Trp |      |
| 540 |     |     |     | 545 |     |     |     |     | 550 |     |     |     |     |     | 555 |      |
| CTT | TGG | ATT | GAA | AGC | ATC | CTA | GAA | CTC | ATT | AAA | AAA | CAC | CTG | CTC | CCT | 1909 |
| Leu | Trp | Ile | Glu | Ser | Ile | Leu | Glu | Leu | Ile | Lys | Lys | His | Leu | Leu | Pro |      |
|     |     |     |     | 560 |     |     |     |     | 565 |     |     |     |     | 570 |     |      |
| CTC | TGG | AAT | GAT | GGG | TGC | ATC | ATG | GGC | TTC | ATC | AGC | AAG | GAG | CGA | GAG | 1957 |
| Leu | Trp | Asn | Asp | Gly | Cys | Ile | Met | Gly | Phe | Ile | Ser | Lys | Glu | Arg | Glu |      |
|     |     |     | 575 |     |     |     |     | 580 |     |     |     |     | 585 |     |     |      |
| CGT | GCC | CTG | TTG | AAG | GAC | CAG | CAG | CCG | GGG | ACC | TTC | CTG | CTG | CGG | TTC | 2005 |
| Arg | Ala | Leu | Leu | Lys | Asp | Gln | Gln | Pro | Gly | Thr | Phe | Leu | Leu | Arg | Phe |      |
|     |     | 590 |     |     |     |     | 595 |     |     |     |     | 600 |     |     |     |      |
| AGT | GAG | AGC | TCC | CGG | GAA | GGG | GCC | ATC | ACA | TTC | ACA | TGG | GTG | GAG | CGG | 2053 |
| Ser | Glu | Ser | Ser | Arg | Glu | Gly | Ala | Ile | Thr | Phe | Thr | Trp | Val | Glu | Arg |      |
|     |     | 605 |     |     |     |     | 610 |     |     |     |     | 615 |     |     |     |      |
| TCC | CAG | AAC | GGA | GGC | GAA | CCT | GAC | TTC | CAT | GCG | GTT | GAA | CCC | TAC | ACG | 2101 |
| Ser | Gln | Asn | Gly | Gly | Glu | Pro | Asp | Phe | His | Ala | Val | Glu | Pro | Tyr | Thr |      |
| 620 |     |     |     |     | 625 |     |     |     |     | 630 |     |     |     |     | 635 |      |
| AAG | AAA | GAA | CTT | TCT | GCT | GTT | ACT | TTC | CCT | GAC | ATC | ATT | CGC | AAT | TAC | 2149 |
| Lys | Lys | Glu | Leu | Ser | Ala | Val | Thr | Phe | Pro | Asp | Ile | Ile | Arg | Asn | Tyr |      |
|     |     |     |     | 640 |     |     |     |     | 645 |     |     |     |     | 650 |     |      |
| AAA | GTC | ATG | GCT | GCT | GAG | AAT | ATT | CCT | GAG | AAT | CCC | CTG | AAG | TAT | CTG | 2197 |
| Lys | Val | Met | Ala | Ala | Glu | Asn | Ile | Pro | Glu | Asn | Pro | Leu | Lys | Tyr | Leu |      |
|     |     |     | 655 |     |     |     |     | 660 |     |     |     |     | 665 |     |     |      |
| TAT | CCA | AAT | ATT | GAC | AAA | GAC | CAT | GCC | TTT | GGA | AAG | TAT | TAC | TCC | AGG | 2245 |
| Tyr | Pro | Asn | Ile | Asp | Lys | Asp | His | Ala | Phe | Gly | Lys | Tyr | Tyr | Ser | Arg |      |
|     |     | 670 |     |     |     |     | 675 |     |     |     |     | 680 |     |     |     |      |
| CCA | AAG | GAA | GCA | CCA | GAG | CCA | ATG | GAA | CTT | GAT | GGC | CCT | AAA | GGA | ACT | 2293 |
| Pro | Lys | Glu | Ala | Pro | Glu | Pro | Met | Glu | Leu | Asp | Gly | Pro | Lys | Gly | Thr |      |
| 685 |     |     |     |     | 690 |     |     |     |     | 695 |     |     |     |     |     |      |
| GGA | TAT | ATC | AAG | ACT | GAG | TTG | ATT | TCT | GTG | TCT | GAA | GTG | TAAGTGAACA |  |  | 2342 |
| Gly | Tyr | Ile | Lys | Thr | Glu | Leu | Ile | Ser | Val | Ser | Glu | Val |     |     |     |      |
| 700 |     |     |     |     | 705 |     |     |     |     | 710 |     |     |     |     |     |      |

```
CAGAAGAGTG ACATGTTTAC AAACCTCAAG CCAGCCTTGC TCCTGGCTGG GGCCTGTT      2402

AGATGCTTGT ATTTTACTTT TCCATTGTAA TTGCTATCGC CATCACAGCT GAACTTGT      2462

AGATCCCCGT GTTACTGCCT ATCAGCATTT TACTACTTTA AAAAAAAAAA AAAAAGCC      2522

AAACCAAATT TGTATTTAAG GTATATAAAT TTTCCCAAAA CTGATACCCT TTGAAAAA      2582

ATAAATAAAA TGAGCAAAAG TTGAA                                          2607
```

( 2 ) INFORMATION FOR SEQ ID NO:6:

( i ) SEQUENCE CHARACTERISTICS:
        ( A ) LENGTH: 712 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Ser Gln Trp Tyr Glu Leu Gln Gln Leu Asp Ser Lys Phe Leu Glu
 1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Asn
        35                  40                  45

Asp Val Ser Phe Ala Thr Ile Arg Phe His Asp Leu Leu Ser Gln Leu
    50                  55                  60
```

-continued

| | | | | | | | | | | | | | | | |
|---|---|---|---|---|---|---|---|---|---|---|---|---|---|---|---|
| Asp | Asp | Gln | Tyr | Ser | Arg | Phe | Ser | Leu | Glu | Asn | Asn | Phe | Leu | Leu | Gln |
| 65 | | | | | 70 | | | | 75 | | | | | | 80 |
| His | Asn | Ile | Arg | Lys | Ser | Lys | Arg | Asn | Leu | Gln | Asp | Asn | Phe | Gln | Glu |
| | | | | 85 | | | | | 90 | | | | | 95 | |
| Asp | Pro | Ile | Gln | Met | Ser | Met | Ile | Ile | Tyr | Ser | Cys | Leu | Lys | Glu | Glu |
| | | | 100 | | | | | 105 | | | | | 110 | | |
| Arg | Lys | Ile | Leu | Glu | Asn | Ala | Gln | Arg | Phe | Asn | Gln | Ala | Gln | Ser | Gly |
| | | 115 | | | | | 120 | | | | | 125 | | | |
| Asn | Ile | Gln | Ser | Thr | Val | Met | Leu | Asp | Lys | Gln | Lys | Glu | Leu | Asp | Ser |
| 130 | | | | | 135 | | | | | 140 | | | | | |
| Lys | Val | Arg | Asn | Val | Lys | Asp | Lys | Val | Met | Cys | Ile | Glu | His | Glu | Ile |
| 145 | | | | 150 | | | | | 155 | | | | | | 160 |
| Lys | Ser | Leu | Glu | Asp | Leu | Gln | Asp | Glu | Tyr | Asp | Phe | Lys | Cys | Lys | Thr |
| | | | | 165 | | | | | 170 | | | | | 175 | |
| Leu | Gln | Asn | Arg | Glu | His | Glu | Thr | Asn | Gly | Val | Ala | Lys | Ser | Asp | Gln |
| | | | 180 | | | | | 185 | | | | | 190 | | |
| Lys | Gln | Glu | Gln | Leu | Leu | Leu | Lys | Lys | Met | Tyr | Leu | Met | Leu | Asp | Asn |
| | | 195 | | | | | 200 | | | | | 205 | | | |
| Lys | Arg | Lys | Glu | Val | Val | His | Lys | Ile | Ile | Glu | Leu | Leu | Asn | Val | Thr |
| | 210 | | | | | 215 | | | | | 220 | | | | |
| Glu | Leu | Thr | Gln | Asn | Ala | Leu | Ile | Asn | Asp | Glu | Leu | Val | Glu | Trp | Lys |
| 225 | | | | | 230 | | | | | 235 | | | | | 240 |
| Arg | Arg | Gln | Gln | Ser | Ala | Cys | Ile | Gly | Gly | Pro | Pro | Asn | Ala | Cys | Leu |
| | | | | 245 | | | | | 250 | | | | | 255 | |
| Asp | Gln | Leu | Gln | Asn | Trp | Phe | Thr | Ile | Val | Ala | Glu | Ser | Leu | Gln | Gln |
| | | | 260 | | | | | 265 | | | | | 270 | | |
| Val | Arg | Gln | Gln | Leu | Lys | Lys | Leu | Glu | Glu | Leu | Glu | Gln | Lys | Tyr | Thr |
| | | 275 | | | | | 280 | | | | | 285 | | | |
| Tyr | Glu | His | Asp | Pro | Ile | Thr | Lys | Asn | Lys | Gln | Val | Leu | Trp | Asp | Arg |
| | 290 | | | | | 295 | | | | | 300 | | | | |
| Thr | Phe | Ser | Leu | Phe | Gln | Gln | Leu | Ile | Gln | Ser | Ser | Phe | Val | Val | Glu |
| 305 | | | | | 310 | | | | | 315 | | | | | 320 |
| Arg | Gln | Pro | Cys | Met | Pro | Thr | His | Pro | Gln | Arg | Pro | Leu | Val | Leu | Lys |
| | | | | 325 | | | | | 330 | | | | | 335 | |
| Thr | Gly | Val | Gln | Phe | Thr | Val | Lys | Leu | Arg | Leu | Leu | Val | Lys | Leu | Gln |
| | | | 340 | | | | | 345 | | | | | 350 | | |
| Glu | Leu | Asn | Tyr | Asn | Leu | Lys | Val | Lys | Val | Leu | Phe | Asp | Lys | Asp | Val |
| | | 355 | | | | | 360 | | | | | 365 | | | |
| Asn | Glu | Arg | Asn | Thr | Val | Lys | Gly | Phe | Arg | Lys | Phe | Asn | Ile | Leu | Gly |
| | 370 | | | | | 375 | | | | | 380 | | | | |
| Thr | His | Thr | Lys | Val | Met | Asn | Met | Glu | Glu | Ser | Thr | Asn | Gly | Ser | Leu |
| 385 | | | | | 390 | | | | | 395 | | | | | 400 |
| Ala | Ala | Glu | Phe | Arg | His | Leu | Gln | Leu | Lys | Glu | Gln | Lys | Asn | Ala | Gly |
| | | | | 405 | | | | | 410 | | | | | 415 | |
| Thr | Arg | Thr | Asn | Glu | Gly | Pro | Leu | Ile | Val | Thr | Glu | Glu | Leu | His | Ser |
| | | | 420 | | | | | 425 | | | | | 430 | | |
| Leu | Ser | Phe | Glu | Thr | Gln | Leu | Cys | Gln | Pro | Gly | Leu | Val | Ile | Asp | Leu |
| | | 435 | | | | | 440 | | | | | 445 | | | |
| Glu | Thr | Thr | Ser | Leu | Pro | Val | Val | Ile | Ser | Asn | Val | Ser | Gln | Leu |
| | 450 | | | | | 455 | | | | | 460 | | | | |
| Pro | Ser | Gly | Trp | Ala | Ser | Ile | Leu | Trp | Tyr | Asn | Met | Leu | Val | Ala | Glu |
| 465 | | | | | 470 | | | | | 475 | | | | | 480 |
| Pro | Arg | Asn | Leu | Ser | Phe | Phe | Leu | Thr | Pro | Pro | Cys | Ala | Arg | Trp | Ala |
| | | | | 485 | | | | | 490 | | | | | 495 | |

```
Gln Leu Ser Glu Val Leu Ser Trp Gln Phe Ser Ser Val Thr Lys Arg
            500                 505                 510

Gly Leu Asn Val Asp Gln Leu Asn Met Leu Gly Glu Lys Leu Leu Gly
            515                 520                 525

Pro Asn Ala Ser Pro Asp Gly Leu Ile Pro Trp Thr Arg Phe Cys Lys
            530                 535                 540

Glu Asn Ile Asn Asp Lys Asn Phe Pro Phe Trp Leu Trp Ile Glu Ser
545                 550                 555                 560

Ile Leu Glu Leu Ile Lys Lys His Leu Leu Pro Leu Trp Asn Asp Gly
                565                 570                 575

Cys Ile Met Gly Phe Ile Ser Lys Glu Arg Glu Arg Ala Leu Leu Lys
            580                 585                 590

Asp Gln Gln Pro Gly Thr Phe Leu Leu Arg Phe Ser Glu Ser Ser Arg
            595                 600                 605

Glu Gly Ala Ile Thr Phe Thr Trp Val Glu Arg Ser Gln Asn Gly Gly
            610                 615                 620

Glu Pro Asp Phe His Ala Val Glu Pro Tyr Thr Lys Lys Glu Leu Ser
625                 630                 635                 640

Ala Val Thr Phe Pro Asp Ile Ile Arg Asn Tyr Lys Val Met Ala Ala
                645                 650                 655

Glu Asn Ile Pro Glu Asn Pro Leu Lys Tyr Leu Tyr Pro Asn Ile Asp
            660                 665                 670

Lys Asp His Ala Phe Gly Lys Tyr Tyr Ser Arg Pro Lys Glu Ala Pro
            675                 680                 685

Glu Pro Met Glu Leu Asp Gly Pro Lys Gly Thr Gly Tyr Ile Lys Thr
            690                 695                 700

Glu Leu Ile Ser Val Ser Glu Val
705                 710
```

( 2 ) INFORMATION FOR SEQ ID NO:7:

( i ) SEQUENCE CHARACTERISTICS:
        ( A ) LENGTH: 2277 base pairs
        ( B ) TYPE: nucleic acid
        ( C ) STRANDEDNESS: both
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Mouse ( v i i ) IMMEDIATE SOURCE:
        ( B ) CLONE: Murine Stat91

( i x ) FEATURE:
        ( A ) NAME/KEY: CDS
        ( B ) LOCATION: 5..2251

( x i ) SEQUENCE DESCRIPTION: SEQ ID NO:7:

```
CAGG ATG TCA CAG TGG TTC GAG CTT CAG CAG CTG GAC TCC AAG TTC CTG     49
     Met Ser Gln Trp Phe Glu Leu Gln Gln Leu Asp Ser Lys Phe Leu
     1               5                   10                  15

GAG CAG GTC CAC CAG CTG TAC GAT GAC AGT TTC CCC ATG GAA ATC AGA     97
Glu Gln Val His Gln Leu Tyr Asp Asp Ser Phe Pro Met Glu Ile Arg
                20                  25                  30

CAG TAC CTG GCC CAG TGG CTG GAA AAG CAA GAC TGG GAG CAC GCT GCC    145
Gln Tyr Leu Ala Gln Trp Leu Glu Lys Gln Asp Trp Glu His Ala Ala
```

| | | | | | | | | | | | | | | | | |
|---|---|---|---|---|---|---|---|---|---|---|---|---|---|---|---|---|
| | | | 35 | | | | | 40 | | | | | 45 | | | |
| TAT | GAT | GTC | TCG | TTT | GCG | ACC | ATC | CGC | TTC | CAT | GAC | CTC | CTC | TCA | CAG | 193 |
| Tyr | Asp | Val | Ser | Phe | Ala | Thr | Ile | Arg | Phe | His | Asp | Leu | Leu | Ser | Gln | |
| | | 50 | | | | | 55 | | | | | 60 | | | | |
| CTG | GAC | GAC | CAG | TAC | AGC | CGC | TTT | TCT | CTG | GAG | AAT | AAT | TTC | TTG | TTG | 241 |
| Leu | Asp | Asp | Gln | Tyr | Ser | Arg | Phe | Ser | Leu | Glu | Asn | Asn | Phe | Leu | Leu | |
| | 65 | | | | | 70 | | | | | 75 | | | | | |
| CAG | CAC | AAC | ATA | CGG | AAA | AGC | AAG | CGT | AAT | CTC | CAG | GAT | AAC | TTC | CAA | 289 |
| Gln | His | Asn | Ile | Arg | Lys | Ser | Lys | Arg | Asn | Leu | Gln | Asp | Asn | Phe | Gln | |
| 80 | | | | | 85 | | | | | 90 | | | | | 95 | |
| GAA | GAT | CCC | GTA | CAG | ATG | TCC | ATG | ATC | ATC | TAC | AAC | TGT | CTG | AAG | GAA | 337 |
| Glu | Asp | Pro | Val | Gln | Met | Ser | Met | Ile | Ile | Tyr | Asn | Cys | Leu | Lys | Glu | |
| | | | | 100 | | | | | 105 | | | | | 110 | | |
| GAA | AGG | AAG | ATT | TTG | GAA | AAT | GCC | CAA | AGA | TTT | AAT | CAG | GCC | CAG | GAG | 385 |
| Glu | Arg | Lys | Ile | Leu | Glu | Asn | Ala | Gln | Arg | Phe | Asn | Gln | Ala | Gln | Glu | |
| | | | 115 | | | | | 120 | | | | | 125 | | | |
| GGA | AAT | ATT | CAG | AAC | ACT | GTG | ATG | TTA | GAT | AAA | CAG | AAG | GAG | CTG | GAC | 433 |
| Gly | Asn | Ile | Gln | Asn | Thr | Val | Met | Leu | Asp | Lys | Gln | Lys | Glu | Leu | Asp | |
| | | 130 | | | | | 135 | | | | | 140 | | | | |
| AGT | AAA | GTC | AGA | AAT | GTG | AAG | GAT | CAA | GTC | ATG | TGC | ATA | GAG | CAG | GAA | 481 |
| Ser | Lys | Val | Arg | Asn | Val | Lys | Asp | Gln | Val | Met | Cys | Ile | Glu | Gln | Glu | |
| | 145 | | | | | 150 | | | | | 155 | | | | | |
| ATC | AAG | ACC | CTA | GAA | GAA | TTA | CAA | GAT | GAA | TAT | GAC | TTT | AAA | TGC | AAA | 529 |
| Ile | Lys | Thr | Leu | Glu | Glu | Leu | Gln | Asp | Glu | Tyr | Asp | Phe | Lys | Cys | Lys | |
| 160 | | | | | 165 | | | | | 170 | | | | | 175 | |
| ACC | TCT | CAG | AAC | AGA | GAA | GGT | GAA | GCC | AAT | GGT | GTG | GCG | AAG | AGC | GAC | 577 |
| Thr | Ser | Gln | Asn | Arg | Glu | Gly | Glu | Ala | Asn | Gly | Val | Ala | Lys | Ser | Asp | |
| | | | | 180 | | | | | 185 | | | | | 190 | | |
| CAA | AAA | CAG | GAA | CAG | CTG | CTC | CTC | CAC | AAG | ATG | TTT | TTA | ATG | CTT | GAC | 625 |
| Gln | Lys | Gln | Glu | Gln | Leu | Leu | Leu | His | Lys | Met | Phe | Leu | Met | Leu | Asp | |
| | | | 195 | | | | | 200 | | | | | 205 | | | |
| AAT | AAG | AGA | AAG | GAG | ATA | ATT | CAC | AAA | ATC | AGA | GAG | TTG | CTG | AAT | TCC | 673 |
| Asn | Lys | Arg | Lys | Glu | Ile | Ile | His | Lys | Ile | Arg | Glu | Leu | Leu | Asn | Ser | |
| | | 210 | | | | | 215 | | | | | 220 | | | | |
| ATC | GAG | CTC | ACT | CAG | AAC | ACT | CTG | ATT | AAT | GAC | GAG | CTC | GTG | GAG | TGG | 721 |
| Ile | Glu | Leu | Thr | Gln | Asn | Thr | Leu | Ile | Asn | Asp | Glu | Leu | Val | Glu | Trp | |
| | 225 | | | | | 230 | | | | | 235 | | | | | |
| AAG | CGA | AGG | CAG | CAG | AGC | GCC | TGC | ATC | GGG | GGA | CCG | CCC | AAC | GCC | TGC | 769 |
| Lys | Arg | Arg | Gln | Gln | Ser | Ala | Cys | Ile | Gly | Gly | Pro | Pro | Asn | Ala | Cys | |
| 240 | | | | | 245 | | | | | 250 | | | | | 255 | |
| CTG | GAT | CAG | CTG | CAA | ACG | TGG | TTC | ACC | ATT | GTT | GCA | GAG | ACC | CTG | CAG | 817 |
| Leu | Asp | Gln | Leu | Gln | Thr | Trp | Phe | Thr | Ile | Val | Ala | Glu | Thr | Leu | Gln | |
| | | | | 260 | | | | | 265 | | | | | 270 | | |
| CAG | ATC | CGT | CAG | CAG | CTT | AAA | AAG | CTG | GAG | GAG | TTG | GAA | CAG | AAA | TTC | 865 |
| Gln | Ile | Arg | Gln | Gln | Leu | Lys | Lys | Leu | Glu | Glu | Leu | Glu | Gln | Lys | Phe | |
| | | | 275 | | | | | 280 | | | | | 285 | | | |
| ACC | TAT | GAG | CCC | GAC | CCT | ATT | ACA | AAA | AAC | AAG | CAG | GTG | TTG | TCA | GAT | 913 |
| Thr | Tyr | Glu | Pro | Asp | Pro | Ile | Thr | Lys | Asn | Lys | Gln | Val | Leu | Ser | Asp | |
| | | 290 | | | | | 295 | | | | | 300 | | | | |
| CGA | ACC | TTC | CTC | CTC | TTC | CAG | CAG | CTC | ATT | CAG | AGC | TCC | TTC | GTG | GTA | 961 |
| Arg | Thr | Phe | Leu | Leu | Phe | Gln | Gln | Leu | Ile | Gln | Ser | Ser | Phe | Val | Val | |
| | 305 | | | | | 310 | | | | | 315 | | | | | |
| GAA | CGA | CAG | CCG | TGC | ATG | CCC | ACT | CAC | CCG | CAG | AGG | CCC | CTG | GTC | TTG | 1009 |
| Glu | Arg | Gln | Pro | Cys | Met | Pro | Thr | His | Pro | Gln | Arg | Pro | Leu | Val | Leu | |
| 320 | | | | | 325 | | | | | 330 | | | | | 335 | |
| AAG | ACT | GGG | GTA | CAG | TTC | ACT | GTC | AAG | TCG | AGA | CTG | TTG | GTG | AAA | TTG | 1057 |
| Lys | Thr | Gly | Val | Gln | Phe | Thr | Val | Lys | Ser | Arg | Leu | Leu | Val | Lys | Leu | |
| | | | | 340 | | | | | 345 | | | | | 350 | | |
| CAA | GAG | TCG | AAT | CTA | TTA | ACG | AAA | GTG | AAA | TGT | CAC | TTT | GAC | AAA | GAT | 1105 |
| Gln | Glu | Ser | Asn | Leu | Leu | Thr | Lys | Val | Lys | Cys | His | Phe | Asp | Lys | Asp | |

|     |     |     |     | 355 |     |     |     |     | 360 |     |     |     |     | 365 |     |     |     |      |
|-----|-----|-----|-----|-----|-----|-----|-----|-----|-----|-----|-----|-----|-----|-----|-----|-----|-----|------|
| GTG | AAC | GAG | AAA | AAC | ACA | GTT | AAA | GGA | TTT | CGG | AAG | TTC | AAC | ATC | TTG |     |     | 1153 |
| Val | Asn | Glu | Lys | Asn | Thr | Val | Lys | Gly | Phe | Arg | Lys | Phe | Asn | Ile | Leu |     |     |      |
|     |     | 370 |     |     |     | 375 |     |     |     | 380 |     |     |     |     |     |     |     |      |
| GGT | ACG | CAC | ACA | AAA | GTG | ATG | AAC | ATG | GAA | GAA | TCC | ACC | AAC | GGA | AGT |     |     | 1201 |
| Gly | Thr | His | Thr | Lys | Val | Met | Asn | Met | Glu | Glu | Ser | Thr | Asn | Gly | Ser |     |     |      |
|     | 385 |     |     |     |     | 390 |     |     |     |     | 395 |     |     |     |     |     |     |      |
| CTG | GCA | GCT | GAG | CTC | CGA | CAC | CTG | CAA | CTG | AAG | GAA | CAG | AAA | AAC | GCT |     |     | 1249 |
| Leu | Ala | Ala | Glu | Leu | Arg | His | Leu | Gln | Leu | Lys | Glu | Gln | Lys | Asn | Ala |     |     |      |
| 400 |     |     |     |     | 405 |     |     |     |     | 410 |     |     |     |     | 415 |     |     |      |
| GGG | AAC | AGA | ACT | AAT | GAG | GGG | CCT | CTC | ATT | GTC | ACC | GAA | GAA | CTT | CAC |     |     | 1297 |
| Gly | Asn | Arg | Thr | Asn | Glu | Gly | Pro | Leu | Ile | Val | Thr | Glu | Glu | Leu | His |     |     |      |
|     |     |     |     | 420 |     |     |     | 425 |     |     |     |     |     | 430 |     |     |     |      |
| TCT | CTT | AGC | TTT | GAA | ACC | CAG | TTG | TGC | CAG | CCA | GGC | TTG | GTG | ATT | GAC |     |     | 1345 |
| Ser | Leu | Ser | Phe | Glu | Thr | Gln | Leu | Cys | Gln | Pro | Gly | Leu | Val | Ile | Asp |     |     |      |
|     |     |     | 435 |     |     |     | 440 |     |     |     |     | 445 |     |     |     |     |     |      |
| CTG | GAG | ACC | ACC | TCT | CTT | CCT | GTC | GTG | GTG | ATC | TCC | AAC | GTC | AGC | CAG |     |     | 1393 |
| Leu | Glu | Thr | Thr | Ser | Leu | Pro | Val | Val | Val | Ile | Ser | Asn | Val | Ser | Gln |     |     |      |
|     |     | 450 |     |     |     |     | 455 |     |     |     |     | 460 |     |     |     |     |     |      |
| CTC | CCC | AGT | GGC | TGG | GCG | TCT | ATC | CTG | TGG | TAC | AAC | ATG | CTG | GTG | ACA |     |     | 1441 |
| Leu | Pro | Ser | Gly | Trp | Ala | Ser | Ile | Leu | Trp | Tyr | Asn | Met | Leu | Val | Thr |     |     |      |
|     | 465 |     |     |     |     | 470 |     |     |     |     | 475 |     |     |     |     |     |     |      |
| GAG | CCC | AGG | AAT | CTC | TCC | TTC | TTC | CTG | AAC | CCC | CCG | TGC | GCG | TGG | TGG |     |     | 1489 |
| Glu | Pro | Arg | Asn | Leu | Ser | Phe | Phe | Leu | Asn | Pro | Pro | Cys | Ala | Trp | Trp |     |     |      |
| 480 |     |     |     |     | 485 |     |     |     |     | 490 |     |     |     |     | 495 |     |     |      |
| TCC | CAG | CTC | TCA | GAG | GTG | TTG | AGT | TGG | CAG | TTT | TCA | TCA | GTC | ACC | AAG |     |     | 1537 |
| Ser | Gln | Leu | Ser | Glu | Val | Leu | Ser | Trp | Gln | Phe | Ser | Ser | Val | Thr | Lys |     |     |      |
|     |     |     |     | 500 |     |     |     |     | 505 |     |     |     |     | 510 |     |     |     |      |
| AGA | GGT | CTG | AAC | GCA | GAC | CAG | CTG | AGC | ATG | CTG | GGA | GAG | AAG | CTG | CTG |     |     | 1585 |
| Arg | Gly | Leu | Asn | Ala | Asp | Gln | Leu | Ser | Met | Leu | Gly | Glu | Lys | Leu | Leu |     |     |      |
|     |     |     | 515 |     |     |     |     | 520 |     |     |     |     | 525 |     |     |     |     |      |
| GGC | CCT | AAT | GCT | GGC | CCT | GAT | GGT | CTT | ATT | CCA | TGG | ACA | AGG | TTT | TGT |     |     | 1633 |
| Gly | Pro | Asn | Ala | Gly | Pro | Asp | Gly | Leu | Ile | Pro | Trp | Thr | Arg | Phe | Cys |     |     |      |
|     |     | 530 |     |     |     | 535 |     |     |     |     | 540 |     |     |     |     |     |     |      |
| AAG | GAA | AAT | ATT | AAT | GAT | AAA | AAT | TTC | TCC | TTC | TGG | CCT | TGG | ATT | GAC |     |     | 1681 |
| Lys | Glu | Asn | Ile | Asn | Asp | Lys | Asn | Phe | Ser | Phe | Trp | Pro | Trp | Ile | Asp |     |     |      |
| 545 |     |     |     |     | 550 |     |     |     |     | 555 |     |     |     |     |     |     |     |      |
| ACC | ATC | CTA | GAG | CTC | ATT | AAG | AAC | GAC | CTG | CTG | TGC | CTC | TGG | AAT | GAT |     |     | 1729 |
| Thr | Ile | Leu | Glu | Leu | Ile | Lys | Asn | Asp | Leu | Leu | Cys | Leu | Trp | Asn | Asp |     |     |      |
| 560 |     |     |     |     | 565 |     |     |     |     | 570 |     |     |     |     | 575 |     |     |      |
| GGG | TGC | ATT | ATG | GGC | TTC | ATC | AGC | AAG | GAG | CGA | GAA | CGC | GCT | CTG | CTC |     |     | 1777 |
| Gly | Cys | Ile | Met | Gly | Phe | Ile | Ser | Lys | Glu | Arg | Glu | Arg | Ala | Leu | Leu |     |     |      |
|     |     |     |     | 580 |     |     |     |     | 585 |     |     |     |     | 590 |     |     |     |      |
| AAG | GAC | CAG | CAG | CCA | GGG | ACG | TTC | CTG | CTT | AGA | TTC | AGT | GAG | AGC | TCC |     |     | 1825 |
| Lys | Asp | Gln | Gln | Pro | Gly | Thr | Phe | Leu | Leu | Arg | Phe | Ser | Glu | Ser | Ser |     |     |      |
|     |     |     | 595 |     |     |     |     | 600 |     |     |     |     | 605 |     |     |     |     |      |
| CGG | GAA | GGG | GCC | ATC | ACA | TTC | ACA | TGG | GTG | GAA | CGG | TCC | CAG | AAC | GGA |     |     | 1873 |
| Arg | Glu | Gly | Ala | Ile | Thr | Phe | Thr | Trp | Val | Glu | Arg | Ser | Gln | Asn | Gly |     |     |      |
|     |     | 610 |     |     |     |     | 615 |     |     |     |     | 620 |     |     |     |     |     |      |
| GGT | GAA | CCT | GAC | TTC | CAT | GCC | GTG | GAG | CCC | TAC | ACG | AAA | AAA | GAA | CTT |     |     | 1921 |
| Gly | Glu | Pro | Asp | Phe | His | Ala | Val | Glu | Pro | Tyr | Thr | Lys | Lys | Glu | Leu |     |     |      |
|     | 625 |     |     |     |     | 630 |     |     |     |     | 635 |     |     |     |     |     |     |      |
| TCA | GCT | GTT | ACT | TTC | CCA | GAT | ATT | ATT | CGC | AAC | TAC | AAA | GTC | ATG | GCT |     |     | 1969 |
| Ser | Ala | Val | Thr | Phe | Pro | Asp | Ile | Ile | Arg | Asn | Tyr | Lys | Val | Met | Ala |     |     |      |
| 640 |     |     |     |     | 645 |     |     |     |     | 650 |     |     |     |     | 655 |     |     |      |
| GCC | GAG | AAC | ATA | CCA | GAG | AAT | CCC | CTG | AAG | TAT | CTG | TAC | CCC | AAT | ATT |     |     | 2017 |
| Ala | Glu | Asn | Ile | Pro | Glu | Asn | Pro | Leu | Lys | Tyr | Leu | Tyr | Pro | Asn | Ile |     |     |      |
|     |     |     |     | 660 |     |     |     | 665 |     |     |     |     |     | 670 |     |     |     |      |
| GAC | AAA | GAC | CAC | GCC | TTT | GGG | AAG | TAT | TAT | TCC | AGA | CCA | AAG | GAA | GCA |     |     | 2065 |
| Asp | Lys | Asp | His | Ala | Phe | Gly | Lys | Tyr | Tyr | Ser | Arg | Pro | Lys | Glu | Ala |     |     |      |

|   |   |   |   |   |   |   | 675 |   |   |   |   | 680 |   |   |   |   | 685 |   |   |      |
|---|---|---|---|---|---|---|-----|---|---|---|---|-----|---|---|---|---|-----|---|---|------|

```
CCA GAA CCG ATG GAG CTT GAC GAC CCT AAG CGA ACT GGA TAC ATC AAG        2113
Pro Glu Pro Met Glu Leu Asp Asp Pro Lys Arg Thr Gly Tyr Ile Lys
        690             695             700

ACT GAG TTG ATT TCT GTG TCT GAA GTC CAC CCT TCT AGA CTT CAG ACC        2161
Thr Glu Leu Ile Ser Val Ser Glu Val His Pro Ser Arg Leu Gln Thr
705             710             715

ACA GAC AAC CTG CTT CCC ATG TCT CCA GAG GAG TTT GAT GAG ATG TCC        2209
Thr Asp Asn Leu Leu Pro Met Ser Pro Glu Glu Phe Asp Glu Met Ser
720             725             730             735

CGG ATA GTG GGC CCC GAA TTT GAC AGT ATG ATG AGC ACA GTA                2251
Arg Ile Val Gly Pro Glu Phe Asp Ser Met Met Ser Thr Val
            740             745

TAAACACGAA TTTCTCTCTG GCGACA                                           2277
```

( 2 ) INFORMATION FOR SEQ ID NO:8:

( i ) SEQUENCE CHARACTERISTICS:
        ( A ) LENGTH: 749 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Ser Gln Trp Phe Glu Leu Gln Gln Leu Asp Ser Lys Phe Leu Glu
1               5                   10                  15

Gln Val His Gln Leu Tyr Asp Asp Ser Phe Pro Met Glu Ile Arg Gln
            20                  25                  30

Tyr Leu Ala Gln Trp Leu Glu Lys Gln Asp Trp Glu His Ala Ala Tyr
        35                  40                  45

Asp Val Ser Phe Ala Thr Ile Arg Phe His Asp Leu Ser Gln Leu
    50                  55                  60

Asp Asp Gln Tyr Ser Arg Phe Ser Leu Glu Asn Asn Phe Leu Leu Gln
65                  70                  75                  80

His Asn Ile Arg Lys Ser Lys Arg Asn Leu Gln Asp Asn Phe Gln Glu
                85                  90                  95

Asp Pro Val Gln Met Ser Met Ile Ile Tyr Asn Cys Leu Lys Glu Glu
            100                 105                 110

Arg Lys Ile Leu Glu Asn Ala Gln Arg Phe Asn Gln Ala Gln Glu Gly
        115                 120                 125

Asn Ile Gln Asn Thr Val Met Leu Asp Lys Gln Lys Glu Leu Asp Ser
    130                 135                 140

Lys Val Arg Asn Val Lys Asp Gln Val Met Cys Ile Glu Gln Glu Ile
145                 150                 155                 160

Lys Thr Leu Glu Glu Leu Gln Asp Glu Tyr Asp Phe Lys Cys Lys Thr
                165                 170                 175

Ser Gln Asn Arg Glu Gly Glu Ala Asn Gly Val Ala Lys Ser Asp Gln
            180                 185                 190

Lys Gln Glu Gln Leu Leu Leu His Lys Met Phe Leu Met Leu Asp Asn
        195                 200                 205

Lys Arg Lys Glu Ile Ile His Lys Ile Arg Glu Leu Leu Asn Ser Ile
    210                 215                 220

Glu Leu Thr Gln Asn Thr Leu Ile Asn Asp Glu Leu Val Glu Trp Lys
225                 230                 235                 240

Arg Arg Gln Gln Ser Ala Cys Ile Gly Gly Pro Pro Asn Ala Cys Leu
                245                 250                 255
```

| | | | | | | | | | | | | | | |
|---|---|---|---|---|---|---|---|---|---|---|---|---|---|---|
| Asp | Gln | Leu | Gln 260 | Thr | Trp | Phe | Thr | Ile 265 | Val | Ala | Glu | Thr | Leu 270 | Gln | Gln |
| Ile | Arg | Gln 275 | Gln | Leu | Lys | Lys | Leu 280 | Glu | Leu | Glu | Gln 285 | Lys | Phe | Thr |
| Tyr | Glu 290 | Pro | Asp | Pro | Ile | Thr 295 | Lys | Asn | Lys | Gln 300 | Val | Leu | Ser | Asp | Arg |
| Thr 305 | Phe | Leu | Leu | Phe | Gln 310 | Gln | Leu | Ile | Gln | Ser 315 | Ser | Phe | Val | Val | Glu 320 |
| Arg | Gln | Pro | Cys | Met 325 | Pro | Thr | His | Pro | Gln 330 | Arg | Pro | Leu | Val | Leu 335 | Lys |
| Thr | Gly | Val | Gln 340 | Phe | Thr | Val | Lys | Ser 345 | Arg | Leu | Leu | Val | Lys 350 | Leu | Gln |
| Glu | Ser | Asn 355 | Leu | Leu | Thr | Lys | Val 360 | Lys | Cys | His | Phe | Asp 365 | Lys | Asp | Val |
| Asn | Glu 370 | Lys | Asn | Thr | Val | Lys 375 | Gly | Phe | Arg | Lys | Phe 380 | Asn | Ile | Leu | Gly |
| Thr 385 | His | Thr | Lys | Val | Met 390 | Asn | Met | Glu | Glu | Ser 395 | Thr | Asn | Gly | Ser | Leu 400 |
| Ala | Ala | Glu | Leu | Arg 405 | His | Leu | Gln | Leu | Lys 410 | Glu | Gln | Lys | Asn | Ala 415 | Gly |
| Asn | Arg | Thr | Asn 420 | Glu | Gly | Pro | Leu | Ile 425 | Val | Thr | Glu | Glu | Leu 430 | His | Ser |
| Leu | Ser | Phe 435 | Glu | Thr | Gln | Leu | Cys 440 | Gln | Pro | Gly | Leu | Val 445 | Ile | Asp | Leu |
| Glu | Thr 450 | Thr | Ser | Leu | Pro | Val 455 | Val | Val | Ile | Ser | Asn 460 | Val | Ser | Gln | Leu |
| Pro 465 | Ser | Gly | Trp | Ala | Ser 470 | Ile | Leu | Trp | Tyr | Asn 475 | Met | Leu | Val | Thr | Glu 480 |
| Pro | Arg | Asn | Leu | Ser 485 | Phe | Phe | Leu | Asn | Pro 490 | Pro | Cys | Ala | Trp | Trp 495 | Ser |
| Gln | Leu | Ser | Glu 500 | Val | Leu | Ser | Trp | Gln 505 | Phe | Ser | Ser | Val | Thr 510 | Lys | Arg |
| Gly | Leu | Asn | Ala 515 | Asp | Gln | Leu | Ser 520 | Met | Leu | Gly | Glu | Lys 525 | Leu | Leu | Gly |
| Pro | Asn 530 | Ala | Gly | Pro | Asp | Gly 535 | Leu | Ile | Pro | Trp | Thr 540 | Arg | Phe | Cys | Lys |
| Glu 545 | Asn | Ile | Asn | Asp | Lys 550 | Asn | Phe | Ser | Phe | Trp 555 | Pro | Trp | Ile | Asp | Thr 560 |
| Ile | Leu | Glu | Leu | Ile 565 | Lys | Asn | Asp | Leu | Leu 570 | Cys | Leu | Trp | Asn | Asp 575 | Gly |
| Cys | Ile | Met | Gly 580 | Phe | Ile | Ser | Lys | Glu 585 | Arg | Glu | Arg | Ala | Leu 590 | Leu | Lys |
| Asp | Gln | Gln 595 | Pro | Gly | Thr | Phe | Leu 600 | Leu | Arg | Phe | Ser | Glu 605 | Ser | Ser | Arg |
| Glu | Gly 610 | Ala | Ile | Thr | Phe | Thr 615 | Trp | Val | Glu | Arg | Ser 620 | Gln | Asn | Gly | Gly |
| Glu 625 | Pro | Asp | Phe | His | Ala 630 | Val | Glu | Pro | Tyr | Thr 635 | Lys | Lys | Glu | Leu | Ser 640 |
| Ala | Val | Thr | Phe | Pro 645 | Asp | Ile | Ile | Arg | Asn 650 | Tyr | Lys | Val | Met | Ala 655 | Ala |
| Glu | Asn | Ile | Pro 660 | Glu | Asn | Pro | Leu | Lys 665 | Tyr | Leu | Tyr | Pro | Asn 670 | Ile | Asp |
| Lys | Asp | His 675 | Ala | Phe | Gly | Lys | Tyr 680 | Tyr | Ser | Arg | Pro | Lys 685 | Glu | Ala | Pro |

```
         Glu   Pro   Met   Glu   Leu   Asp   Asp   Pro   Lys   Arg   Thr   Gly   Tyr   Ile   Lys   Thr
               690                           695                           700

Glu   Leu   Ile   Ser   Val   Ser   Glu   Val   His   Pro   Ser   Arg   Leu   Gln   Thr   Thr
         705                           710                           715                           720

Asp   Asn   Leu   Leu   Pro   Met   Ser   Pro   Glu   Glu   Phe   Asp   Glu   Met   Ser   Arg
                             725                           730                           735

Ile   Val   Gly   Pro   Glu   Phe   Asp   Ser   Met   Met   Ser   Thr   Val
                           740                           745
```

(2) INFORMATION FOR SEQ ID NO:9:

(i) SEQUENCE CHARACTERISTICS:
        (A) LENGTH: 2375 base pairs
        (B) TYPE: nucleic acid
        (C) STRANDEDNESS: both
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Mouse (vii) IMMEDIATE SOURCE:
        (A) LIBRARY: splenic/thymic
        (B) CLONE: Murine 13sf1

(ix) FEATURE:
        (A) NAME/KEY: CDS
        (B) LOCATION: 34..2277

(xi) SEQUENCE DESCRIPTION: SEQ ID NO:9:

```
TGCCACTACC  TGGACGGAGA  GAGAGAGAGC  AGC  ATG  TCT  CAG  TGG  AAT  CAA  GTC        54
                                        Met  Ser  Gln  Trp  Asn  Gln  Val
                                         1                    5

CAA  CAA  TTA  GAA  ATC  AAG  TTT  TTG  GAG  CAA  GTA  GAT  CAG  TTC  TAT  GAT   102
Gln  Gln  Leu  Glu  Ile  Lys  Phe  Leu  Glu  Gln  Val  Asp  Gln  Phe  Tyr  Asp
               10                       15                       20

GAC  AAC  TTT  CCT  ATG  GAA  ATC  CGG  CAT  CTG  CTA  GCT  CAG  TGG  ATT  GAG   150
Asp  Asn  Phe  Pro  Met  Glu  Ile  Arg  His  Leu  Leu  Ala  Gln  Trp  Ile  Glu
          25                       30                       35

ACT  CAA  GAC  TGG  GAA  GTA  GCT  TCT  AAC  AAT  GAA  ACT  ATG  GCA  ACA  ATT   198
Thr  Gln  Asp  Trp  Glu  Val  Ala  Ser  Asn  Asn  Glu  Thr  Met  Ala  Thr  Ile
 40                       45                       50                       55

CTG  CTT  CAA  AAC  TTA  CTA  ATA  CAA  TTG  GAT  GAA  CAG  TTG  GGG  CGG  GTT   246
Leu  Leu  Gln  Asn  Leu  Leu  Ile  Gln  Leu  Asp  Glu  Gln  Leu  Gly  Arg  Val
                    60                       65                       70

TCC  AAA  GAA  AAA  AAT  CTG  CTA  TTG  ATT  CAC  AAT  CTA  AAG  AGA  ATT  AGA   294
Ser  Lys  Glu  Lys  Asn  Leu  Leu  Leu  Ile  His  Asn  Leu  Lys  Arg  Ile  Arg
               75                       80                       85

AAA  GTT  CTT  CAG  GGC  AAG  TTT  CAT  GGA  AAT  CCA  ATG  CAT  GTA  GCT  GTG   342
Lys  Val  Leu  Gln  Gly  Lys  Phe  His  Gly  Asn  Pro  Met  His  Val  Ala  Val
          90                       95                       100

GTA  ATT  TCA  AAT  TGC  TTA  AGG  GAA  GAG  AGG  AGA  ATA  TTG  GCT  GCA  GCC   390
Val  Ile  Ser  Asn  Cys  Leu  Arg  Glu  Glu  Arg  Arg  Ile  Leu  Ala  Ala  Ala
     105                      110                      115

AAC  ATG  CCT  ATC  CAG  GGA  CCT  CTG  GAG  AAA  TCC  TTA  CAG  AGT  TCT  TCA   438
Asn  Met  Pro  Ile  Gln  Gly  Pro  Leu  Glu  Lys  Ser  Leu  Gln  Ser  Ser  Ser
120                      125                      130                      135

GTT  TCT  GAA  AGA  CAA  AGG  AAT  GTG  GAA  CAC  AAA  GTG  TCT  GCC  ATT  AAA   486
Val  Ser  Glu  Arg  Gln  Arg  Asn  Val  Glu  His  Lys  Val  Ser  Ala  Ile  Lys
               140                      145                      150
```

| | | | | | | | | | | | | | | | | |
|---|---|---|---|---|---|---|---|---|---|---|---|---|---|---|---|---|
|AAC|AGT|GTG|CAG|ATG|ACA|GAA|CAA|GAT|ACC|AAA|TAC|TTA|GAA|GAC|CTG|534|
|Asn|Ser|Val|Gln|Met|Thr|Glu|Gln|Asp|Thr|Lys|Tyr|Leu|Glu|Asp|Leu||
| | |155| | | |160| | | |165| | | | | | |
|CAA|GAT|GAG|TTT|GAC|TAC|AGG|TAT|AAA|ACA|ATT|CAG|ACA|ATG|GAT|CAG|582|
|Gln|Asp|Glu|Phe|Asp|Tyr|Arg|Tyr|Lys|Thr|Ile|Gln|Thr|Met|Asp|Gln||
| | |170| | | |175| | | |180| | | | | | |
|GGT|GAC|AAA|AAC|AGT|ATC|CTG|GTG|AAC|CAG|GAA|GTT|TTG|ACA|CTG|CTG|630|
|Gly|Asp|Lys|Asn|Ser|Ile|Leu|Val|Asn|Gln|Glu|Val|Leu|Thr|Leu|Leu||
| | |185| | | |190| | | |195| | | | | | |
|CAA|GAA|ATG|CTT|AAT|AGT|CTG|GAC|TTC|AAG|AGA|AAG|GAA|GCA|CTC|AGT|678|
|Gln|Glu|Met|Leu|Asn|Ser|Leu|Asp|Phe|Lys|Arg|Lys|Glu|Ala|Leu|Ser||
|200| | | |205| | | |210| | | |215| | | | |
|AAG|ATG|ACG|CAG|ATA|GTG|AAC|GAG|ACA|GAC|CTG|CTC|ATG|AAC|AGC|ATG|726|
|Lys|Met|Thr|Gln|Ile|Val|Asn|Glu|Thr|Asp|Leu|Leu|Met|Asn|Ser|Met||
| | | |220| | | |225| | | | |230| | | | |
|CTT|CTA|GAA|GAG|CTG|CAG|GAC|TGG|AAA|AAG|CGG|CAC|AGG|ATT|GCC|TGC|774|
|Leu|Leu|Glu|Glu|Leu|Gln|Asp|Trp|Lys|Lys|Arg|His|Arg|Ile|Ala|Cys||
| | |235| | | |240| | | |245| | | | | | |
|ATT|GGT|GGC|CCG|CTC|CAC|AAT|GGG|CTG|GAC|CAG|CTT|CAG|AAC|TGC|TTT|822|
|Ile|Gly|Gly|Pro|Leu|His|Asn|Gly|Leu|Asp|Gln|Leu|Gln|Asn|Cys|Phe||
| | |250| | | |255| | | |260| | | | | | |
|ACC|CTA|CTG|GCA|GAG|AGT|CTT|TTC|CAA|CTC|AGA|CAG|CAA|CTG|GAG|AAA|870|
|Thr|Leu|Leu|Ala|Glu|Ser|Leu|Phe|Gln|Leu|Arg|Gln|Gln|Leu|Glu|Lys||
|265| | | |270| | | |275| | | | | | | | |
|CTA|CAG|GAG|CAA|TCT|ACT|AAA|ATG|ACC|TAT|GAA|GGG|GAT|CCC|ATC|CCT|918|
|Leu|Gln|Glu|Gln|Ser|Thr|Lys|Met|Thr|Tyr|Glu|Gly|Asp|Pro|Ile|Pro||
|280| | | |285| | | |290| | | | | | | |295|
|GCT|CAA|AGA|GCA|CAC|CTC|CTG|GAA|AGA|GCT|ACC|TTC|CTG|ATC|TAC|AAC|966|
|Ala|Gln|Arg|Ala|His|Leu|Leu|Glu|Arg|Ala|Thr|Phe|Leu|Ile|Tyr|Asn||
| | | |300| | | |305| | | | |310| | | | |
|CTT|TTC|AAG|AAC|TCA|TTT|GTG|GTC|GAG|CGA|CAC|GCA|TGC|ATG|CCA|ACG|1014|
|Leu|Phe|Lys|Asn|Ser|Phe|Val|Val|Glu|Arg|His|Ala|Cys|Met|Pro|Thr||
| | | |315| | | |320| | | | |325| | | | |
|CAC|CCT|CAG|AGG|CCG|ATG|GTA|CTT|AAA|ACC|CTC|ATT|CAG|TTC|ACT|GTA|1062|
|His|Pro|Gln|Arg|Pro|Met|Val|Leu|Lys|Thr|Leu|Ile|Gln|Phe|Thr|Val||
| | |330| | | |335| | | | |340| | | | | |
|AAA|CTG|AGA|TTA|CTA|ATA|AAA|TTG|CCG|GAA|CTA|AAC|TAT|CAG|GTG|AAA|1110|
|Lys|Leu|Arg|Leu|Leu|Ile|Lys|Leu|Pro|Glu|Leu|Asn|Tyr|Gln|Val|Lys||
|345| | | |350| | | |355| | | | | | | | |
|GTA|AAG|GCG|TCC|ATT|GAC|AAG|AAT|GTT|TCA|ACT|CTA|AGC|AAT|AGA|AGA|1158|
|Val|Lys|Ala|Ser|Ile|Asp|Lys|Asn|Val|Ser|Thr|Leu|Ser|Asn|Arg|Arg||
|360| | | |365| | | |370| | | | | | | |375|
|TTT|GTG|CTT|TGT|GGA|ACT|CAC|GTC|AAA|GCT|ATG|TCC|AGT|GAG|GAA|TCT|1206|
|Phe|Val|Leu|Cys|Gly|Thr|His|Val|Lys|Ala|Met|Ser|Ser|Glu|Glu|Ser||
| | | |380| | | |385| | | | |390| | | | |
|TCC|AAT|GGG|AGC|CTC|TCA|GTG|GAG|TTA|GAC|ATT|GCA|ACC|CAA|GGA|GAT|1254|
|Ser|Asn|Gly|Ser|Leu|Ser|Val|Glu|Leu|Asp|Ile|Ala|Thr|Gln|Gly|Asp||
| | | |395| | | |400| | | |405| | | | | |
|GAA|GTG|CAG|TAC|TGG|AGT|AAA|GGA|AAC|GAG|GGC|TGC|CAC|ATG|GTG|ACA|1302|
|Glu|Val|Gln|Tyr|Trp|Ser|Lys|Gly|Asn|Glu|Gly|Cys|His|Met|Val|Thr||
| | |410| | | |415| | | |420| | | | | | |
|GAG|GAG|TTG|CAT|TCC|ATA|ACC|TTT|GAG|ACC|CAG|ATC|TGC|CTC|TAT|GGC|1350|
|Glu|Glu|Leu|His|Ser|Ile|Thr|Phe|Glu|Thr|Gln|Ile|Cys|Leu|Tyr|Gly||
| |425| | | |430| | | |435| | | | | | | |
|CTC|ACC|ATT|AAC|CTA|GAG|ACC|AGC|TCA|TTA|CCT|GTC|GTG|ATG|ATT|TCT|1398|
|Leu|Thr|Ile|Asn|Leu|Glu|Thr|Ser|Ser|Leu|Pro|Val|Val|Met|Ile|Ser||
|440| | | |445| | | |450| | | | | | | |455|
|AAT|GTC|AGC|CAA|CTA|CCT|AAT|GCA|TGG|GCA|TCC|ATC|ATT|TGG|TAC|AAT|1446|
|Asn|Val|Ser|Gln|Leu|Pro|Asn|Ala|Trp|Ala|Ser|Ile|Ile|Trp|Tyr|Asn||
| | | |460| | | |465| | | |470| | | | | |

| | | | | | | | | | | | | | | | | |
|---|---|---|---|---|---|---|---|---|---|---|---|---|---|---|---|---|
| GTA | TCA | ACT | AAC | GAC | TCC | CAG | AAC | TTG | GTT | TTC | TTT | AAT | AAC | CCT | CCA | 1494 |
| Val | Ser | Thr | Asn | Asp | Ser | Gln | Asn | Leu | Val | Phe | Phe | Asn | Asn | Pro | Pro | |
| | | | 475 | | | | | 480 | | | | | 485 | | | |
| TCT | GTC | ACT | TTG | GGC | CAA | CTC | CTG | GAA | GTG | ATG | AGC | TGG | CAA | TTT | TCA | 1542 |
| Ser | Val | Thr | Leu | Gly | Gln | Leu | Leu | Glu | Val | Met | Ser | Trp | Gln | Phe | Ser | |
| | | 490 | | | | | 495 | | | | | 500 | | | | |
| TCC | TAT | GTC | GGT | CGT | GGC | CTT | AAT | TCA | GAG | CAG | CTC | AAC | ATG | CTG | GCA | 1590 |
| Ser | Tyr | Val | Gly | Arg | Gly | Leu | Asn | Ser | Glu | Gln | Leu | Asn | Met | Leu | Ala | |
| | 505 | | | | | 510 | | | | | 515 | | | | | |
| GAG | AAG | CTC | ACA | GTT | CAG | TCT | AAC | TAC | AAT | GAT | GGT | CAC | CTC | ACC | TGG | 1638 |
| Glu | Lys | Leu | Thr | Val | Gln | Ser | Asn | Tyr | Asn | Asp | Gly | His | Leu | Thr | Trp | |
| 520 | | | | | 525 | | | | | 530 | | | | | 535 | |
| GCC | AAG | TTC | TGC | AAG | GAA | CAT | TTG | CCT | GGC | AAA | ACA | TTT | ACC | TTC | TGG | 1686 |
| Ala | Lys | Phe | Cys | Lys | Glu | His | Leu | Pro | Gly | Lys | Thr | Phe | Thr | Phe | Trp | |
| | | | 540 | | | | | 545 | | | | | 550 | | | |
| ACT | TGG | CTT | GAA | GCA | ATA | TTG | GAC | CTA | ATT | AAA | AAA | CAT | ATT | CTT | CCC | 1734 |
| Thr | Trp | Leu | Glu | Ala | Ile | Leu | Asp | Leu | Ile | Lys | Lys | His | Ile | Leu | Pro | |
| | | | | 555 | | | | | 560 | | | | | 565 | | |
| CTC | TGG | ATT | GAT | GGG | TAC | ATC | ATG | GGA | TTT | GTT | AGT | AAA | GAG | AAG | GAA | 1782 |
| Leu | Trp | Ile | Asp | Gly | Tyr | Ile | Met | Gly | Phe | Val | Ser | Lys | Glu | Lys | Glu | |
| | | 570 | | | | | 575 | | | | | 580 | | | | |
| CGG | CTT | CTG | CTC | AAA | GAT | AAA | ATG | CCT | GGG | ACA | TTT | TTG | TTA | AGA | TTC | 1830 |
| Arg | Leu | Leu | Leu | Lys | Asp | Lys | Met | Pro | Gly | Thr | Phe | Leu | Leu | Arg | Phe | |
| | 585 | | | | | 590 | | | | | 595 | | | | | |
| AGT | GAG | AGC | CAT | CTT | GGA | GGG | ATA | ACC | TTC | ACC | TGG | GTG | GAC | CAA | TCT | 1878 |
| Ser | Glu | Ser | His | Leu | Gly | Gly | Ile | Thr | Phe | Thr | Trp | Val | Asp | Gln | Ser | |
| 600 | | | | | 605 | | | | | 610 | | | | | 615 | |
| GAA | AAT | GGA | GAA | GTG | AGA | TTC | CAC | TCT | GTA | GAA | CCC | TAC | AAC | AAA | GGG | 1926 |
| Glu | Asn | Gly | Glu | Val | Arg | Phe | His | Ser | Val | Glu | Pro | Tyr | Asn | Lys | Gly | |
| | | | | 620 | | | | | 625 | | | | | 630 | | |
| AGA | CTG | TCG | GCT | CTG | GCC | TTC | GCT | GAC | ATC | CTG | CGA | GAC | TAC | AAG | GTT | 1974 |
| Arg | Leu | Ser | Ala | Leu | Ala | Phe | Ala | Asp | Ile | Leu | Arg | Asp | Tyr | Lys | Val | |
| | | | 635 | | | | | 640 | | | | | 645 | | | |
| ATC | ATG | GCT | GAA | AAC | ATC | CCT | GAA | AAC | CCT | CTG | AAG | TAC | CTC | TAC | CCT | 2022 |
| Ile | Met | Ala | Glu | Asn | Ile | Pro | Glu | Asn | Pro | Leu | Lys | Tyr | Leu | Tyr | Pro | |
| | | 650 | | | | | 655 | | | | | 660 | | | | |
| GAC | ATT | CCC | AAA | GAC | AAA | GCC | TTT | GGC | AAA | CAC | TAC | AGC | TCC | CAG | CCG | 2070 |
| Asp | Ile | Pro | Lys | Asp | Lys | Ala | Phe | Gly | Lys | His | Tyr | Ser | Ser | Gln | Pro | |
| | 665 | | | | | 670 | | | | | 675 | | | | | |
| TGC | GAA | GTC | TCA | AGA | CCA | ACC | GAA | CGG | GGA | GAC | AAG | GGT | TAC | GTC | CCC | 2118 |
| Cys | Glu | Val | Ser | Arg | Pro | Thr | Glu | Arg | Gly | Asp | Lys | Gly | Tyr | Val | Pro | |
| 680 | | | | | 685 | | | | | 690 | | | | | 695 | |
| TCT | GTT | TTT | ATC | CCC | ATT | TCA | ACA | ATC | CGA | AGC | GAT | TCC | ACG | GAG | CCA | 2166 |
| Ser | Val | Phe | Ile | Pro | Ile | Ser | Thr | Ile | Arg | Ser | Asp | Ser | Thr | Glu | Pro | |
| | | | | 700 | | | | | 705 | | | | | 710 | | |
| CAA | TCT | CCT | TCA | GAC | CTT | CTC | CCC | ATG | TCT | CCA | AGT | GCA | TAT | GCT | GTG | 2214 |
| Gln | Ser | Pro | Ser | Asp | Leu | Leu | Pro | Met | Ser | Pro | Ser | Ala | Tyr | Ala | Val | |
| | | | 715 | | | | | 720 | | | | | 725 | | | |
| CTG | AGA | GAA | AAC | CTG | AGC | CCA | ACG | ACA | ATT | GAA | ACT | GCA | ATG | AAT | TCC | 2262 |
| Leu | Arg | Glu | Asn | Leu | Ser | Pro | Thr | Thr | Ile | Glu | Thr | Ala | Met | Asn | Ser | |
| | | 730 | | | | | 735 | | | | | 740 | | | | |
| CCA | TAT | TCT | GCT | GAA | TGACGGTGCA | AACGGACACT | TTAAGAAGG | AAGCAGATGA | | | | | | | | 2317 |
| Pro | Tyr | Ser | Ala | Glu | | | | | | | | | | | | |
| | 745 | | | | | | | | | | | | | | | |

AACTGGAGAG TGTTCTTTAC CATAGATCAC AATTTATTTC TTCGGCTTTG TAAATACC       2375

( 2 ) INFORMATION FOR SEQ ID NO:10:

( i ) SEQUENCE CHARACTERISTICS:
( A ) LENGTH: 748 amino acids (B) TYPE: amino acid
(D) TOPOLOGY: linear (ii) MOLECULE TYPE: protein (xi) SEQUENCE DESCRIPTION: SEQ ID NO:10:

```
Met Ser Gln Trp Asn Gln Val Gln Gln Leu Glu Ile Lys Phe Leu Glu
 1               5                  10                  15

Gln Val Asp Gln Phe Tyr Asp Asp Asn Phe Pro Met Glu Ile Arg His
            20                  25                  30

Leu Leu Ala Gln Trp Ile Glu Thr Gln Asp Trp Glu Val Ala Ser Asn
        35                  40                  45

Asn Glu Thr Met Ala Thr Ile Leu Leu Gln Asn Leu Leu Ile Gln Leu
    50                  55                  60

Asp Glu Gln Leu Gly Arg Val Ser Lys Glu Lys Asn Leu Leu Leu Ile
65                  70                  75                  80

His Asn Leu Lys Arg Ile Arg Lys Val Leu Gln Gly Lys Phe His Gly
                85                  90                  95

Asn Pro Met His Val Ala Val Val Ile Ser Asn Cys Leu Arg Glu Glu
           100                 105                 110

Arg Arg Ile Leu Ala Ala Ala Asn Met Pro Ile Gln Gly Pro Leu Glu
           115                 120                 125

Lys Ser Leu Gln Ser Ser Ser Val Ser Glu Arg Gln Arg Asn Val Glu
       130                 135                 140

His Lys Val Ser Ala Ile Lys Asn Ser Val Gln Met Thr Glu Gln Asp
145                 150                 155                 160

Thr Lys Tyr Leu Glu Asp Leu Gln Asp Glu Phe Asp Tyr Arg Tyr Lys
                165                 170                 175

Thr Ile Gln Thr Met Asp Gln Gly Asp Lys Asn Ser Ile Leu Val Asn
           180                 185                 190

Gln Glu Val Leu Thr Leu Leu Gln Glu Met Leu Asn Ser Leu Asp Phe
       195                 200                 205

Lys Arg Lys Glu Ala Leu Ser Lys Met Thr Gln Ile Val Asn Glu Thr
   210                 215                 220

Asp Leu Leu Met Asn Ser Met Leu Leu Glu Glu Leu Gln Asp Trp Lys
225                 230                 235                 240

Lys Arg His Arg Ile Ala Cys Ile Gly Gly Pro Leu His Asn Gly Leu
                245                 250                 255

Asp Gln Leu Gln Asn Cys Phe Thr Leu Leu Ala Glu Ser Leu Phe Gln
           260                 265                 270

Leu Arg Gln Gln Leu Glu Lys Leu Gln Glu Gln Ser Thr Lys Met Thr
       275                 280                 285

Tyr Glu Gly Asp Pro Ile Pro Ala Gln Arg Ala His Leu Leu Glu Arg
   290                 295                 300

Ala Thr Phe Leu Ile Tyr Asn Leu Phe Lys Asn Ser Phe Val Val Glu
305                 310                 315                 320

Arg His Ala Cys Met Pro Thr His Pro Gln Arg Pro Met Val Leu Lys
                325                 330                 335

Thr Leu Ile Gln Phe Thr Val Lys Leu Arg Leu Leu Ile Lys Leu Pro
           340                 345                 350

Glu Leu Asn Tyr Gln Val Lys Val Lys Ala Ser Ile Asp Lys Asn Val
       355                 360                 365

Ser Thr Leu Ser Asn Arg Arg Phe Val Leu Cys Gly Thr His Val Lys
   370                 375                 380

Ala Met Ser Ser Glu Glu Ser Ser Asn Gly Ser Leu Ser Val Glu Leu
```

| | | 385 | | | | 390 | | | | 395 | | | | 400 |
|---|---|---|---|---|---|---|---|---|---|---|---|---|---|---|
| Asp | Ile | Ala | Thr | Gln | Gly | Asp | Glu | Val | Gln | Tyr | Trp | Ser | Lys | Gly | Asn |
| | | | | 405 | | | | 410 | | | | | 415 | |
| Glu | Gly | Cys | His | Met | Val | Thr | Glu | Glu | Leu | His | Ser | Ile | Thr | Phe | Glu |
| | | | 420 | | | | | 425 | | | | 430 | | |
| Thr | Gln | Ile | Cys | Leu | Tyr | Gly | Leu | Thr | Ile | Asn | Leu | Glu | Thr | Ser | Ser |
| | | 435 | | | | 440 | | | | | 445 | | | |
| Leu | Pro | Val | Val | Met | Ile | Ser | Asn | Val | Ser | Gln | Leu | Pro | Asn | Ala | Trp |
| | 450 | | | | 455 | | | | | 460 | | | | |
| Ala | Ser | Ile | Ile | Trp | Tyr | Asn | Val | Ser | Thr | Asn | Asp | Ser | Gln | Asn | Leu |
| 465 | | | | | 470 | | | | 475 | | | | | 480 | |
| Val | Phe | Phe | Asn | Asn | Pro | Pro | Ser | Val | Thr | Leu | Gly | Gln | Leu | Leu | Glu |
| | | | | 485 | | | | | 490 | | | | 495 | | |
| Val | Met | Ser | Trp | Gln | Phe | Ser | Ser | Tyr | Val | Gly | Arg | Gly | Leu | Asn | Ser |
| | | | 500 | | | | | 505 | | | | 510 | | | |
| Glu | Gln | Leu | Asn | Met | Leu | Ala | Glu | Lys | Leu | Thr | Val | Gln | Ser | Asn | Tyr |
| | | | 515 | | | | 520 | | | | | 525 | | | |
| Asn | Asp | Gly | His | Leu | Thr | Trp | Ala | Lys | Phe | Cys | Lys | Glu | His | Leu | Pro |
| | 530 | | | | | 535 | | | | | 540 | | | | |
| Gly | Lys | Thr | Phe | Thr | Phe | Trp | Thr | Trp | Leu | Glu | Ala | Ile | Leu | Asp | Leu |
| 545 | | | | | 550 | | | | 555 | | | | | 560 | |
| Ile | Lys | Lys | His | Ile | Leu | Pro | Leu | Trp | Ile | Asp | Gly | Tyr | Ile | Met | Gly |
| | | | | 565 | | | | | 570 | | | | 575 | | |
| Phe | Val | Ser | Lys | Glu | Lys | Glu | Arg | Leu | Leu | Leu | Lys | Asp | Lys | Met | Pro |
| | | | 580 | | | | | 585 | | | | | 590 | | |
| Gly | Thr | Phe | Leu | Leu | Arg | Phe | Ser | Glu | Ser | His | Leu | Gly | Gly | Ile | Thr |
| | | 595 | | | | | 600 | | | | | 605 | | | |
| Phe | Thr | Trp | Val | Asp | Gln | Ser | Glu | Asn | Gly | Glu | Val | Arg | Phe | His | Ser |
| | 610 | | | | | 615 | | | | | 620 | | | | |
| Val | Glu | Pro | Tyr | Asn | Lys | Gly | Arg | Leu | Ser | Ala | Leu | Ala | Phe | Ala | Asp |
| 625 | | | | | 630 | | | | 635 | | | | | 640 | |
| Ile | Leu | Arg | Asp | Tyr | Lys | Val | Ile | Met | Ala | Glu | Asn | Ile | Pro | Glu | Asn |
| | | | | 645 | | | | 650 | | | | | 655 | | |
| Pro | Leu | Lys | Tyr | Leu | Tyr | Pro | Asp | Ile | Pro | Lys | Asp | Lys | Ala | Phe | Gly |
| | | | 660 | | | | | 665 | | | | 670 | | | |
| Lys | His | Tyr | Ser | Ser | Gln | Pro | Cys | Glu | Val | Ser | Arg | Pro | Thr | Glu | Arg |
| | | 675 | | | | | 680 | | | | | 685 | | | |
| Gly | Asp | Lys | Gly | Tyr | Val | Pro | Ser | Val | Phe | Ile | Pro | Ile | Ser | Thr | Ile |
| | | 690 | | | | 695 | | | | | 700 | | | | |
| Arg | Ser | Asp | Ser | Thr | Glu | Pro | Gln | Ser | Pro | Ser | Asp | Leu | Leu | Pro | Met |
| 705 | | | | | 710 | | | | 715 | | | | | 720 | |
| Ser | Pro | Ser | Ala | Tyr | Ala | Val | Leu | Arg | Glu | Asn | Leu | Ser | Pro | Thr | Thr |
| | | | | 725 | | | | 730 | | | | | 735 | | |
| Ile | Glu | Thr | Ala | Met | Asn | Ser | Pro | Tyr | Ser | Ala | Glu | | | | |
| | | | 740 | | | | | 745 | | | | | | | |

( 2 ) INFORMATION FOR SEQ ID NO:11:

( i ) SEQUENCE CHARACTERISTICS:
        ( A ) LENGTH: 2869 base pairs
        ( B ) TYPE: nucleic acid
        ( C ) STRANDEDNESS: both
        ( D ) TOPOLOGY: unknown ( i i ) MOLECULE TYPE: cDNA ( i i i ) HYPOTHETICAL: NO ( i v ) ANTI-SENSE: NO ( v i ) ORIGINAL SOURCE:
 ( A ) ORGANISM: Mouse ( v i i ) IMMEDIATE SOURCE:
 ( A ) LIBRARY: splenic/thymic
 ( B ) CLONE: Murine 19sf6

( i x ) FEATURE:
 ( A ) NAME/KEY: CDS
 ( B ) LOCATION: 69..2378

( x i ) SEQUENCE DESCRIPTION: SEQ ID NO:11:

```
GCCGCGACCA GCCAGGCCGG CCAGTCGGGC TCAGCCCGGA GACAGTCGAG ACCCCTGACT         60
```

| GCAGCAGG | ATG<br>Met<br>1 | GCT<br>Ala | CAG<br>Gln | TGG<br>Trp | AAC<br>Asn<br>5 | CAG<br>Gln | CTG<br>Leu | CAG<br>Gln | CAG<br>Gln | CTG<br>Leu<br>10 | GAC<br>Asp | ACA<br>Thr | CGC<br>Arg | TAC<br>Tyr | 110 |
| --- | --- | --- | --- | --- | --- | --- | --- | --- | --- | --- | --- | --- | --- | --- | --- |
| CTG<br>Leu<br>15 | AAG<br>Lys | CAG<br>Gln | CTG<br>Leu | CAC<br>His | CAG<br>Gln<br>20 | CTG<br>Leu | TAC<br>Tyr | AGC<br>Ser | GAC<br>Asp | ACG<br>Thr<br>25 | TTC<br>Phe | CCC<br>Pro | ATG<br>Met | GAG<br>Glu | CTG<br>Leu<br>30 | 158 |
| CGG<br>Arg | CAG<br>Gln | TTC<br>Phe | CTG<br>Leu | GCA<br>Ala<br>35 | CCT<br>Pro | TGG<br>Trp | ATT<br>Ile | GAG<br>Glu | AGT<br>Ser<br>40 | CAA<br>Gln | GAC<br>Asp | TGG<br>Trp | GCA<br>Ala | TAT<br>Tyr<br>45 | GCA<br>Ala | 206 |
| GCC<br>Ala | AGC<br>Ser | AAA<br>Lys<br>50 | GAG<br>Glu | TCA<br>Ser | CAT<br>His | GCC<br>Ala | ACG<br>Thr<br>55 | TTG<br>Leu | GTG<br>Val | TTT<br>Phe | CAT<br>His | AAT<br>Asn<br>60 | CTC<br>Leu | TTG<br>Leu | GGT<br>Gly | 254 |
| GAA<br>Glu | ATT<br>Ile | GAC<br>Asp | CAG<br>Gln<br>65 | CAA<br>Gln | TAT<br>Tyr | AGC<br>Ser | CGA<br>Arg | TTC<br>Phe<br>70 | CTG<br>Leu | CAA<br>Gln | GAG<br>Glu | TCC<br>Ser | AAT<br>Asn<br>75 | GTC<br>Val | CTC<br>Leu | 302 |
| TAT<br>Tyr | CAG<br>Gln | CAC<br>His<br>80 | AAC<br>Asn | CTT<br>Leu | CGA<br>Arg | AGA<br>Arg | ATC<br>Ile<br>85 | AAG<br>Lys | CAG<br>Gln | TTT<br>Phe | CTG<br>Leu | CAG<br>Gln<br>90 | AGC<br>Ser | AGG<br>Arg | TAT<br>Tyr | 350 |
| CTT<br>Leu<br>95 | GAG<br>Glu | AAG<br>Lys | CCA<br>Pro | ATG<br>Met | GAA<br>Glu<br>100 | ATT<br>Ile | GCC<br>Ala | CGG<br>Arg | ATC<br>Ile | GTG<br>Val<br>105 | GCC<br>Ala | CGA<br>Arg | TGC<br>Cys | CTG<br>Leu | TGG<br>Trp<br>110 | 398 |
| GAA<br>Glu | GAG<br>Glu | TCT<br>Ser | CGC<br>Arg | CTC<br>Leu<br>115 | CTC<br>Leu | CAG<br>Gln | ACG<br>Thr | GCA<br>Ala | GCC<br>Ala<br>120 | ACG<br>Thr | GCA<br>Ala | GCC<br>Ala | CAG<br>Gln | CAA<br>Gln<br>125 | GGG<br>Gly | 446 |
| GGC<br>Gly | CAG<br>Gln | GCC<br>Ala | AAC<br>Asn<br>130 | CAC<br>His | CCA<br>Pro | ACA<br>Thr | GCC<br>Ala | GCC<br>Ala<br>135 | GTA<br>Val | GTG<br>Val | ACA<br>Thr | GAG<br>Glu | AAG<br>Lys<br>140 | CAG<br>Gln | CAG<br>Gln | 494 |
| ATG<br>Met | TTG<br>Leu | GAG<br>Glu<br>145 | CAG<br>Gln | CAT<br>His | CTT<br>Leu | CAG<br>Gln | GAT<br>Asp<br>150 | GTC<br>Val | CGG<br>Arg | AAG<br>Lys | CGA<br>Arg | GTG<br>Val<br>155 | CAG<br>Gln | GAT<br>Asp | CTA<br>Leu | 542 |
| GAA<br>Glu | CAG<br>Gln | AAA<br>Lys<br>160 | ATG<br>Met | AAG<br>Lys | GTG<br>Val | GTG<br>Val | GAG<br>Glu<br>165 | AAC<br>Asn | CTC<br>Leu | CAG<br>Gln | GAC<br>Asp | GAC<br>Asp<br>170 | TTT<br>Phe | GAT<br>Asp | TTC<br>Phe | 590 |
| AAC<br>Asn | TAC<br>Tyr<br>175 | AAA<br>Lys | ACC<br>Thr | CTC<br>Leu | AAG<br>Lys | AGC<br>Ser<br>180 | CAA<br>Gln | GGA<br>Gly | GAC<br>Asp | ATG<br>Met | CAG<br>Gln<br>185 | GAT<br>Asp | CTG<br>Leu | AAT<br>Asn | GGA<br>Gly<br>190 | 638 |
| AAC<br>Asn | AAC<br>Asn | CAG<br>Gln | TCT<br>Ser | GTG<br>Val<br>195 | ACC<br>Thr | AGA<br>Arg | CAG<br>Gln | AAG<br>Lys | ATG<br>Met<br>200 | CAG<br>Gln | CAG<br>Gln | CTG<br>Leu | GAA<br>Glu | CAG<br>Gln<br>205 | ATG<br>Met | 686 |
| CTC<br>Leu | ACA<br>Thr | GCC<br>Ala | CTG<br>Leu<br>210 | GAC<br>Asp | CAG<br>Gln | ATG<br>Met | CGG<br>Arg | AGA<br>Arg<br>215 | AGC<br>Ser | ATT<br>Ile | GTG<br>Val | AGT<br>Ser | GAG<br>Glu<br>220 | CTG<br>Leu | GCG<br>Ala | 734 |
| GGG<br>Gly | CTC<br>Leu | TTG<br>Leu | TCA<br>Ser<br>225 | GCA<br>Ala | ATG<br>Met | GAG<br>Glu | TAC<br>Tyr | GTG<br>Val<br>230 | CAG<br>Gln | AAG<br>Lys | ACA<br>Thr | CTG<br>Leu | ACT<br>Thr<br>235 | GAT<br>Asp | GAA<br>Glu | 782 |
| GAG<br>Glu | CTG<br>Leu | GCT<br>Ala | GAC<br>Asp | TGG<br>Trp | AAG<br>Lys | AGG<br>Arg | CGG<br>Arg | CCA<br>Pro | GAG<br>Glu | ATC<br>Ile | GCG<br>Ala | TGC<br>Cys | ATC<br>Ile | GGA<br>Gly | GGC<br>Gly | 830 |

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     | 240 |     |     |     |     | 245 |     |     |     |     | 250 |     |     |     |      |
| CCT | CCC | AAC | ATC | TGC | CTG | GAC | CGT | CTG | GAA | AAC | TGG | ATA | ACT | TCA | TTA | 878  |
| Pro | Pro | Asn | Ile | Cys | Leu | Asp | Arg | Leu | Glu | Asn | Trp | Ile | Thr | Ser | Leu |      |
| 255 |     |     |     | 260 |     |     |     |     | 265 |     |     |     |     |     | 270 |      |
| GCA | GAA | TCT | CAA | CTT | CAG | ACC | CGC | CAA | CAA | ATT | AAG | AAA | CTG | GAG | GAG | 926  |
| Ala | Glu | Ser | Gln | Leu | Gln | Thr | Arg | Gln | Gln | Ile | Lys | Lys | Leu | Glu | Glu |      |
|     |     |     |     |     | 275 |     |     |     |     | 280 |     |     |     |     | 285 |      |
| CTG | CAG | CAG | AAA | GTG | TCC | TAC | AAG | GGC | GAC | CCT | ATC | GTG | CAG | CAC | CGG | 974  |
| Leu | Gln | Gln | Lys | Val | Ser | Tyr | Lys | Gly | Asp | Pro | Ile | Val | Gln | His | Arg |      |
|     |     |     | 290 |     |     |     |     | 295 |     |     |     |     | 300 |     |     |      |
| CCC | ATG | CTG | GAG | GAG | AGG | ATC | GTG | GAG | CTG | TTC | AGA | AAC | TTA | ATG | AAG | 1022 |
| Pro | Met | Leu | Glu | Glu | Arg | Ile | Val | Glu | Leu | Phe | Arg | Asn | Leu | Met | Lys |      |
|     |     | 305 |     |     |     |     | 310 |     |     |     |     |     | 315 |     |     |      |
| AGT | GCC | TTC | GTG | GTG | GAG | CGG | CAG | CCC | TGC | ATG | CCC | ATG | CAC | CCG | GAC | 1070 |
| Ser | Ala | Phe | Val | Val | Glu | Arg | Gln | Pro | Cys | Met | Pro | Met | His | Pro | Asp |      |
|     | 320 |     |     |     |     | 325 |     |     |     |     | 330 |     |     |     |     |      |
| CGG | CCC | TTA | GTC | ATC | AAG | ACT | GGT | GTC | CAG | TTT | ACC | ACG | AAA | GTC | AGG | 1118 |
| Arg | Pro | Leu | Val | Ile | Lys | Thr | Gly | Val | Gln | Phe | Thr | Thr | Lys | Val | Arg |      |
| 335 |     |     |     |     | 340 |     |     |     |     | 345 |     |     |     |     | 350 |      |
| TTG | CTG | GTC | AAA | TTT | CCT | GAG | TTG | AAT | TAT | CAG | CTT | AAA | ATT | AAA | GTG | 1166 |
| Leu | Leu | Val | Lys | Phe | Pro | Glu | Leu | Asn | Tyr | Gln | Leu | Lys | Ile | Lys | Val |      |
|     |     |     |     | 355 |     |     |     |     | 360 |     |     |     |     | 365 |     |      |
| TGC | ATT | GAT | AAA | GAC | TCT | GGG | GAT | GTT | GCT | GCC | CTC | AGA | GGG | TCT | CGG | 1214 |
| Cys | Ile | Asp | Lys | Asp | Ser | Gly | Asp | Val | Ala | Ala | Leu | Arg | Gly | Ser | Arg |      |
|     |     |     | 370 |     |     |     |     | 375 |     |     |     |     | 380 |     |     |      |
| AAA | TTT | AAC | ATT | CTG | GGC | ACG | AAC | ACA | AAA | GTG | ATG | AAC | ATG | GAG | GAG | 1262 |
| Lys | Phe | Asn | Ile | Leu | Gly | Thr | Asn | Thr | Lys | Val | Met | Asn | Met | Glu | Glu |      |
|     |     | 385 |     |     |     |     | 390 |     |     |     |     |     | 395 |     |     |      |
| TCT | AAC | AAC | GGC | AGC | CTG | TCT | GCA | GAG | TTC | AAG | CAC | CTG | ACC | CTT | AGG | 1310 |
| Ser | Asn | Asn | Gly | Ser | Leu | Ser | Ala | Glu | Phe | Lys | His | Leu | Thr | Leu | Arg |      |
|     | 400 |     |     |     |     | 405 |     |     |     |     | 410 |     |     |     |     |      |
| GAG | CAG | AGA | TGT | GGG | AAT | GGA | GGC | CGT | GCC | AAT | TGT | GAT | GCC | TCC | TTG | 1358 |
| Glu | Gln | Arg | Cys | Gly | Asn | Gly | Gly | Arg | Ala | Asn | Cys | Asp | Ala | Ser | Leu |      |
| 415 |     |     |     |     | 420 |     |     |     |     | 425 |     |     |     |     | 430 |      |
| ATC | GTG | ACT | GAG | GAG | CTG | CAC | CTG | ATC | ACC | TTC | GAG | ACT | GAG | GTG | TAC | 1406 |
| Ile | Val | Thr | Glu | Glu | Leu | His | Leu | Ile | Thr | Phe | Glu | Thr | Glu | Val | Tyr |      |
|     |     |     |     | 435 |     |     |     |     | 440 |     |     |     |     | 445 |     |      |
| CAC | CAA | GGC | CTC | AAG | ATT | GAC | CTA | GAG | ACC | CAC | TCC | TTG | CCA | GTT | GTG | 1454 |
| His | Gln | Gly | Leu | Lys | Ile | Asp | Leu | Glu | Thr | His | Ser | Leu | Pro | Val | Val |      |
|     |     |     | 450 |     |     |     |     | 455 |     |     |     |     | 460 |     |     |      |
| GTG | ATC | TCC | AAC | ATC | TGT | CAG | ATG | CCA | AAT | GCT | TGG | GCA | TCA | ATC | CTG | 1502 |
| Val | Ile | Ser | Asn | Ile | Cys | Gln | Met | Pro | Asn | Ala | Trp | Ala | Ser | Ile | Leu |      |
|     |     | 465 |     |     |     |     | 470 |     |     |     |     | 475 |     |     |     |      |
| TGG | TAT | AAC | ATG | CTG | ACC | AAT | AAC | CCC | AAG | AAC | GTG | AAC | TTC | TTC | ACT | 1550 |
| Trp | Tyr | Asn | Met | Leu | Thr | Asn | Asn | Pro | Lys | Asn | Val | Asn | Phe | Phe | Thr |      |
|     | 480 |     |     |     |     | 485 |     |     |     |     | 490 |     |     |     |     |      |
| AAG | CCG | CCA | ATT | GGA | ACC | TGG | GAC | CAA | GTG | GCC | GAG | GTG | CTC | AGC | TGG | 1598 |
| Lys | Pro | Pro | Ile | Gly | Thr | Trp | Asp | Gln | Val | Ala | Glu | Val | Leu | Ser | Trp |      |
| 495 |     |     |     |     | 500 |     |     |     |     | 505 |     |     |     |     | 510 |      |
| CAG | TTC | TCG | TCC | ACC | ACC | AAG | CGA | GGG | CTG | AGC | ATC | GAG | CAG | CTG | ACA | 1646 |
| Gln | Phe | Ser | Ser | Thr | Thr | Lys | Arg | Gly | Leu | Ser | Ile | Glu | Gln | Leu | Thr |      |
|     |     |     |     | 515 |     |     |     |     | 520 |     |     |     |     | 525 |     |      |
| ACG | CTG | GCT | GAG | AAG | CTC | CTA | GGG | CCT | GGT | GTG | AAC | TAC | TCA | GGG | TGT | 1694 |
| Thr | Leu | Ala | Glu | Lys | Leu | Leu | Gly | Pro | Gly | Val | Asn | Tyr | Ser | Gly | Cys |      |
|     |     |     | 530 |     |     |     |     | 535 |     |     |     |     | 540 |     |     |      |
| CAG | ATC | ACA | TGG | GCT | AAA | TTC | TGC | AAA | GAA | AAC | ATG | GCT | GGC | AAG | GGC | 1742 |
| Gln | Ile | Thr | Trp | Ala | Lys | Phe | Cys | Lys | Glu | Asn | Met | Ala | Gly | Lys | Gly |      |
|     |     | 545 |     |     |     |     | 550 |     |     |     |     | 555 |     |     |     |      |
| TTC | TCC | TTC | TGG | GTC | TGG | CTA | GAC | AAT | ATC | ATC | GAC | CTT | GTG | AAA | AAG | 1790 |
| Phe | Ser | Phe | Trp | Val | Trp | Leu | Asp | Asn | Ile | Ile | Asp | Leu | Val | Lys | Lys |      |

|  |  |  |  |  |  |  |  |  |  |  |  |  |  |  |  |  |
|---|---|---|---|---|---|---|---|---|---|---|---|---|---|---|---|---|
|  |  |  | 560 |  |  |  |  | 565 |  |  |  |  | 570 |  |  |  |
| TAT | ATC | TTG | GCC | CTT | TGG | AAT | GAA | GGG | TAC | ATC | ATG | GGT | TTC | ATC | AGC | 1838 |
| Tyr | Ile | Leu | Ala | Leu | Trp | Asn | Glu | Gly | Tyr | Ile | Met | Gly | Phe | Ile | Ser |  |
| 575 |  |  |  |  | 580 |  |  |  |  | 585 |  |  |  |  | 590 |  |
| AAG | GAG | CGG | GAG | CGG | GCC | ATC | CTA | AGC | ACA | AAG | CCC | CCG | GGC | ACC | TTC | 1886 |
| Lys | Glu | Arg | Glu | Arg | Ala | Ile | Leu | Ser | Thr | Lys | Pro | Pro | Gly | Thr | Phe |  |
|  |  |  |  | 595 |  |  |  |  | 600 |  |  |  |  | 605 |  |  |
| CTA | CTG | CGC | TTC | AGC | GAG | AGC | AGC | AAA | GAA | GGA | GGG | GTC | ACT | TTC | ACT | 1934 |
| Leu | Leu | Arg | Phe | Ser | Glu | Ser | Ser | Lys | Glu | Gly | Gly | Val | Thr | Phe | Thr |  |
|  |  |  | 610 |  |  |  |  | 615 |  |  |  |  | 620 |  |  |  |
| TGG | GTG | GAA | AAG | GAC | ATC | AGT | GGC | AAG | ACC | CAG | ATC | CAG | TCT | GTA | GAG | 1982 |
| Trp | Val | Glu | Lys | Asp | Ile | Ser | Gly | Lys | Thr | Gln | Ile | Gln | Ser | Val | Glu |  |
|  |  | 625 |  |  |  |  | 630 |  |  |  |  | 635 |  |  |  |  |
| CCA | TAC | ACC | AAG | CAG | CAG | CTG | AAC | AAC | ATG | TCA | TTT | GCT | GAA | ATC | ATC | 2030 |
| Pro | Tyr | Thr | Lys | Gln | Gln | Leu | Asn | Asn | Met | Ser | Phe | Ala | Glu | Ile | Ile |  |
|  | 640 |  |  |  |  | 645 |  |  |  |  | 650 |  |  |  |  |  |
| ATG | GGC | TAT | AAG | ATC | ATG | GAT | GCG | ACC | AAC | ATC | CTG | GTG | TCT | CCA | CTT | 2078 |
| Met | Gly | Tyr | Lys | Ile | Met | Asp | Ala | Thr | Asn | Ile | Leu | Val | Ser | Pro | Leu |  |
| 655 |  |  |  |  | 660 |  |  |  |  | 665 |  |  |  |  | 670 |  |
| GTC | TAC | CTC | TAC | CCC | GAC | ATT | CCC | AAG | GAG | GAG | GCA | TTT | GGA | AAG | TAC | 2126 |
| Val | Tyr | Leu | Tyr | Pro | Asp | Ile | Pro | Lys | Glu | Glu | Ala | Phe | Gly | Lys | Tyr |  |
|  |  |  |  | 675 |  |  |  |  | 680 |  |  |  |  | 685 |  |  |
| TGT | AGG | CCC | GAG | AGC | CAG | GAG | CAC | CCC | GAA | GCC | GAC | CCA | GGT | AGT | GCT | 2174 |
| Cys | Arg | Pro | Glu | Ser | Gln | Glu | His | Pro | Glu | Ala | Asp | Pro | Gly | Ser | Ala |  |
|  |  |  | 690 |  |  |  |  | 695 |  |  |  |  | 700 |  |  |  |
| GCC | CCG | TAC | CTG | AAG | ACC | AAG | TTC | ATC | TGT | GTG | ACA | CCA | ACG | ACC | TGC | 2222 |
| Ala | Pro | Tyr | Leu | Lys | Thr | Lys | Phe | Ile | Cys | Val | Thr | Pro | Thr | Thr | Cys |  |
|  |  | 705 |  |  |  |  | 710 |  |  |  |  | 715 |  |  |  |  |
| AGC | AAT | ACC | ATT | GAC | CTG | CCG | ATG | TCC | CCC | CGC | ACT | TTA | GAT | TCA | TTG | 2270 |
| Ser | Asn | Thr | Ile | Asp | Leu | Pro | Met | Ser | Pro | Arg | Thr | Leu | Asp | Ser | Leu |  |
|  | 720 |  |  |  |  | 725 |  |  |  |  | 730 |  |  |  |  |  |
| ATG | CAG | TTT | GGA | AAT | AAC | GGT | GAA | GGT | GCT | GAG | CCC | TCA | GCA | GGA | GGG | 2318 |
| Met | Gln | Phe | Gly | Asn | Asn | Gly | Glu | Gly | Ala | Glu | Pro | Ser | Ala | Gly | Gly |  |
| 735 |  |  |  |  | 740 |  |  |  |  | 745 |  |  |  |  | 750 |  |
| CAG | TTT | GAG | TCG | CTC | ACG | TTT | GAC | ATG | GAT | CTG | ACC | TCG | GAG | TGT | GCT | 2366 |
| Gln | Phe | Glu | Ser | Leu | Thr | Phe | Asp | Met | Asp | Leu | Thr | Ser | Glu | Cys | Ala |  |
|  |  |  |  | 755 |  |  |  |  | 760 |  |  |  |  | 765 |  |  |
| ACC | TCC | CCC | ATG | TGAGGAGCTG | AAACCAGAAG | CTGCAGAGAC | GTGACTTGAG |  |  |  |  |  |  |  |  | 2418 |
| Thr | Ser | Pro | Met |  |  |  |  |  |  |  |  |  |  |  |  |  |
|  |  |  | 770 |  |  |  |  |  |  |  |  |  |  |  |  |  |

```
ACACCTGCCC CGTGCTCCAC CCCTAAGCAG CCGAACCCCA TATCGTCTGA AACTCCTA      2478

TTTGTGGTTC CAGATTTTTT TTTTAATTT  CCTACTTCTG CTATCTTTGG GCAATCTG      2538

CACTTTTTAA AAGAGAGAAA TGAGTGAGTG TGGGTGATAA ACTGTTATGT AAAGAGGA      2598

GACCTCTGAG TCTGGGGATG GGGCTGAGAG CAGAAGGGAG GCAAAGGGGA ACACCTCC      2658

TCCTGCCCGC CTGCCCTCCT TTTTCAGCAG CTCGGGGGTT GGTTGTTAGA CAAGTGCC      2718

CTGGTGCCCA TGGCTACCTG TTGCCCCACT CTGTGAGCTG ATACCCCATT CTGGGAAC      2778

CTGGCTCTGC ACTTTCAACC TTGCTAATAT CCACATAGAA GCTAGGACTA AGCCCAGG      2838

GTTCCTCTTT AAATTAAAAA AAAAAAAAA A                                    2869
```

( 2 ) INFORMATION FOR SEQ ID NO:12:

( i ) SEQUENCE CHARACTERISTICS:
( A ) LENGTH: 770 amino acids
( B ) TYPE: amino acid
( D ) TOPOLOGY: linear ( i i ) MOLECULE TYPE: protein ( x i ) SEQUENCE DESCRIPTION: SEQ ID NO:12:

| Met | Ala | Gln | Trp | Asn | Gln | Leu | Gln | Gln | Leu | Asp | Thr | Arg | Tyr | Leu | Lys |
|---|---|---|---|---|---|---|---|---|---|---|---|---|---|---|---|
| 1 | | | | 5 | | | | | 10 | | | | | 15 | |

| Gln | Leu | His | Gln | Leu | Tyr | Ser | Asp | Thr | Phe | Pro | Met | Glu | Leu | Arg | Gln |
|---|---|---|---|---|---|---|---|---|---|---|---|---|---|---|---|
| | | | 20 | | | | | 25 | | | | | 30 | | |

| Phe | Leu | Ala | Pro | Trp | Ile | Glu | Ser | Gln | Asp | Trp | Ala | Tyr | Ala | Ala | Ser |
|---|---|---|---|---|---|---|---|---|---|---|---|---|---|---|---|
| | | 35 | | | | | 40 | | | | | 45 | | | |

| Lys | Glu | Ser | His | Ala | Thr | Leu | Val | Phe | His | Asn | Leu | Leu | Gly | Glu | Ile |
|---|---|---|---|---|---|---|---|---|---|---|---|---|---|---|---|
| | 50 | | | | | 55 | | | | | 60 | | | | |

| Asp | Gln | Gln | Tyr | Ser | Arg | Phe | Leu | Gln | Glu | Ser | Asn | Val | Leu | Tyr | Gln |
|---|---|---|---|---|---|---|---|---|---|---|---|---|---|---|---|
| 65 | | | | | 70 | | | | | 75 | | | | | 80 |

| His | Asn | Leu | Arg | Arg | Ile | Lys | Gln | Phe | Leu | Gln | Ser | Arg | Tyr | Leu | Glu |
|---|---|---|---|---|---|---|---|---|---|---|---|---|---|---|---|
| | | | | 85 | | | | | 90 | | | | | 95 | |

| Lys | Pro | Met | Glu | Ile | Ala | Arg | Ile | Val | Ala | Arg | Cys | Leu | Trp | Glu | Glu |
|---|---|---|---|---|---|---|---|---|---|---|---|---|---|---|---|
| | | | 100 | | | | | 105 | | | | | 110 | | |

| Ser | Arg | Leu | Leu | Gln | Thr | Ala | Ala | Thr | Ala | Ala | Gln | Gln | Gly | Gly | Gln |
|---|---|---|---|---|---|---|---|---|---|---|---|---|---|---|---|
| | | | 115 | | | | | 120 | | | | | 125 | | |

| Ala | Asn | His | Pro | Thr | Ala | Ala | Val | Val | Thr | Glu | Lys | Gln | Gln | Met | Leu |
|---|---|---|---|---|---|---|---|---|---|---|---|---|---|---|---|
| | 130 | | | | | 135 | | | | | 140 | | | | |

| Glu | Gln | His | Leu | Gln | Asp | Val | Arg | Lys | Arg | Val | Gln | Asp | Leu | Glu | Gln |
|---|---|---|---|---|---|---|---|---|---|---|---|---|---|---|---|
| 145 | | | | | 150 | | | | | 155 | | | | | 160 |

| Lys | Met | Lys | Val | Val | Glu | Asn | Leu | Gln | Asp | Asp | Phe | Asp | Phe | Asn | Tyr |
|---|---|---|---|---|---|---|---|---|---|---|---|---|---|---|---|
| | | | | 165 | | | | | 170 | | | | | 175 | |

| Lys | Thr | Leu | Lys | Ser | Gln | Gly | Asp | Met | Gln | Asp | Leu | Asn | Gly | Asn | Asn |
|---|---|---|---|---|---|---|---|---|---|---|---|---|---|---|---|
| | | | 180 | | | | | 185 | | | | | 190 | | |

| Gln | Ser | Val | Thr | Arg | Gln | Lys | Met | Gln | Gln | Leu | Glu | Gln | Met | Leu | Thr |
|---|---|---|---|---|---|---|---|---|---|---|---|---|---|---|---|
| | | 195 | | | | | 200 | | | | | 205 | | | |

| Ala | Leu | Asp | Gln | Met | Arg | Arg | Ser | Ile | Val | Ser | Glu | Leu | Ala | Gly | Leu |
|---|---|---|---|---|---|---|---|---|---|---|---|---|---|---|---|
| | 210 | | | | | 215 | | | | | 220 | | | | |

| Leu | Ser | Ala | Met | Glu | Tyr | Val | Gln | Lys | Thr | Leu | Thr | Asp | Glu | Glu | Leu |
|---|---|---|---|---|---|---|---|---|---|---|---|---|---|---|---|
| 225 | | | | | 230 | | | | | 235 | | | | | 240 |

| Ala | Asp | Trp | Lys | Arg | Arg | Pro | Glu | Ile | Ala | Cys | Ile | Gly | Gly | Pro | Pro |
|---|---|---|---|---|---|---|---|---|---|---|---|---|---|---|---|
| | | | | 245 | | | | | 250 | | | | | 255 | |

| Asn | Ile | Cys | Leu | Asp | Arg | Leu | Glu | Asn | Trp | Ile | Thr | Ser | Leu | Ala | Glu |
|---|---|---|---|---|---|---|---|---|---|---|---|---|---|---|---|
| | | | 260 | | | | | 265 | | | | | 270 | | |

| Ser | Gln | Leu | Gln | Thr | Arg | Gln | Gln | Ile | Lys | Lys | Leu | Glu | Glu | Leu | Gln |
|---|---|---|---|---|---|---|---|---|---|---|---|---|---|---|---|
| | | 275 | | | | | 280 | | | | | 285 | | | |

| Gln | Lys | Val | Ser | Tyr | Lys | Gly | Asp | Pro | Ile | Val | Gln | His | Arg | Pro | Met |
|---|---|---|---|---|---|---|---|---|---|---|---|---|---|---|---|
| | 290 | | | | | 295 | | | | | 300 | | | | |

| Leu | Glu | Glu | Arg | Ile | Val | Glu | Leu | Phe | Arg | Asn | Leu | Met | Lys | Ser | Ala |
|---|---|---|---|---|---|---|---|---|---|---|---|---|---|---|---|
| 305 | | | | | 310 | | | | | 315 | | | | | 320 |

| Phe | Val | Val | Glu | Arg | Gln | Pro | Cys | Met | Pro | Met | His | Pro | Asp | Arg | Pro |
|---|---|---|---|---|---|---|---|---|---|---|---|---|---|---|---|
| | | | | 325 | | | | | 330 | | | | | 335 | |

| Leu | Val | Ile | Lys | Thr | Gly | Val | Gln | Phe | Thr | Thr | Lys | Val | Arg | Leu | Leu |
|---|---|---|---|---|---|---|---|---|---|---|---|---|---|---|---|
| | | | 340 | | | | | 345 | | | | | 350 | | |

| Val | Lys | Phe | Pro | Glu | Leu | Asn | Tyr | Gln | Leu | Lys | Ile | Lys | Val | Cys | Ile |
|---|---|---|---|---|---|---|---|---|---|---|---|---|---|---|---|
| | | 355 | | | | | 360 | | | | | 365 | | | |

| Asp | Lys | Asp | Ser | Gly | Asp | Val | Ala | Ala | Leu | Arg | Gly | Ser | Arg | Lys | Phe |
|---|---|---|---|---|---|---|---|---|---|---|---|---|---|---|---|
| | 370 | | | | | 375 | | | | | 380 | | | | |

| Asn | Ile | Leu | Gly | Thr | Asn | Thr | Lys | Val | Met | Asn | Met | Glu | Glu | Ser | Asn |
|---|---|---|---|---|---|---|---|---|---|---|---|---|---|---|---|
| 385 | | | | | 390 | | | | | 395 | | | | | 400 |

| Asn | Gly | Ser | Leu | Ser | Ala | Glu | Phe | Lys | His | Leu | Thr | Leu | Arg | Glu | Gln |
|---|---|---|---|---|---|---|---|---|---|---|---|---|---|---|---|
| | | | | 405 | | | | | 410 | | | | | 415 | |

```
Arg  Cys  Gly  Asn  Gly  Gly  Arg  Ala  Asn  Cys  Asp  Ala  Ser  Leu  Ile  Val
               420                      425                      430

Thr  Glu  Glu  Leu  His  Leu  Ile  Thr  Phe  Glu  Thr  Glu  Val  Tyr  His  Gln
          435                      440                      445

Gly  Leu  Lys  Ile  Asp  Leu  Glu  Thr  His  Ser  Leu  Pro  Val  Val  Val  Ile
          450                      455                      460

Ser  Asn  Ile  Cys  Gln  Met  Pro  Asn  Ala  Trp  Ala  Ser  Ile  Leu  Trp  Tyr
465                      470                      475                      480

Asn  Met  Leu  Thr  Asn  Asn  Pro  Lys  Asn  Val  Asn  Phe  Phe  Thr  Lys  Pro
                    485                      490                      495

Pro  Ile  Gly  Thr  Trp  Asp  Gln  Val  Ala  Glu  Val  Leu  Ser  Trp  Gln  Phe
               500                      505                      510

Ser  Ser  Thr  Thr  Lys  Arg  Gly  Leu  Ser  Ile  Glu  Gln  Leu  Thr  Thr  Leu
               515                      520                      525

Ala  Glu  Lys  Leu  Leu  Gly  Pro  Gly  Val  Asn  Tyr  Ser  Gly  Cys  Gln  Ile
     530                      535                      540

Thr  Trp  Ala  Lys  Phe  Cys  Lys  Glu  Asn  Met  Ala  Gly  Lys  Gly  Phe  Ser
545                      550                      555                      560

Phe  Trp  Val  Trp  Leu  Asp  Asn  Ile  Ile  Asp  Leu  Val  Lys  Lys  Tyr  Ile
                    565                      570                      575

Leu  Ala  Leu  Trp  Asn  Glu  Gly  Tyr  Ile  Met  Gly  Phe  Ile  Ser  Lys  Glu
               580                      585                      590

Arg  Glu  Arg  Ala  Ile  Leu  Ser  Thr  Lys  Pro  Pro  Gly  Thr  Phe  Leu  Leu
          595                      600                      605

Arg  Phe  Ser  Glu  Ser  Ser  Lys  Glu  Gly  Gly  Val  Thr  Phe  Thr  Trp  Val
     610                      615                      620

Glu  Lys  Asp  Ile  Ser  Gly  Lys  Thr  Gln  Ile  Gln  Ser  Val  Glu  Pro  Tyr
625                      630                      635                      640

Thr  Lys  Gln  Gln  Leu  Asn  Asn  Met  Ser  Phe  Ala  Glu  Ile  Ile  Met  Gly
                    645                      650                      655

Tyr  Lys  Ile  Met  Asp  Ala  Thr  Asn  Ile  Leu  Val  Ser  Pro  Leu  Val  Tyr
               660                      665                      670

Leu  Tyr  Pro  Asp  Ile  Pro  Lys  Glu  Glu  Ala  Phe  Gly  Lys  Tyr  Cys  Arg
          675                      680                      685

Pro  Glu  Ser  Gln  Glu  His  Pro  Glu  Ala  Asp  Pro  Gly  Ser  Ala  Ala  Pro
     690                      695                      700

Tyr  Leu  Lys  Thr  Lys  Phe  Ile  Cys  Val  Thr  Pro  Thr  Thr  Cys  Ser  Asn
705                      710                      715                      720

Thr  Ile  Asp  Leu  Pro  Met  Ser  Pro  Arg  Thr  Leu  Asp  Ser  Leu  Met  Gln
                    725                      730                      735

Phe  Gly  Asn  Asn  Gly  Glu  Gly  Ala  Glu  Pro  Ser  Ala  Gly  Gly  Gln  Phe
               740                      745                      750

Glu  Ser  Leu  Thr  Phe  Asp  Met  Asp  Leu  Thr  Ser  Glu  Cys  Ala  Thr  Ser
          755                      760                      765

Pro  Met
     770
```

( 2 ) INFORMATION FOR SEQ ID NO:13:

( i ) SEQUENCE CHARACTERISTICS:
        ( A ) LENGTH: 110 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:13:

| Ser | Leu | Ala | Ala | Glu | Phe | Arg | His | Leu | Gln | Leu | Lys | Glu | Gln | Lys | Asn |
|---|---|---|---|---|---|---|---|---|---|---|---|---|---|---|---|
| 1 | | | | 5 | | | | | 10 | | | | | 15 | |
| Ala | Gly | Thr | Arg | Thr | Asn | Glu | Gly | Pro | Leu | Ile | Val | Thr | Glu | Glu | Leu |
| | | | 20 | | | | | 25 | | | | | 30 | | |
| His | Ser | Leu | Ser | Phe | Glu | Thr | Gln | Leu | Cys | Gln | Pro | Gly | Leu | Val | Ile |
| | | | 35 | | | | 40 | | | | | 45 | | | |
| Asp | Leu | Glu | Thr | Thr | Ser | Leu | Pro | Val | Val | Val | Ile | Ser | Asn | Val | Ser |
| | | 50 | | | | | 55 | | | | | 60 | | | |
| Gln | Leu | Pro | Ser | Gly | Trp | Ala | Ser | Ile | Leu | Trp | Tyr | Asn | Met | Leu | Val |
| 65 | | | | | 70 | | | | | 75 | | | | | 80 |
| Ala | Glu | Pro | Arg | Asn | Leu | Ser | Phe | Phe | Leu | Thr | Pro | Pro | Cys | Ala | Arg |
| | | | | 85 | | | | | 90 | | | | | 95 | |
| Trp | Ala | Gln | Leu | Ser | Glu | Val | Leu | Ser | Trp | Gln | Phe | Ser | Ser | | |
| | | | 100 | | | | | 105 | | | | | 110 | | |

( 2 ) INFORMATION FOR SEQ ID NO:14:

( i ) SEQUENCE CHARACTERISTICS:
( A ) LENGTH: 112 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:14:

| Ser | Leu | Ser | Ala | Glu | Phe | Lys | His | Leu | Thr | Leu | Arg | Glu | Gln | Arg | Cys |
|---|---|---|---|---|---|---|---|---|---|---|---|---|---|---|---|
| 1 | | | | 5 | | | | | 10 | | | | | 15 | |
| Gly | Asn | Gly | Gly | Arg | Ala | Asn | Cys | Asp | Ala | Ser | Leu | Ile | Val | Thr | Glu |
| | | | 20 | | | | | 25 | | | | | 30 | | |
| Glu | Leu | His | Leu | Ile | Thr | Phe | Glu | Thr | Glu | Val | Tyr | His | Gln | Gly | Leu |
| | | | 35 | | | | | 40 | | | | | 45 | | |
| Lys | Ile | Asp | Leu | Glu | Thr | His | Ser | Leu | Pro | Val | Val | Val | Ile | Ser | Asn |
| | | 50 | | | | | 55 | | | | | 60 | | | |
| Ile | Cys | Gln | Met | Pro | Asn | Ala | Trp | Ala | Ser | Ile | Leu | Trp | Tyr | Asn | Met |
| 65 | | | | | 70 | | | | | 75 | | | | | 80 |
| Leu | Thr | Asn | Asn | Pro | Lys | Asn | Val | Asn | Phe | Phe | Thr | Lys | Pro | Pro | Ile |
| | | | | 85 | | | | | 90 | | | | | 95 | |
| Gly | Thr | Trp | Asp | Gln | Val | Ala | Glu | Val | Leu | Ser | Trp | Gln | Phe | Ser | Ser |
| | | | 100 | | | | | 105 | | | | | 110 | | |

( 2 ) INFORMATION FOR SEQ ID NO:15:

( i ) SEQUENCE CHARACTERISTICS:
( A ) LENGTH: 111 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:15:

| Ser | Leu | Ser | Val | Glu | Phe | Arg | His | Leu | Gln | Pro | Lys | Glu | Met | Lys | Cys |
| 1 | | | | 5 | | | | | 10 | | | | | 15 | |

| Ser | Thr | Gly | Ser | Lys | Gly | Asn | Glu | Gly | Cys | His | Met | Val | Thr | Glu | Glu |
| | | | 20 | | | | | 25 | | | | | 30 | | |

| Leu | His | Ser | Ile | Thr | Phe | Glu | Thr | Gln | Ile | Cys | Leu | Tyr | Gly | Leu | Thr |
| | | 35 | | | | | 40 | | | | | 45 | | | |

| Ile | Asn | Leu | Glu | Thr | Ser | Ser | Leu | Pro | Val | Val | Met | Ile | Ser | Asn | Val |
| | 50 | | | | | 55 | | | | | 60 | | | | |

| Ser | Gln | Leu | Pro | Asn | Ala | Trp | Ala | Ser | Ile | Ile | Trp | Tyr | Asn | Val | Ser |
| 65 | | | | | 70 | | | | | 75 | | | | | 80 |

| Thr | Asn | Asp | Ser | Gln | Asn | Leu | Val | Phe | Phe | Asn | Asn | Pro | Pro | Ser | Val |
| | | | | 85 | | | | | 90 | | | | | 95 | |

| Thr | Leu | Gly | Gln | Leu | Leu | Glu | Val | Met | Ser | Trp | Gln | Phe | Ser | Ser |
| | | | 100 | | | | | 105 | | | | | 110 | |

( 2 ) INFORMATION FOR SEQ ID NO:16:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:16:

| Thr | Leu | Ser | Ala | His | Phe | Arg | Asn | Met | Ser | Leu | Lys | Arg | Ile | Lys | Arg |
| 1 | | | | 5 | | | | | 10 | | | | | 15 | |

| Ala | Asp | Arg | Arg | Gly | Ala | Glu | Ser | Val | Thr | Glu | Glu | Lys | Phe | Thr | Val |
| | | | 20 | | | | | 25 | | | | | 30 | | |

| Leu | Phe | Glu | Ser | Gln | Phe | Ser | Val | Gly | Ser | Asn | Glu | Leu | Val | Phe | Gln |
| | | | 35 | | | | | 40 | | | | | 45 | | |

| Val | Lys | Thr | Leu | Ser | Leu | Pro | Val | Val | Val | Ile | Val | His | Gly | Ser | Gln |
| | | 50 | | | | | 55 | | | | | 60 | | | |

| Asp | His | Asn | Ala | Thr | Ala | Thr | Val | Leu | Trp | Asp | Asn | Ala | Phe | Ala | Glu |
| 65 | | | | | 70 | | | | | 75 | | | | | 80 |

| Pro | Gly | Arg | Val | Pro | Phe | Ala | Val | Pro | Asp | Lys | Val | Leu | Trp | Pro | Gln |
| | | | | 85 | | | | | 90 | | | | | 95 | |

| Leu | Cys | Glu | Ala | Leu | Asn | Met | Lys | Phe | Lys | Ala |
| | | | 100 | | | | | 105 | | |

( 2 ) INFORMATION FOR SEQ ID NO:17:

( i ) SEQUENCE CHARACTERISTICS:
        ( A ) LENGTH: 107 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:17:

| Cys | Cys | Ser | Ala | Leu | Phe | Lys | Asn | Leu | Leu | Leu | Lys | Lys | Ile | Lys | Arg |
| 1 | | | | 5 | | | | | 10 | | | | | 15 | |

```
        Cys Glu Arg Lys Gly Thr Glu Ser Val Thr Glu Glu Lys Cys Ala Val
                     20                  25                  30

Leu Phe Ser Ala Ser Phe Thr Leu Gly Pro Gly Lys Leu Pro Ile Gln
                     35                  40                  45

Leu Gln Ala Leu Ser Leu Pro Leu Val Val Ile Val His Gly Asn Gln
                 50                  55                  60

Asp Asn Asn Ala Lys Ala Thr Ile Leu Trp Asp Asn Ala Phe Ser Glu
        65                   70                  75                  80

Met Asp Arg Val Pro Phe Val Val Ala Glu Arg Val Pro Trp Glu Lys
                         85                  90                  95

Met Cys Glu Thr Leu Asn Leu Lys Phe Met Ala
                        100                 105
```

( 2 ) INFORMATION FOR SEQ ID NO:18:

( i ) SEQUENCE CHARACTERISTICS:
        ( A ) LENGTH: 111 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:18:

```
        Leu Ile Trp Asp Phe Gly Tyr Leu Thr Leu Val Glu Gln Arg Ser Gly
        1                5                   10                  15

Gly Ser Gly Lys Gly Ser Asn Lys Gly Pro Leu Gly Val Thr Glu Glu
                     20                  25                  30

Leu His Ile Ile Ser Phe Thr Val Lys Tyr Thr Tyr Gln Gly Leu Lys
                     35                  40                  45

Gln Glu Leu Lys Thr Asp Thr Leu Pro Val Val Ile Ile Ser Asn Met
                 50                  55                  60

Asn Gln Leu Ser Ile Ala Trp Ala Ser Val Leu Trp Phe Asn Leu Leu
        65                   70                  75                  80

Ser Pro Asn Leu Gln Asn Gln Gln Phe Phe Ser Asn Pro Pro Lys Ala
                         85                  90                  95

Pro Trp Ser Leu Leu Gly Pro Ala Leu Ser Trp Gln Phe Ser Ser
                        100                 105                 110
```

( 2 ) INFORMATION FOR SEQ ID NO:19:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:19:

CAGTTCCCGT CAATCAT                             17

( 2 ) INFORMATION FOR SEQ ID NO:20:

( i ) SEQUENCE CHARACTERISTICS:

(A) LENGTH: 17 base pairs
(B) TYPE: nucleic acid
(C) STRANDEDNESS: double
(D) TOPOLOGY: linear (ii) MOLECULE TYPE: DNA synthetic probe (iii) HYPOTHETICAL: NO (iv) ANTI-SENSE: NO (xi) SEQUENCE DESCRIPTION: SEQ ID NO:20:

CATTTCCCGT AAATCAT    17

(2) INFORMATION FOR SEQ ID NO:21:

(i) SEQUENCE CHARACTERISTICS:
(A) LENGTH: 17 base pairs
(B) TYPE: nucleic acid
(C) STRANDEDNESS: double
(D) TOPOLOGY: linear (ii) MOLECULE TYPE: DNA synthetic probe (iii) HYPOTHETICAL: NO (iv) ANTI-SENSE: NO (xi) SEQUENCE DESCRIPTION: SEQ ID NO:21:

ATATTCCTGT AAGTGAT    17

(2) INFORMATION FOR SEQ ID NO:22:

(i) SEQUENCE CHARACTERISTICS:
(A) LENGTH: 17 base pairs
(B) TYPE: nucleic acid
(C) STRANDEDNESS: double
(D) TOPOLOGY: linear (ii) MOLECULE TYPE: DNA synthetic probe (iii) HYPOTHETICAL: NO (iv) ANTI-SENSE: NO (xi) SEQUENCE DESCRIPTION: SEQ ID NO:22:

GTATTTCCCA GAAAAGG    17

(2) INFORMATION FOR SEQ ID NO:23:

(i) SEQUENCE CHARACTERISTICS:
(A) LENGTH: 17 base pairs
(B) TYPE: nucleic acid
(C) STRANDEDNESS: double
(D) TOPOLOGY: linear (ii) MOLECULE TYPE: DNA synthetic probe (iii) HYPOTHETICAL: NO (iv) ANTI-SENSE: NO (xi) SEQUENCE DESCRIPTION: SEQ ID NO:23:

GTTGTTCCGG GAAAATT    17

(2) INFORMATION FOR SEQ ID NO:24:

(i) SEQUENCE CHARACTERISTICS:
(A) LENGTH: 17 base pairs
(B) TYPE: nucleic acid
(C) STRANDEDNESS: double
(D) TOPOLOGY: linear (i i) MOLECULE TYPE: DNA synthetic probe (i i i) HYPOTHETICAL: NO (i v) ANTI-SENSE: NO (x i) SEQUENCE DESCRIPTION: SEQ ID NO:24:

TATTTCCGGG AAATCCC 17

(2) INFORMATION FOR SEQ ID NO:25:

(i) SEQUENCE CHARACTERISTICS:
(A) LENGTH: 9 base pairs
(B) TYPE: nucleic acid
(C) STRANDEDNESS: double
(D) TOPOLOGY: linear (i i) MOLECULE TYPE: DNA synthetic probe (i i i) HYPOTHETICAL: NO (i v) ANTI-SENSE: NO (x i) SEQUENCE DESCRIPTION: SEQ ID NO:25:

TTCCCGGAA 9

(2) INFORMATION FOR SEQ ID NO:26:

(i) SEQUENCE CHARACTERISTICS:
(A) LENGTH: 9 base pairs
(B) TYPE: nucleic acid
(C) STRANDEDNESS: double
(D) TOPOLOGY: linear (i i) MOLECULE TYPE: DNA synthetic probe (i i i) HYPOTHETICAL: NO (i v) ANTI-SENSE: NO (x i) SEQUENCE DESCRIPTION: SEQ ID NO:26:

TTCCGGGAA 9

(2) INFORMATION FOR SEQ ID NO:27:

(i) SEQUENCE CHARACTERISTICS:
(A) LENGTH: 9 base pairs
(B) TYPE: nucleic acid
(C) STRANDEDNESS: double
(D) TOPOLOGY: linear (i i) MOLECULE TYPE: DNA synthetic probe (i i i) HYPOTHETICAL: NO (i v) ANTI-SENSE: NO (x i) SEQUENCE DESCRIPTION: SEQ ID NO:27:

TTCCGGGAA 9

(2) INFORMATION FOR SEQ ID NO:28:

(i) SEQUENCE CHARACTERISTICS:
(A) LENGTH: 9 base pairs
(B) TYPE: nucleic acid
(C) STRANDEDNESS: double
(D) TOPOLOGY: linear (i i) MOLECULE TYPE: DNA synthetic probe (i i i) HYPOTHETICAL: NO ( i v ) ANTI-SENSE: NO ( x i ) SEQUENCE DESCRIPTION: SEQ ID NO:28:

TTCCCGTAA 9

( 2 ) INFORMATION FOR SEQ ID NO:29:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:29:

TTCCCGTCA 9

( 2 ) INFORMATION FOR SEQ ID NO:30:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:30:

TTCCTGTAA 9

( 2 ) INFORMATION FOR SEQ ID NO:31:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:31:

TTCCCAGAA 9

( 2 ) INFORMATION FOR SEQ ID NO:32:

( i ) SEQUENCE CHARACTERISTICS:
( A ) LENGTH: 9 base pairs
( B ) TYPE: nucleic acid
( C ) STRANDEDNESS: double
( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:32:

TTACTCTAA    9

( 2 ) INFORMATION FOR SEQ ID NO:33:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:33:

TTACTATAA    9

( 2 ) INFORMATION FOR SEQ ID NO:34:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:34:

TTCTCAGAA    9

( 2 ) INFORMATION FOR SEQ ID NO:35:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:35:

TTCCCCGAA    9

( 2 ) INFORMATION FOR SEQ ID NO:36:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:36:

TTCTCGGAA    9

-continued ( 2 ) INFORMATION FOR SEQ ID NO:37:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:37:

T T C C C G T A A                 9

( 2 ) INFORMATION FOR SEQ ID NO:38:

( i ) SEQUENCE CHARACTERISTICS:
        ( A ) LENGTH: 9 base pairs
        ( B ) TYPE: nucleic acid
        ( C ) STRANDEDNESS: double
        ( D ) TOPOLOGY: linear ( i i ) MOLECULE TYPE: DNA synthetic probe ( i i i ) HYPOTHETICAL: NO ( i v ) ANTI-SENSE: NO ( x i ) SEQUENCE DESCRIPTION: SEQ ID NO:38:

T T C C C A G A A                 9

( 2 ) INFORMATION FOR SEQ ID NO:39:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: internal ( x i ) SEQUENCE DESCRIPTION: SEQ ID NO:39:

Gly  Ile  Tyr  Thr  Glu  Lys
                          5

What is claimed is:

1. A peptide corresponding to a DNA-binding domain of a STAT protein, Signal Transducer and Activator of Transcription, wherein said DNA-binding domain consists of an amino acid sequence selected from the group consisting of:
SEQ ID NO 13,
SEQ ID NO:14,
SEQ ID NO:15,
SEQ ID NO:16,
SEQ ID NO:17 and
SEQ ID NO:18.

2. An immunogenic composition comprising the peptide of claim 1 in an admixture with an adjuvant.

3. The composition of claim 2, wherein the peptide is further conjugated to a carrier molecule.

4. A chimeric protein consisting of a first STAT protein, Signal Transducer and Activator of Transcription, wherein the DNA-binding domain of said first STAT protein is substituted with the DNA binding domain of a second STAT protein, wherein the DNA binding domain of the second STAT protein is different from the DNA binding domain of the first STAT protein and corresponds to an amino acid sequence selected from the group consisting of:
SEQ ID NO 13,
SEQ ID NO:14,
SEQ ID NO:15,
SEQ ID NO:16,
SEQ ID NO:17 and
SEQ ID NO:18.

5. The peptide of claim 1 wherein the amino acid sequence consists of SEQ ID NO:13.

6. The peptide of claim 1 wherein the amino acid sequence consists of SEQ ID NO:14.

7. The peptide of claim 1 wherein the amino acid sequence consists of SEQ ID NO:15.

8. The peptide of claim 1 wherein the amino acid sequence consists of SEQ ID NO:16.

9. The peptide of claim 1 wherein the amino acid sequence consists of SEQ ID NO:17.

10. The peptide of claim 1 wherein the amino acid sequence consists of SEQ ID NO:18.

11. The chimeric protein of claim 4 wherein the DNA binding domain of said second STAT protein consists of SEQ ID NO:13.

12. The chimeric protein of claim 4 wherein the DNA binding domain of said second STAT protein consists of SEQ ID NO:14.

13. The chimeric protein of claim 4 wherein the DNA binding domain of said second STAT protein consists of SEQ ID NO:15.

14. The chimeric protein of claim 4 wherein the DNA binding domain of said second STAT protein consists of SEQ ID NO:16.

15. The chimeric protein of claim 4 wherein the DNA binding domain of said second STAT protein consists of SEQ ID NO:17.

16. The chimeric protein of claim 4 wherein the DNA binding domain of said second STAT protein consists of SEQ ID NO:18.

* * * * *